(12) United States Patent
Canney et al.

(10) Patent No.: US 9,464,062 B2
(45) Date of Patent: Oct. 11, 2016

(54) DISUBSTITUTED OXAZOLIDIN-2-ONES 5-HYDROXYTRYPTAMINE RECEPTOR 2B ACTIVITY MODULATORS

(71) Applicant: TEMPLE UNIVERSITY—OF THE COMMONWEALTH SYSTEM OF HIGHER EDUCATION, Philadelphia, PA (US)

(72) Inventors: Daniel J. Canney, Ambler, PA (US); Richie R. Bhandare, Maharashtra (IN); Benjamin E. Blass, Eagleville, PA (US); Magid Abou-Gharbia, Exton, PA (US)

(73) Assignee: TEMPLE UNIVERSITY—OF THE COMMONWEALTH SYSTEM OF HIGHER EDUCATION, Philadelphia, PA (US)

( * ) Notice: Subject to any disclaimer, the term of this patent is extended or adjusted under 35 U.S.C. 154(b) by 0 days.

(21) Appl. No.: 14/646,290

(22) PCT Filed: Nov. 26, 2013

(86) PCT No.: PCT/US2013/071926
§ 371 (c)(1),
(2) Date: May 20, 2015

(87) PCT Pub. No.: WO2014/085413
PCT Pub. Date: Jun. 5, 2014

(65) Prior Publication Data
US 2015/0291539 A1    Oct. 15, 2015

Related U.S. Application Data

(60) Provisional application No. 61/730,807, filed on Nov. 28, 2012.

(51) Int. Cl.
*C07D 263/20* (2006.01)
*C07D 413/06* (2006.01)
*C07D 263/24* (2006.01)

(52) U.S. Cl.
CPC ........... *C07D 263/20* (2013.01); *C07D 263/24* (2013.01); *C07D 413/06* (2013.01)

(58) Field of Classification Search
None
See application file for complete search history.

(56) References Cited

U.S. PATENT DOCUMENTS 4,883,797 A * 11/1989 Foguet ............... C07D 263/20
                                                    514/252.12
5,972,947 A   10/1999 Tsakiakidis et al.
7,141,583 B2  11/2006 Gravestock et al.
2011/0172222 A1  7/2011 Von Degenfeld et al.

FOREIGN PATENT DOCUMENTS

WO    03/068226 A1    8/2003
WO    2010033451 A2   3/2010

OTHER PUBLICATIONS

"Chemoinformatics" in Kirk-Othmer Encyclopedia of Chemical Technology, Hugo O. Villar, Published Online: Mar. 12, 2010, Copyright © 2001 by John Wiley & Sons, Inc. pp. 1-24.*
Goodman and Gilman's The Pharmacological Basis of Therapeutics, McGgraw Hill Medical, 2008, pp. 1-25.*
Kirk-Othmer Encyclopedia of Chemical Technology Copyright © 2002 by John Wiley & Sons, Inc., pp. 95-147, Article Online Posting Date: Aug. 16, 2002.*
Rouhi, "The Right Stuff, from research and development to the clinic, getting drug crystals right is full of pitfalls", Chemical & Engineering News, Feb. 24, 2003, pp. 32-35.*
Ullmann's Encyclopedia of Industrial Chemistry, Copyright © 2002 by Wiley-VCH Verlag GmbH & Co. KGaA , pp. 1-51.*
M. Kimura et al., Bioorg. Med. Chem. 11 (2003) 1621-1630.*
PubChem SureCN8259789, CID 20600757, pp. 1-4, Create Date: Dec. 5, 2007 [retrieved on Feb. 25, 2014]. Retrieved from the internet: <URL: http://pubchem.ncbi.nim.nih.gov/summary/summary.cgi?cid=20600757&loc=ec_rcs>.
PubChem SureCN6869814, CID 18404132, pp. 1-4, Create Date: Dec. 5, 2007 [retrieved on Feb. 25, 2014]. Retrieved from the internet: <URL: http://pubchem.ncbi.nim.nih.gov/summary/summary.cgi?cid-18404132&loc=ed_rcs>.
PubChem SureCN7307029, CID 19071005, pp. 1-2, Create Date: Dec. 5, 2007 [retrieved on Feb. 24, 2014]. Retrieved from the internet: <URL: http://pubchem.ncbi.nim.nih.gov/summary/summary.cgi?cid=19071005&loc=ec_rcs#x27>.
PubChem SureCN6551798, CID 22000698, pp. 1-3, Create Date: Dec. 5, 2007 [retreived on Feb. 24, 2014]. Retrieved from the internet: <URL: http://pubchem.ncbi.nim.nih.gov/summary/summary.cgi?cid=22000698&loc=ec_rcs>.
PubChem AC1MDPN4, CID 2793785, pp. 1-5, Create Date: Jul. 19, 2005 [retrieved on Feb. 24, 2014]. Retrieved from the internet: <URL: http://pubchem.ncbi.nim.nih.gov/summary/summary.cgi?q=all&cid=2793785#ec>.
PubChem SureCN7303927, CID 19071184, pp. 1-3, Create Date: Dec. 5, 1007 [retrieved on Feb. 25, 2014]. Retrieved from the internet: <URL: http://pubchem.ncbi.nim.nih.gov/summary/summary.cgi?cid=19071184&loc-ec_rcs>.
PubChem SureCN8109952, CID 15434827, pp. 1-4, Create Date: Feb. 10, 2007 [retrieved on Feb. 24, 2014]. Retrieved from the internet: <URL: http://pubchem.ncbi.nim.nih.gov/summary/summary.cgi?cid=15434827&loc=ec_rcs>.
PubChem CID 3016406, 3-amino-5-morpholinomethyl-2-oxazolidinone, pp. 1-4, Create Date: Aug. 8, 2005 [retrieved on Feb. 24, 2014]. Retrieved from the internet: <URL: http://pubchem.ncbi.nim.nih.gov/summary/summary.cgi?cid=3016406&loc=ec_rcs>.

(Continued)

*Primary Examiner* — Karl J Puttlitz
(74) *Attorney, Agent, or Firm* — Drinker Biddle & Reath LLP

(57) ABSTRACT

Pharmaceutical compositions of the invention comprise disubstituted oxazolidin-2-ones derivatives having a disease-modifying action in the treatment of diseases associated with dysregulation of 5-hydroxytryptamine receptor 2b activity.

14 Claims, No Drawings

(56) References Cited

OTHER PUBLICATIONS

Kim, SK et al. Predicted structures and dynamics for agonists and antagonists bound to serotonin 5-HT2B and 5-HT2C receptors. J Chem Inf Model, vol. 51, No. 2, pp. 420-433, Feb. 28, 2011 [retrieved on Feb. 24, 2014]. Retrieved from the internet: <URL: http://www.ncbi.nim.nih.gov/pmc/articles/PMC3070210/pdf/nihms272051.pdf>.

PCT/US2013/071926 International Search Report, and Written Opinion of the International Searching Authority, Mar. 20, 2014.

Chen, G. et al. Rational Drug Design Leading to the identification of a Potent 5-HT2c Agonist Lacking 5-HT2b Activity. ACS Med. Chem. Lett., 2, pp. 929-932, 2011.

\* cited by examiner

DISUBSTITUTED OXAZOLIDIN-2-ONES 5-HYDROXYTRYPTAMINE RECEPTOR 2B ACTIVITY MODULATORS

CROSS-REFERENCE TO RELATED APPLICATION

The benefit of the filing date of U.S. Provisional Patent Application No. 61/730,807, filed Nov. 28, 2012, is hereby claimed. The entire disclosure of the aforesaid application is incorporated herein by reference.

STATEMENT OF FEDERALLY FUNDED RESEARCH

The invention was made with government support under grant HHSN-271-2008-00025-C awarded by the National Institute of Mental Health. The government has certain rights in the invention.

FIELD OF INVENTION

The present invention relates to novel compounds useful as modulators of 5-hydroxytryptamine receptor 2b activity, and methods of their use and preparation. The compounds are useful for the treatment diseases that are associated with dysregulation of 5-hydroxytryptamine receptor 2b activity.

BACKGROUND OF THE INVENTION

Serotonin was discovered in the late 1940s and is present in both the peripheral and central nervous systems (Pytliak et al., *Physiol. Res.*, 60 (2011) 15-25; Cowen et al., *Psychopharmacology* 21 3 (2011) 167-169). Serotonin or 5-hydroxytryptamine (5-HT) is a monoamine neurotransmitter of the indolalkylamine group that acts at synapses of nerve cells. Seven distinct families of serotonin receptors have been identified and at least 20 subpopulations have been cloned on the basis of sequence similarity, signal transduction coupling and pharmacological characteristics. The seven families of 5-HT receptor are $5\text{-}HT_1$, $5\text{-}HT_2$, $5\text{-}HT_3$, $5\text{-}HT_4$, $5\text{-}HT_5$, $5\text{-}HT_6$, and $5\text{-}HT_7$. Each of these receptors in turn has subfamilies or subpopulations. The $5\text{-}HT_2$ subtype family consists of $5\text{-}HT_{2A}$, $5\text{-}HT_{2B}$ and $5\text{-}HT_{2C}$, all of which are G protein-coupled receptors. The signal transduction mechanism for all seven families has been studied. It is known that activation of $5\text{-}HT_1$ and $5\text{-}HT_5$ receptors causes a decrease in intracellular cAMP whereas activation of $5\text{-}HT_2$, $5\text{-}HT_3$, $5\text{-}HT_4$, $5\text{-}HT_6$, and $5\text{-}HT_7$ results in an increase in intracellular inositol-1,4,5-trisphosphate (IP3) and diacylglycerol (DAG). The 5-HT pathways in the brain are important targets for drug development in the area of CNS disorders. Serotonin binds to its a G-protein coupled receptor and is involved in a wide variety of actions including cognition, mood, anxiety, attention, appetite, cardiovascular function, vasoconstriction, and sleep among others (Chen et al., *ACS Medicinal Chemistry Letters* 2 (2011) 929-932; Pytliak et al., supra).

There is evidence that demonstrates a role for the $5\text{-}HT_{2b}$ receptor in a number of medical disorders, and therefore, $5\text{-}HT_{2b}$ receptor activity modulators would have a beneficial effect on patients suffering from these disorders. The disorders in which $5\text{-}HT_{2b}$ dysregulation plays a role and modulation of $5\text{-}HT_{2b}$ receptor activity by a therapeutic agent would provide therapeutic relief include, but are not limited to, irritable bowel syndrome (WO 01/08668), disorders of gastric motility, dyspepsia, constipation, diarrhea, Crohn's disease, ulcerative colitis, gastroesophageal reflux disease, tachygastria, migraine, neurogenic pain (WO 97/44326), nociceptive pain (U.S. Pat. No. 5,958,934), anxiety (WO 97/44326), depression (WO 97/44326), benign prostatic hyperplasia (U.S. Pat. No. 5,952,331), sleep disorder (WO 97/44326), panic disorder, obsessive compulsive disorder, alcoholism, hypertension, anorexia nervosa, priapism (WO/97/44236), asthma, obstructive airway dysfunction, chronic obstructive pulmonary disease (COPD) (U.S. Pat. No. 5,952,331), incontinence, bladder dysfunction (WO 96/24351), and pulmonary hypertension (Launay, J. M. et al., *Nature Medicine,* 2002, 8, 10, 1129-1135).

There is a long felt need for new $5\text{-}HT_{2b}$ receptor activity modulators that will provide therapeutic relief for patients suffering from diseases associated with dysregulation of 5-hydroxytryptamine receptor 2b activity. The present invention addresses the need to identify novel $5\text{-}HT_{2b}$ modulators capable of treating disease associated with dysregulation of 5-hydroxytryptamine receptor 2b activity. The present invention addresses the need to develop new therapeutic agents for the treatment and prevention of irritable bowel syndrome, disorders of gastric motility, dyspepsia, constipation, diarrhea, Crohn's disease, ulcerative colitis, gastroesophageal reflux disease, tachygastria, migraine, neurogenic pain, nociceptive pain, anxiety, depression, benign prostatic hyperplasia, sleep disorder, panic disorder, obsessive compulsive disorder, alcoholism, hypertension, anorexia nervosa, priapism, asthma, obstructive airway dysfunction, chronic obstructive pulmonary disease (COPD), incontinence, bladder dysfunction, and pulmonary hypertension.

BRIEF SUMMARY OF THE INVENTION

It has been found that certain compounds and compositions are useful for the treatment of diseases or disorders, including those involving dysregulation of 5-hydroxytryptamine receptor 2b activity. The biologically active compounds of the present invention are disubstituted oxazolidin-2-ones, compounds of formula (I),

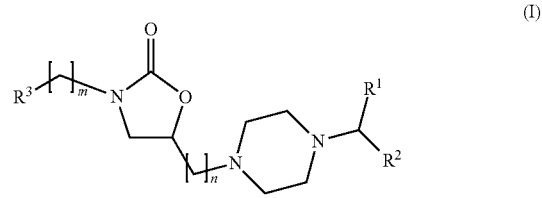

including hydrates, solvates, pharmaceutically acceptable salts, prodrugs and complexes thereof, wherein:

$R^1$ is selected from a group consisting of hydrogen, linear $C_1\text{-}C_6$ alkyl, branched $C_1\text{-}C_6$ alkyl, and optionally substituted aryl having 0-5 substituents;

$R^2$ is optionally substituted aryl having 0-5 substituents;

$R^3$ is selected from a group consisting of hydrogen, linear $C_1\text{-}C_6$ alkyl, branched $C_1\text{-}C_6$ alkyl, $C_3\text{-}C_7$ cycloalkyl, linear $C_1\text{-}C_6$ alkenyl, branched $C_1\text{-}C_6$ alkenyl, optionally substituted aryl, optionally substituted heteroaryl having 0-5 substituents,

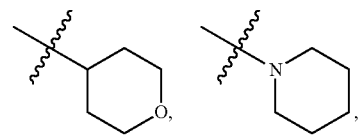

-continued

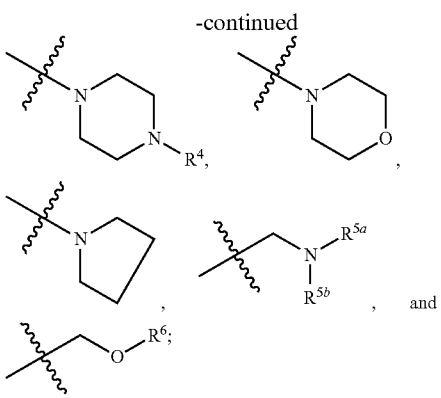

R⁴ is selected from a group consisting of hydrogen, linear $C_1$-$C_6$ alkyl, and branched $C_1$-$C_6$ alkyl;
$R^{5a}$ is selected from a group consisting of hydrogen, linear $C_1$-$C_6$ alkyl, and branched $C_1$-$C_6$ alkyl;
$R^{5b}$ is selected from a group consisting of hydrogen, linear $C_1$-$C_6$ alkyl, and branched $C_1$-$C_6$ alkyl;
$R^6$ is selected from a group consisting of hydrogen, linear $C_1$-$C_6$ alkyl, branched $C_1$-$C_6$ alkyl, and optionally substituted aryl having 0-5 substituents;
m is 0, 1, 2 or 3;
n is 1, 2, or 3.

The compounds of the present invention include compounds having formula (II):

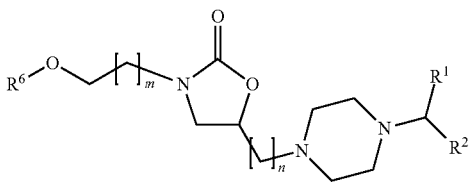

(II)

including hydrates, solvates, pharmaceutically acceptable salts, prodrugs and complexes thereof, wherein:
$R^1$ is selected from a group consisting of hydrogen, linear $C_1$-$C_6$ alkyl, branched $C_1$-$C_6$ alkyl, and optionally substituted aryl having 0-5 substituents;
$R^2$ is optionally substituted aryl having 0-5 substituents;
$R^6$ is selected from a group consisting of hydrogen, linear $C_1$-$C_6$ alkyl, branched $C_1$-$C_6$ alkyl and optionally substituted aryl having 0-5 substituents;
m is 0, 1, 2 or 3;
n is 1, 2, or 3.

The compounds of the present invention include compounds having formula (III):

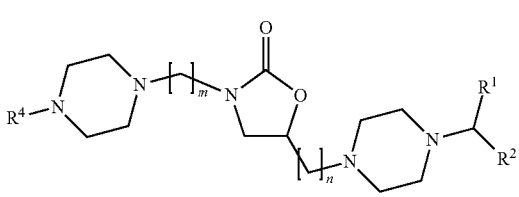

(III)

including hydrates, solvates, pharmaceutically acceptable salts, prodrugs and complexes thereof, wherein:

$R^1$ is selected from a group consisting of hydrogen, linear $C_1$-$C_6$ alkyl, branched $C_1$-$C_6$ alkyl, and optionally substituted aryl having 0-5 substituents;
$R^2$ is optionally substituted aryl having 0-5 substituents;
$R^4$ is selected from a group consisting of hydrogen, linear $C_1$-$C_6$ alkyl, and branched $C_1$-$C_6$ alkyl;
m is 0, 1, 2 or 3;
n is 1, 2, or 3.

The compounds of the present invention include compounds having formula (IV):

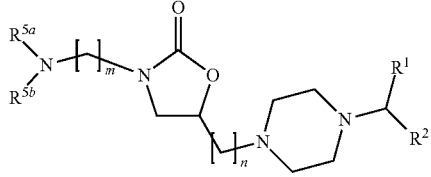

(IV)

including hydrates, solvates, pharmaceutically acceptable salts, prodrugs and complexes thereof, wherein:
$R^1$ is selected from a group consisting of hydrogen, linear $C_{1-6}$ alkyl, branched $C_{1-6}$ alkyl, and optionally substituted aryl having 0-5 substituents;
$R^2$ is optionally substituted aryl having 0-5 substituents;
$R^{5a}$ is selected from a group consisting of hydrogen, linear $C_{1-6}$ alkyl, and branched $C_{1-6}$ alkyl;
$R^{5b}$ is selected from a group consisting of hydrogen, linear $C_{1-6}$ alkyl, and branched $C_{1-6}$ alkyl;
m is 0, 1, 2 or 3;
n is 1, 2, or 3;

The present invention further relates to compositions comprising: an effective amount of one or more compounds according to the present invention or pharmaceutically acceptable salt, solvate, prodrug or complex thereof and an excipient.

The present invention also relates to a method for treating or preventing diseases or disorders that involve dysregulation of 5-hydroxytryptamine receptor 2b activity, including, for example, irritable bowel syndrome (IBS), disorders of gastric motility, dyspepsia, constipation, diarrhea, Crohn's disease, ulcerative colitis, gastroesophageal reflux disease, tachygastria. migraine, neurogenic pain, nociceptive pain, anxiety, depression, benign prostatic hyperplasia, sleep disorder, panic disorder, obsessive compulsive disorder, alcoholism, hypertension, anorexia nervosa, priapism, asthma, obstructive airway dysfunction, chronic obstructive pulmonary disease (COPD), incontinence, bladder dysfunction, and pulmonary hypertension, said method comprising administering to a subject in need of such treatment or prevention an effective amount of a compound or composition according to the present invention.

The present invention yet further relates to a method for treating or preventing diseases that involve dysregulation of 5-hydroxytryptamine receptor 2b activity, including, for example, irritable bowel syndrome, disorders of gastric motility, dyspepsia, constipation, diarrhea, Crohn's disease, ulcerative colitis, gastroesophageal reflux disease, tachygastria, migraine, neurogenic pain, nociceptive pain, anxiety, depression, benign prostatic hyperplasia, sleep disorder, panic disorder, obsessive compulsive disorder, alcoholism, hypertension, anorexia nervosa, priapism, asthma, obstructive airway dysfunction, chronic obstructive pulmonary disease (COPD), incontinence, bladder dysfunction, and pulmonary hypertension, wherein said method comprises administering to a subject in need of such treatment or prevention a composition comprising an effective amount of one or more compounds according to the present invention and an excipient.

The present invention also relates to a method for treating or preventing disease or conditions associated with dysregulation of 5-hydroxytryptamine receptor 2b activity such as irritable bowel syndrome, disorders of gastric motility, dyspepsia, constipation, diarrhea, Crohn's disease, ulcerative colitis, gastroesophageal reflux disease, tachygastria, migraine, neurogenic pain, pain, anxiety, depression, benign prostatic hyperplasia, sleep disorder, panic disorder, obsessive compulsive disorder, alcoholism, hypertension, anorexia nervosa, priapism, asthma, obstructive airway dysfunction, chronic obstructive pulmonary disease (COPD), incontinence, bladder dysfunction, and pulmonary hypertension, and diseases that involve dysregulation of 5-hydroxytryptamine receptor 2b activity. Said methods comprise administering to a subject in need of such treatment or prevention an effective amount of a compound or composition according to the present invention.

The present invention yet further relates to a method for treating or preventing disease or conditions associated with dysregulation of 5-hydroxytryptamine receptor 2b activity such as irritable bowel syndrome, disorders of gastric motility, dyspepsia, constipation, diarrhea, Crohn's disease, ulcerative colitis, gastroesophageal reflux disease, tachygastria, migraine, neurogenic pain, pain, anxiety, depression, benign prostatic hyperplasia, sleep disorder, panic disorder, obsessive compulsive disorder, alcoholism, hypertension, anorexia nervosa, priapism, asthma, obstructive airway dysfunction, chronic obstructive pulmonary disease (COPD), incontinence, bladder dysfunction, and pulmonary hypertension, and diseases that involve dysregulation of 5-hydroxytryptamine receptor 2b activity, wherein said method comprises administering to a subject in need of such treatment or prevention a composition comprising an effective amount of one or more compounds according to the present invention and an excipient.

The present invention also relates to a method for treating or preventing disease or conditions associated with dysregulation of 5-hydroxytryptamine receptor 2b activity. Said methods comprise administering to a subject in need of such treatment or prevention an effective amount of a compound or composition according to the present invention.

The present invention yet further relates to a method for treating or preventing disease or conditions associated with dysregulation of 5-hydroxytryptamine receptor 2b activity, wherein said method comprises administering to a subject in need of such treatment or prevention a composition comprising an effective amount of one or more compounds according to the present invention and an excipient.

The present invention further relates to a process for preparing the 5-hydroxytryptamine receptor 2b activity modulators of the present invention.

These and other objects, features, and advantages will become apparent to those of ordinary skill in the art from a reading of the following detailed description and the appended claims. All percentages, ratios and proportions herein are by weight, unless otherwise specified. All temperatures are in degrees Celsius (° C.) unless otherwise specified. All documents cited are in relevant part, incorporated herein by reference; the citation of any document is not to be construed as an admission that it is prior art with respect to the present invention.

DETAILED DESCRIPTION OF THE INVENTION

The $5\text{-HT}_{2B}$ receptor activity modulators of the present invention are capable of treating and preventing diseases or disorders associated with dysregulation of $5\text{-HT}_{2B}$ receptor activity. By "diseases or disorder associated with dysregulation of $5\text{-HT}_{2B}$ receptor activity" is meant a disease or disorder in which activity of the $5\text{-HT}_{2B}$ receptor is outside of a normal physiological range.

It has been discovered that the 5-hydroxytryptamine receptor 2b play a role in a number of medical disorders, and therefore, $5\text{-HT}_{2b}$ receptor activity modulators would have a beneficial effect on patients suffering from these disorders. The disorders in which $5\text{-HT}_{2b}$ dysregulation plays a role and modulation of $5\text{-HT}_{2b}$ receptor activity by a therapeutic agent is a viable approach to therapeutic relief include, but are not limited to, irritable bowel syndrome (WO 01/08668), disorders of gastric motility, dyspepsia, constipation, diarrhea, Crohn's disease, ulcerative colitis, gastroesophageal reflux disease, tachygastria, migraine, neurogenic pain (WO 97/44326), pain (U.S. Pat. No. 5,958,934), anxiety (WO 97/44326), depression (WO 97/44326), benign prostatic hyperplasia (U.S. Pat. No. 5,952,331), sleep disorder (WO 97/44326), panic disorder, obsessive compulsive disorder, alcoholism, hypertension, anorexia nervosa, priapism (WO/97/44236), asthma, obstructive airway dysfunction (U.S. Pat. No. 5,952,331), incontinence, bladder dysfunction (WO 96/24351), chronic obstructive pulmonary disease (COPD), and pulmonary hypertension (Launay, J. M. et. Al. Nature Medicine, 2002, 8, 10, 1129-1135).

Without wishing to be limited by theory, it is believed that 5-hydroxytryptamine receptor 2b receptor activity modulators of the present invention can ameliorate, abate, otherwise cause to be controlled, diseases and disorders associated with dysregulation of 5-hydroxytryptamine receptor 2b activity. The diseases and disorders include, but are not limited to irritable bowel syndrome, disorders of gastric motility, constipation, diarrhea, Crohn's disease, ulcerative colitis, dyspepsia, gastroesophageal reflux disease, tachygastria, migraine, neurogenic pain, nociceptive pain, anxiety, depression, benign prostatic hyperplasia, sleep disorder, panic disorder, obsessive compulsive disorder, alcoholism, hypertension, anorexia nervosa, priapism, asthma, obstructive airway dysfunction, chronic obstructive pulmonary disease (COPD), incontinence, bladder dysfunction, and pulmonary hypertension.

Throughout the description, where compositions are described as having, including, or comprising specific components, or where processes are described as having, including, or comprising specific process steps, it is contemplated that compositions of the present invention also consist essentially of, or consist of, the recited components, and that the processes of the present invention also consist essentially of, or consist of, the recited processing steps.

In the application, where an element or component is said to be included in and/or selected from a list of recited elements or components, it should be understood that the element or component can be any one of the recited elements or components and can be selected from a group consisting of two or more of the recited elements or components.

The use of the singular herein includes the plural (and vice versa) unless specifically stated otherwise. In addition, where the use of the term "about" is before a quantitative value, the present teachings also include the specific quantitative value itself, unless specifically stated otherwise.

It should be understood that the order of steps or order for performing certain actions is immaterial so long as the present teachings remain operable. Moreover, two or more steps or actions can be conducted simultaneously As used herein, the term "halogen" shall mean chlorine, bromine, fluorine and iodine.

As used herein, unless otherwise noted, "alkyl" and/or "aliphatic" whether used alone or as part of a substituent group refers to straight and branched carbon chains having 1 to 20 carbon atoms or any number within this range, for example 1 to 6 carbon atoms or 1 to 4 carbon atoms. Designated numbers of carbon atoms (e.g. $C_1$-$C_6$) shall refer independently to the number of carbon atoms in an alkyl moiety or to the alkyl portion of a larger alkyl-containing substituent. Non-limiting examples of alkyl groups include methyl, ethyl, n-propyl, iso-propyl, n-butyl, sec-butyl, iso-butyl, tert-butyl, and the like. Alkyl groups can be optionally substituted. Non-limiting examples of substituted alkyl groups include hydroxymethyl, chloromethyl, trifluoromethyl, aminomethyl, 1-chloroethyl, 2-hydroxyethyl, 1,2-difluoroethyl, 3-carboxypropyl, and the like. In substituent groups with multiple alkyl groups such as ($C_1$-$C_6$alkyl)$_2$ amino, the alkyl groups may be the same or different.

As used herein, the terms "alkenyl" and "alkynyl" groups, whether used alone or as part of a substituent group, refer to straight and branched carbon chains having 2 or more carbon atoms, preferably 2 to 20, wherein an alkenyl chain has at least one double bond in the chain and an alkynyl chain has at least one triple bond in the chain. Alkenyl and alkynyl groups can be optionally substituted (respectively, "optionally substituted alkenyl" and "optionally substituted alkynyl)". Nonlimiting examples of alkenyl groups include ethenyl, 3-propenyl, 1-propenyl (also 2-methylethenyl), isopropenyl (also 2-methylethen-2-yl), buten-4-yl, and the like. Nonlimiting examples of substituted alkenyl groups include 2-chloroethenyl (also 2-chlorovinyl), 4-hydroxybuten-1-yl, 7-hydroxy-7-methyloct-4-en-2-yl, 7-hydroxy-7-methyloct-3,5-dien-2-yl, and the like. Nonlimiting examples of alkynyl groups include ethynyl, prop-2-ynyl (also propargyl), propyn-1-yl, and 2-methyl-hex-4-yn-1-yl. Nonlimiting examples of substituted alkynyl groups include, 5-hydroxy-5-methylhex-3-ynyl, 6-hydroxy-6-methylhept-3-yn-2-yl, 5-hydroxy-5-ethylhept-3-ynyl, and the like.

As used herein, "cycloalkyl," whether used alone or as part of another group, refers to a non-aromatic carbon-containing ring including cyclized alkyl, alkenyl, and alkynyl groups, e.g., having from 3 to 14 ring carbon atoms, preferably from 3 to 7 or 3 to 6 ring carbon atoms, or even 3 to 4 ring carbon atoms, and optionally containing one or more (e.g., 1, 2, or 3) double or triple bonds. Cycloalkyl groups can be monocyclic (e.g., cyclohexyl) or polycyclic (e.g., containing fused, bridged, and/or spiro ring systems), wherein the carbon atoms are located inside or outside of the ring system. Any suitable ring position of the cycloalkyl group can be covalently linked to the defined chemical structure. Cycloalkyl rings can be optionally substituted. Nonlimiting examples of cycloalkyl groups include: cyclopropyl, 2-methyl-cyclopropyl, cyclopropenyl, cyclobutyl, 2,3-dihydroxycyclobutyl, cyclobutenyl, cyclopentyl, cyclopentenyl, cyclopentadienyl, cyclohexyl, cyclohexenyl, cycloheptyl, cyclooctanyl, decalinyl, 2,5-dimethylcyclopentyl, 3,5-dichlorocyclohexyl, 4-hydroxycyclohexyl, 3,3,5-trimethylcyclohex-1-yl, octahydropentalenyl, octahydro-1H-indenyl, 3a,4,5,6,7,7a-hexahydro-3H-inden-4-yl, decahydroazulenyl; bicyclo[6.2.0]decanyl, decahydronaphthalenyl, and dodecahydro-1H-fluorenyl. The term "cycloalkyl" also include carbocyclic rings which are bicyclic hydrocarbon rings, non-limiting examples of which include, bicyclo-[2.1.1]hexanyl, bicyclo[2.2.1]heptanyl, bicyclo[3.1.1]heptanyl, 1,3-dimethyl[2.2.1]heptan-2-yl, bicyclo[2.2.2]octanyl, and bicyclo[3.3.3]undecanyl.

"Haloalkyl" is intended to include both branched and straight-chain saturated aliphatic hydrocarbon groups having the specified number of carbon atoms, substituted with one or more halogens. Haloalkyl groups include, for example, perhaloalkyl groups, wherein all hydrogens of an alkyl group have been replaced with halogens (e.g., —$CF_3$, —$CF_2CF_3$). Haloalkyl groups can optionally be substituted with one or more substituents in addition to halogen. Examples of haloalkyl groups include, but are not limited to, fluoromethyl, dichloroethyl, trifluoromethyl, trichloromethyl, pentafluoroethyl, and pentachloroethyl groups.

The term "alkoxy" refers to the group —O-alkyl, wherein the alkyl group is as defined above. Alkoxy groups optionally may be substituted. The term "$C_3$-$C_6$ cyclic alkoxy" refers to a ring containing 3 to 6 carbon atoms and at least one oxygen atom (e.g., tetrahydrofuran, tetrahydro-2H-pyran). $C_3$-$C_6$ cyclic alkoxy groups optionally may be substituted.

The term "aryl," wherein used alone or as part of another group, is defined herein as a an unsaturated, aromatic monocyclic ring of 6 carbon members or to an unsaturated, aromatic polycyclic ring of from 10 to 14 carbon members. Aryl rings can be, for example, phenyl, naphthyl, anthryl ring each optionally substituted with one or more moieties capable of replacing one or more hydrogen atoms. Non-limiting examples of aryl groups include: phenyl, naphthylen-1-yl and naphthylen-2-yl. Non-limiting examples of substituted aryl include 4-fluorophenyl, 2-hydroxyphenyl, 3-methylphenyl, 2-amino-4-fluorophenyl, 2-(N,N-diethylamino)phenyl, 2-cyanophenyl, 2,6-di-tert-butylphenyl, 3-methoxyphenyl, 8-hydroxynaphthylen-2-yl 4,5-dimethoxynaphthylen-1-yl, and 6-cyano-naphthylen-1-yl. Aryl groups also include, for example, phenyl or naphthyl rings fused with one or more saturated or partially saturated carbon rings (e.g., bicyclo[4.2.0]octa-1,3,5-trienyl, indanyl), which can be substituted at one or more carbon atoms of the aromatic and/or saturated or partially saturated rings.

The term "arylalkyl" or "aralkyl" refers to the group -alkyl-aryl, where the alkyl and aryl groups are as defined herein. Aralkyl groups may be optionally substituted in either to alkyl chain or in the aryl moiety. Examples of arylalkyl groups include, for example, benzyl, 1-phenylethyl, 2-phenylethyl, 3-phenylpropyl, 2-phenylpropyl, fluorenylmethyl and the like.

The terms "heterocyclic" and/or "heterocycle" and/or "heterocylyl," whether used alone or as part of another group, are defined herein as one or more rings having from 3 to 20 atoms wherein at least one atom in at least one ring is a heteroatom selected from nitrogen (N), oxygen (O), or sulfur (S), and wherein further the ring that includes the heteroatom is non-aromatic. In heterocycle groups that include 2 or more fused rings, the non-heteroatom bearing ring may be aryl (e.g., indolinyl, tetrahydroquinolinyl, chromanyl). Exemplary heterocycle groups have from 3 to 14 ring atoms of which from 1 to 5 are heteroatoms independently selected from nitrogen (N), oxygen (O), or sulfur (S). One or more N or S atoms in a heterocycle group can be oxidized. Heterocycle groups can be optionally substituted.

Non-limiting examples of heterocyclic units having a single ring include: diazirinyl, aziridinyl, urazolyl, azetidinyl, pyrazolidinyl, imidazolidinyl, oxazolidinyl, isoxazolinyl, isoxazolyl, thiazolidinyl, isothiazolyl, isothiazolinyl oxathiazolidinonyl, oxazolidinonyl, hydantoinyl, tetrahydrofuranyl, pyrrolidinyl, morpholinyl, piperazinyl, piperidinyl, dihydropyranyl, tetrahydropyranyl, piperidin-2-onyl (valerolactam), 2,3,4,5-tetrahydro-1H-azepinyl, 2,3-dihydro-1H-indole, and 1,2,3,4-tetrahydro-quinoline. Non-limiting examples of heterocyclic units having 2 or more rings include: hexahydro-1H-pyrrolizinyl, 3a,4,5,6,7,7a-hexahydro-1H-benzo[d]imidazolyl, 3a,4,5,6,7,7a-hexahydro-1H-indolyl, 1,2,3,4-tetrahydroquinolinyl, chromanyl, isochromanyl, indolinyl, isoindolinyl, and decahydro-1H-cycloocta[b]pyrrolyl.

The term "heteroaryl," whether used alone or as part of another group, is defined herein as one or more rings having from 5 to 20 atoms wherein at least one atom in at least one ring is a heteroatom chosen from nitrogen (N), oxygen (O), or sulfur (S), and wherein further at least one of the rings that includes a heteroatom is aromatic. In heteroaryl groups that include 2 or more fused rings, the non-heteroatom bearing ring may be a carbocycle (e.g., 6,7-dihydro-5H-cyclopentapyrimidine) or aryl (e.g., benzofuranyl, benzothiophenyl, indolyl). Exemplary heteroaryl groups have from 5 to 14 ring atoms and contain from 1 to 5 ring heteroatoms independently selected from nitrogen (N), oxygen (O), or sulfur (S). One or more N or S atoms in a heteroaryl group can be oxidized. Heteroaryl groups can be optionally substituted ("optionally substituted heteroaryl"). Non-limiting examples of heteroaryl rings containing a single ring include: 1,2,3,4-tetrazolyl, [1,2,3]triazolyl, [1,2,4]triazolyl, triazinyl, thiazolyl, 1H-imidazolyl, oxazolyl, furanyl, thiopheneyl, pyrimidinyl, 2-phenylpyrimidinyl, pyridinyl, 3-methylpyridinyl, and 4-dimethylaminopyridinyl. Non-limiting examples of heteroaryl rings containing 2 or more fused rings include: benzofuranyl, benzothiophenyl, benzoxazolyl, benzthiazolyl, benztriazolyl, cinnolinyl, naphthyridinyl, phenanthridinyl, 7H-purinyl, 9H-purinyl, 6-amino-9H-purinyl, 5H-pyrrolo[3,2-d]pyrimidinyl, 7H-pyrrolo[2,3-d]pyrimidinyl, pyrido[2,3-d]pyrimidinyl, 2-phenylbenzo[d]thiazolyl, 1H-indolyl, 4,5,6,7-tetrahydro-1-H-indolyl, quinoxalinyl, 5-methylquinoxalinyl, quinazolinyl, quinolinyl, 8-hydroxy-quinolinyl, and isoquinolinyl.

One non-limiting example of a heteroaryl group as described above is $C_1$-$C_5$ heteroaryl, which has 1 to 5 carbon ring atoms and at least one additional ring atom that is a heteroatom (preferably 1 to 4 additional ring atoms that are heteroatoms) independently selected from nitrogen (N), oxygen (O), or sulfur (S). Examples of $C_1$-$C_5$ heteroaryl include, but are not limited to, triazinyl, thiazol-2-yl, thiazol-4-yl, imidazol-1-yl, 1H-imidazol-2-yl, 1H-imidazol-4-yl, isoxazolin-5-yl, furan-2-yl, furan-3-yl, thiophen-2-yl, thiophen-4-yl, pyrimidin-2-yl, pyrimidin-4-yl, pyrimidin-5-yl, pyridin-2-yl, pyridin-3-yl, and pyridin-4-yl.

Unless otherwise noted, when two substituents are taken together to form a ring having a specified number of ring atoms (e.g., $R^2$ and $R^3$ taken together with the nitrogen (N) to which they are attached to form a ring having from 3 to 7 ring members), the ring can have carbon atoms and optionally one or more (e.g., 1 to 3) additional heteroatoms independently selected from nitrogen (N), oxygen (O), or sulfur (S). The ring can be saturated or partially saturated and can be optionally substituted.

For the purposes of the present invention fused ring units, as well as spirocyclic rings, bicyclic rings and the like, which comprise a single heteroatom will be considered to belong to the cyclic family corresponding to the heteroatom containing ring. For example, 1,2,3,4-tetrahydroquinoline having the formula:

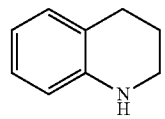

is, for the purposes of the present invention, considered a heterocyclic unit. 6,7-Dihydro-5H-cyclopentapyrimidine having the formula:

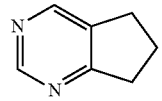

is, for the purposes of the present invention, considered a heteroaryl unit. When a fused ring unit contains heteroatoms in both a saturated and an aryl ring, the aryl ring will predominate and determine the type of category to which the ring is assigned. For example, 1,2,3,4-tetrahydro-[1,8]naphthyridine having the formula:

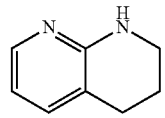

is, for the purposes of the present invention, considered a heteroaryl unit.

Whenever a term or either of their prefix roots appear in a name of a substituent the name is to be interpreted as including those limitations provided herein. For example, whenever the term "alkyl" or "aryl" or either of their prefix roots appear in a name of a substituent (e.g., arylalkyl, alkylamino) the name is to be interpreted as including those limitations given above for "alkyl" and "aryl."

The term "substituted" is used throughout the specification. The term "substituted" is defined herein as a moiety, whether acyclic or cyclic, which has one or more hydrogen atoms replaced by a substituent or several (e.g., 1 to 10) substituents as defined herein below. The substituents are capable of replacing one or two hydrogen atoms of a single moiety at a time. In addition, these substituents can replace two hydrogen atoms on two adjacent carbons to form said substituent, new moiety or unit. For example, a substituted unit that requires a single hydrogen atom replacement includes halogen, hydroxyl, and the like. A two hydrogen atom replacement includes carbonyl, oximino, and the like. A two hydrogen atom replacement from adjacent carbon atoms includes epoxy, and the like. The term "substituted" is used throughout the present specification to indicate that a moiety can have one or more of the hydrogen atoms replaced by a substituent. When a moiety is described as "substituted" any number of the hydrogen atoms may be replaced. For example, difluoromethyl is a substituted C1 alkyl; trifluoromethyl is a substituted C1 alkyl; 4-hydroxyphenyl is a substituted aromatic ring; (N,N-dimethyl-5-amino)octanyl is a substituted C8 alkyl; 3-guanidinopropyl is a substituted C3 alkyl; and 2-carboxypyridinyl is a substituted heteroaryl.

The variable groups defined herein, e.g., alkyl, alkenyl, alkynyl, cycloalkyl, alkoxy, aryloxy, aryl, heterocycle and heteroaryl groups defined herein, whether used alone or as part of another group, can be optionally substituted. Optionally substituted groups will be so indicated.

The following are non-limiting examples of substituents which can substitute for hydrogen atoms on a moiety: halogen (chlorine (Cl), bromine (Br), fluorine (F) and iodine (I)), —CN, —$NO_2$, oxo (=O), —$OR^7$, —$SR^7$, —$N(R^7)_2$, —$NR^7C(O)R^7$, —$SO_2R^7$, —$SO_2OR^7$, —$SO_2N(R^7)_2$, —$C(O)R^7$, —$C(O)OR^7$, —$C(O)N(R^7)_2$, $C_1$-$C_6$ alkyl, $C_1$-$C_6$ haloalkyl, $C_1$-$C_6$ alkoxy, $C_2$-$C_8$ alkenyl, $C_2$-$C_8$ alkynyl, $C_3$-$C_{14}$ cycloalkyl, aryl, heterocycle, or heteroaryl, wherein each of the alkyl, haloalkyl, alkenyl, alkynyl, alkoxy, cycloalkyl, aryl, heterocycle, and heteroaryl groups is optionally substituted with 1-10 (e.g., 1-6 or 1-4) groups selected independently from halogen, —CN, —$NO_2$, oxo, and $R^7$; wherein $R^7$, at each occurrence, independently is hydrogen, —$OR^8$, —$SR^8$, —$C(O)R^8$, —$C(O)OR^8$, —$C(O)N(R^8)_2$, —$SO_2R^8$, —$S(O)_2OR^8$, —$N(R^8)_2$, —$NR^8C(O)R^8$, $C_1$-$C_6$ alkyl, $C_1$-$C_6$ haloalkyl, $C_2$-$C_8$ alkenyl, $C_2$-$C_8$ alkynyl, cycloalkyl (e.g., $C_{3-6}$ cycloalkyl), aryl, heterocycle, or heteroaryl, or two $R^7$ units taken together with the atom(s) to which they are bound form an optionally substituted carbocycle or heterocycle wherein said carbocycle or heterocycle has 3 to 7 ring atoms; wherein $R^8$, at each occurrence, independently is hydrogen, $C_1$-$C_6$ alkyl, $C_1$-$C_6$ haloalkyl, $C_2$-$C_8$ alkenyl, $C_2$-$C_8$ alkynyl, cycloalkyl (e.g., $C_3$-$C_6$ cycloalkyl), aryl, heterocycle, or heteroaryl, or two $R^8$ units taken together with the atom(s) to which they are bound form an optionally substituted carbocycle or heterocycle wherein said carbocycle or heterocycle preferably has 3 to 7 ring atoms.

In some embodiments, the substituents are selected from
(i) —$OR^9$; for example, —OH, —$OCH_3$, —$OCH_2CH_3$, —$OCH_2CH_2CH_3$;
(ii) —$C(O)R^9$; for example, —$COCH_3$, —$COCH_2CH_3$, —$COCH_2CH_2CH_3$;
(iii) —$C(O)OR^9$; for example, —$CO_2CH_3$, —$CO_2CH_2CH_3$, —$CO_2CH_2CH_2CH_3$;
(iv) —$C(O)N(R^9)_2$; for example, —$CONH_2$, —$CONHCH_3$, —$CON(CH_3)_2$;
(v) —$N(R^9)_2$; for example, —$NH_2$, —$NHCH_3$, —$N(CH_3)_2$, —$NH(CH_2CH_3)$;
(vi) halogen: —F, —Cl, —Br, and —I;
(vii) —$CH_eX_g$; wherein X is halogen, and e+g=3; for example, —$CH_2F$, —$CHF_2$, —$CF_3$, —$CCl_3$, or —$CBr_3$;
(viii) —$SO_2R^9$; for example, —$SO_2H$; —$SO_2CH_3$; —$SO_2C_6H_5$;
(ix) $C_1$-$C_6$ linear, branched, or cyclic alkyl;
(x) Cyano
(xi) Nitro;
(xii) $N(R^9)C(O)R^9$;
(xiii) Oxo (=O);
(xiv) Heterocycle; and
(xv) Heteroaryl.
wherein each $R^9$ is independently hydrogen, optionally substituted $C_1$-$C_6$ linear or branched alkyl (e.g., optionally substituted $C_1$-$C_4$ linear or branched alkyl), or optionally substituted $C_3$-$C_6$ cycloalkyl (e.g optionally substituted $C_3$-$C_4$ cycloalkyl); or two $R^9$ units can be taken together to form a ring comprising 3-7 ring atoms. In certain aspects, each $R^9$ is independently hydrogen, $C_1$-$C_6$ linear or branched alkyl optionally substituted with halogen or $C_3$-$C_6$ cycloalkyl or $C_3$-$C_6$ cycloalkyl.

At various places in the present specification, substituents of compounds are disclosed in groups or in ranges. It is specifically intended that the description include each and every individual subcombination of the members of such groups and ranges. For example, the term "$C_1$-$C_6$ alkyl" is specifically intended to individually disclose $C_1$, $C_2$, $C_3$, $C_4$, $C_5$, $C_6$, $C_1$-$C_6$, $C_1$-$C_5$, $C_1$-$C_4$, $C_1$-$C_3$, $C_1$-$C_2$, $C_2$-$C_6$, $C_2$-$C_5$, $C_2$-$C_4$, $C_2$-$C_3$, $C_3$-$C_6$, $C_3$-$C_5$, $C_3$-$C_4$, $C_4$-$C_6$, $C_4$-$C_5$, and $C_5$-$C_6$, alkyl.

For the purposes of the present invention the terms "compound," "analog," and "composition of matter" stand equally well for the 5-hydroxytryptamine receptor 2b activity modulators described herein, including all enantiomeric forms, diastereomeric forms, salts, and the like, and the terms "compound," "analog," and "composition of matter" are used interchangeably throughout the present specification.

Compounds described herein can contain an asymmetric atom (also referred as a chiral center), and some of the compounds can contain one or more asymmetric atoms or centers, which can thus give rise to optical isomers (enantiomers) and diastereomers. The present teachings and compounds disclosed herein include such enantiomers and diastereomers, as well as the racemic and resolved, enantiomerically pure R and S stereoisomers, as well as other mixtures of the R and S stereoisomers and pharmaceutically acceptable salts thereof. Optical isomers can be obtained in pure form by standard procedures known to those skilled in the art, which include, but are not limited to, diastereomeric salt formation, kinetic resolution, and asymmetric synthesis. The present teachings also encompass cis and trans isomers of compounds containing alkenyl moieties (e.g., alkenes and imines). It is also understood that the present teachings encompass all possible regioisomers, and mixtures thereof, which can be obtained in pure form by standard separation procedures known to those skilled in the art, and include, but are not limited to, column chromatography, thin-layer chromatography, and high-performance liquid chromatography.

Pharmaceutically acceptable salts of compounds of the present teachings, which can have an acidic moiety, can be formed using organic and inorganic bases. Both mono and polyanionic salts are contemplated, depending on the number of acidic hydrogens available for deprotonation. Suitable salts formed with bases include metal salts, such as alkali metal or alkaline earth metal salts, for example sodium, potassium, or magnesium salts; ammonia salts and organic amine salts, such as those formed with morpholine, thiomorpholine, piperidine, pyrrolidine, a mono-, di- or tri-lower alkylamine (e.g., ethyl-tert-butyl-, diethyl-, diisopropyl-, triethyl-, tributyl- or dimethylpropylamine), or a mono-, di-, or trihydroxy lower alkylamine (e.g., mono-, di- or triethanolamine). Specific non-limiting examples of inorganic bases include $NaHCO_3$, $Na_2CO_3$, $KHCO_3$, $K_2CO_3$, $Cs_2CO_3$, LiOH, NaOH, KOH, $NaH_2PO_4$, $Na_2HPO_4$, and $Na_3PO_4$. Internal salts also can be formed. Similarly, when a compound disclosed herein contains a basic moiety, salts can be formed using organic and inorganic acids. For example, salts can be formed from the following acids: acetic, propionic, lactic, benzenesulfonic, benzoic, camphorsulfonic, citric, tartaric, succinic, dichloroacetic, ethenesulfonic, formic, fumaric, gluconic, glutamic, hippuric, hydrobromic, hydrochloric, isethionic, lactic, maleic, malic, malonic, mandelic, methanesulfonic, mucic, napthalenesulfonic, nitric, oxalic, pamoic, pantothenic, phosphoric, phthalic, propionic, succinic, sulfuric, tartaric, toluenesulfonic, and camphorsulfonic as well as other known pharmaceutically acceptable acids.

When any variable occurs more than one time in any constituent or in any formula, its definition in each occurrence is independent of its definition at every other occurrence (e.g., in $N(R^8)_2$, each $R^8$ may be the same or different than the other). Combinations of substituents and/or variables are permissible only if such combinations result in stable compounds.

The terms "treat" and "treating" and "treatment" as used herein, refer to partially or completely alleviating, inhibiting, ameliorating and/or relieving a condition from, which a patient is suspected to suffer.

As used herein, "therapeutically effective" and "effective dose" refer to a substance or an amount that elicits a desirable biological activity or effect.

Except when noted, the terms "subject" or "patient" are used interchangeably and refer to mammals such as human patients and non-human primates, as well as experimental animals such as rabbits, rats, and mice, and other animals. Accordingly, the term "subject" or "patient" as used herein means any mammalian patient or subject to which the compounds of the invention can be administered. In an exemplary embodiment of the present invention, to identify subject patients for treatment according to the methods of the invention, accepted screening methods are employed to determine risk factors associated with a targeted or suspected disease or condition or to determine the status of an existing disease or condition in a subject. These screening methods include, for example, conventional work-ups to determine risk factors that may be associated with the targeted or suspected disease or condition. These and other routine methods allow the clinician to select patients in need of therapy using the methods and compounds of the present invention.

The 5-Hydroxytryptamine Receptor 2b Activity Modulators Agents

The 5-hydroxytryptamine receptor 2b activity modulators of the present invention are disubstituted oxazolidin-2-ones, and include all enantiomeric and diastereomeric forms and pharmaceutically accepted salts thereof having the formula:

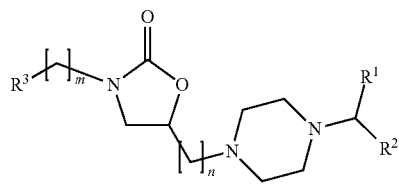

(I)

including hydrates, solvates, pharmaceutically acceptable salts, prodrugs and complexes thereof, wherein:

$R^1$ is selected from a group consisting of hydrogen, linear $C_1$-$C_6$ alkyl, branched $C_1$-$C_6$ alkyl, and optionally substituted aryl having 0-5 substituents;

$R^2$ is optionally substituted aryl having 0-5 substituents;

$R^3$ is selected from a group consisting of hydrogen, linear $C_1$-$C_6$ alkyl, branched $C_1$-$C_6$ alkyl, $C_3$-$C_7$ cycloalkyl, linear $C_1$-$C_6$ alkenyl, branched $C_1$-$C_6$ alkenyl, optionally substituted aryl, optionally substituted heteroaryl,

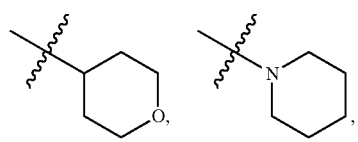

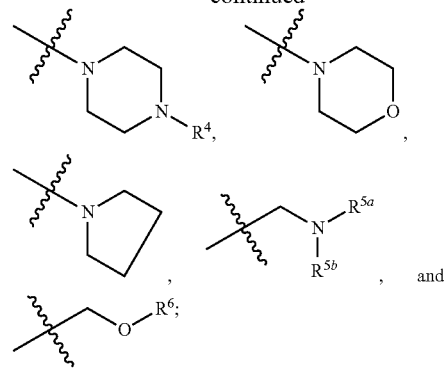

$R^4$ is selected from a group consisting of hydrogen, linear $C_1$-$C_6$ alkyl, and branched $C_1$-$C_6$ alkyl;

$R^{5a}$ is selected from a group consisting of hydrogen, linear $C_1$-$C_6$ alkyl, and branched $C_1$-$C_6$ alkyl;

$R^{5b}$ is selected from a group consisting of hydrogen, linear $C_1$-$C_6$ alkyl, and branched $C_1$-$C_6$ alkyl;

$R^6$ is selected from a group consisting of hydrogen, linear $C_1$-$C_6$ alkyl, branched $C_1$-$C_6$ alkyl, and optionally substituted aryl having 0-5 substituents;

m is 0, 1, 2, or 3;

n is 1, 2, or 3;

The compounds of the present invention include compounds having formula (II):

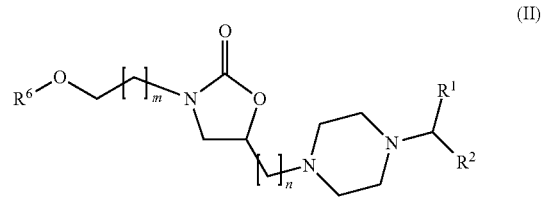

(II)

including hydrates, solvates, pharmaceutically acceptable salts, prodrugs and complexes thereof, wherein:

$R^1$ is selected from a group consisting of hydrogen, linear $C_1$-$C_6$ alkyl, branched $C_1$-$C_6$ alkyl, and optionally substituted aryl having 0-5 substituents;

$R^2$ is optionally substituted aryl $R^2$ having 0-5 substitutents;

$R^6$ is selected from a group consisting of hydrogen, linear $C_1$-$C_6$ alkyl, branched $C_1$-$C_6$ alkyl, and optionally substituted aryl having 0-5 substituents;

m is 0, 1, 2 or 3;

n is 1, 2, or 3;

The compounds of the present invention include compounds having formula (III):

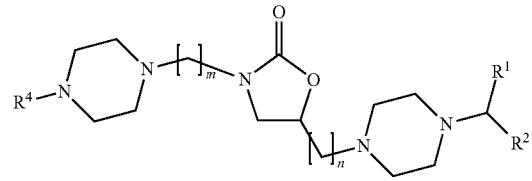

(III)

including hydrates, solvates, pharmaceutically acceptable salts, prodrugs and complexes thereof, wherein:

$R^1$ is selected from a group consisting of hydrogen, linear $C_1$-$C_6$ alkyl, branched $C_1$-$C_6$ alkyl, and optionally substituted aryl having 0-5 substituents;

$R^2$ is optionally substituted aryl having 0-5 substituents;

$R^4$ is selected from a group consisting of hydrogen, linear $C_1$-$C_6$ alkyl, and branched $C_1$-$C_6$ alkyl;

m is 0, 1, 2 or 3;

n is 1, 2, or 3;

The compounds of the present invention include compounds having formula (IV):

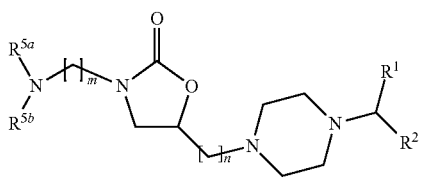

(IV)

including hydrates, solvates, pharmaceutically acceptable salts, prodrugs and complexes thereof, wherein:

$R^1$ is selected from a group consisting of hydrogen, linear $C_1$-$C_6$ alkyl, branched $C_1$-$C_6$ alkyl, and optionally substituted aryl having 0-5 substituents;

$R^2$ is optionally substituted aryl where $R^2$ having 0-5 substituents;

$R^{5a}$ is selected from a group consisting of hydrogen, linear $C_1$-$C_6$ alkyl, and branched $C_1$-$C_6$ alkyl;

$R^{5b}$ is selected from a group consisting of hydrogen, linear $C_1$-$C_6$ alkyl, and branched $C_1$-$C_6$ alkyl;

m is 0, 1, 2 or 3;

n is 1, 2, or 3.

In some embodiments $R^1$ is hydrogen.
In some embodiments $R^1$ is linear $C_1$-$C_6$ alkyl.
In some embodiments $R^1$ is branched $C_1$-$C_6$ alkyl.
In some embodiments $R^1$ is optionally substituted aryl.
In some embodiments $R^1$ is substituted aryl where $R^1$ is be substituted by 1 substituent.
In some embodiments $R^1$ is substituted aryl where $R^1$ is be substituted by 2 substituents.
In some embodiments $R^1$ is substituted aryl where $R^1$ is be substituted by 3 substituents.
In some embodiments $R^1$ is substituted aryl where $R^1$ is be substituted by 4 substituents.
In some embodiments $R^1$ is substituted aryl where $R^1$ is be substituted by 5 substituents.
In some embodiments $R^1$ is phenyl.
In some embodiments $R^2$ is optionally substituted aryl.
In some embodiments $R^2$ is substituted aryl where $R^2$ is be substituted by 1 substituent.
In some embodiments $R^2$ is substituted aryl where $R^2$ is be substituted by 2 substituents.
In some embodiments $R^2$ is substituted aryl where $R^2$ is be substituted by 3 substituents.
In some embodiments $R^2$ is substituted aryl where $R^2$ is be substituted by 4 substituents.
In some embodiments $R^2$ is substituted aryl where $R^2$ is be substituted by 5 substituents.
In some embodiments $R^2$ is phenyl.
In some embodiments $R^3$ is hydrogen.
In some embodiments $R^3$ is linear $C_1$-$C_6$ alkyl.
In some embodiments $R^3$ is branched $C_1$-$C_6$ alkyl.
In some embodiments $R^3$ is $C_3$-$C_7$ cycloalkyl.
In some embodiments $R^3$ is linear $C_1$-$C_6$ alkenyl.
In some embodiments $R^3$ is branched $C_1$-$C_6$ alkenyl.
In some embodiments $R^3$ is optionally substituted aryl.
In some embodiments $R^3$ is optionally substituted heteroaryl.

In some embodiments $R^3$ is

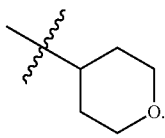 [SMILES: *C1CCOCC1]

In some embodiments $R^3$ is

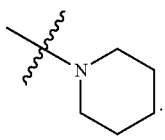

In some embodiments $R^3$ is

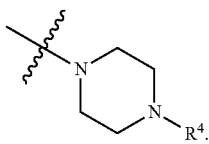

In some embodiments $R^3$ is

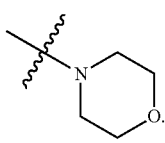 [SMILES: *N1CCOCC1]

In some embodiments $R^3$ is

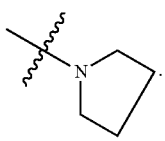 [SMILES: *N1CCCC1]

In some embodiments $R^3$ is

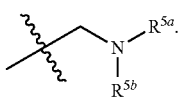

In some embodiments $R^3$ is

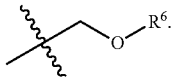

In some embodiments $R^3$ is
In some embodiments $R^4$ is hydrogen.
In some embodiments $R^4$ is linear $C_1$-$C_6$ alkyl.
In some embodiments $R^4$ is branched $C_1$-$C_6$ alkyl.
In some embodiments $R^{5a}$ is hydrogen.
In some embodiments $R^{5a}$ is linear $C_1$-$C_6$ alkyl.
In some embodiments $R^{5a}$ is branched $C_1$-$C_6$ alkyl.
In some embodiments $R^{5b}$ is hydrogen.
In some embodiments $R^{5b}$ is linear $C_1$-$C_6$ alkyl.
In some embodiments $R^{5b}$ is branched $C_1$-$C_6$ alkyl.
In some embodiments $R^6$ is hydrogen.
In some embodiments $R^6$ is linear $C_1$-$C_6$ alkyl.
In some embodiments $R^6$ is branched $C_1$-$C_6$ alkyl.
In some embodiments $R^6$ optionally substituted aryl.
In some embodiments m is 0.
In some embodiments m is 1.
In some embodiments m is 2.
In some embodiments m is 3.
In some embodiments n is 1.
In some embodiments n is 2.
In some embodiments n is 3.

Another particular embodiment of the invention comprises a compound of Formula (I), or pharmaceutically acceptable salt, solvate, prodrug or complex thereof, wherein $R^3$ is

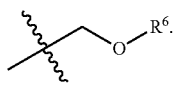

Another particular embodiment of the invention comprises a compound of Formula (I), or pharmaceutically acceptable salt, solvate, prodrug or complex thereof, wherein $R^3$ is

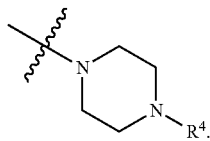

Another particular embodiment of the invention comprises a compound of Formula (I), or pharmaceutically acceptable salt, solvate, prodrug or complex thereof, wherein $R^3$ is

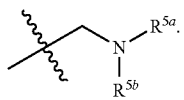

Another particular embodiment of the invention comprises a compound of Formula (I), or pharmaceutically acceptable salt, solvate, prodrug or complex thereof, wherein $R^3$ is selected from the group consisting of:

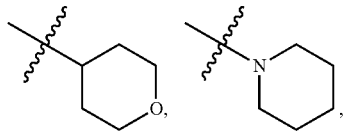

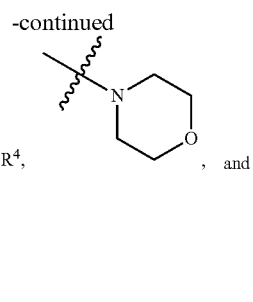

Another particular embodiment of the invention comprises a compound of Formula (I), or pharmaceutically acceptable salt, solvate, prodrug or complex thereof, wherein at least one of $R^1$ and $R^2$ is optionally substituted phenyl having 0-5 substituents.

Another particular embodiment of the invention comprises a compound of Formula (I), or pharmaceutically acceptable salt, solvate, prodrug or complex thereof, wherein at least one of $R^1$ and $R^2$ is phenyl.

Another particular embodiment of the invention comprises a compound of Formula (I), or pharmaceutically acceptable salt, solvate, prodrug or complex thereof, wherein m is 1 or 2; n is 1; and at least one of $R^1$ and $R^2$ is phenyl.

Another particular embodiment of the invention comprises a compound selected from the group consisting of:

5-(4-benzhydryl-piperazin-1-ylmethyl)-3-isopropyl-oxazolidin-2-one;
3-allyl-5-(4-benzhydryl-piperazin-1-ylmethyl)-oxazolidin-2-one;
5-(4-benzhydryl-piperazin-1-ylmethyl)-3-tert-butyl-oxazolidin-2-one;
5-(4-benzhydryl-piperazin-1-ylmethyl)-3-cyclopropyl-oxazolidin-2-one;
5-(4-benzhydryl-piperazin-1-ylmethyl)-3-cyclobutyl-oxazolidin-2-one;
5-(4-benzhydryl-piperazin-1-ylmethyl)-3-cyclopentyl-oxazolidin-2-one;
5-(4-benzhydryl-piperazin-1-ylmethyl)-3-cyclohexyl-oxazolidin-2-one;
5-((4-benzhydrylpiperazin-1-yl)methyl)-3-phenyloxazolidin-2-one;
5-(4-Benzhydryl-piperazin-1-ylmethyl)-3-cyclopentyl-oxazolidin-2-one;
5-((4-benzhydrylpiperazin-1-yl)methyl)-3-(4-fluorobenzyl)oxazolidin-2-one;
5-(4-Benzhydryl-piperazin-1-ylmethyl)-3-(tetrahydropyran-4-ylmethyl)-oxazolidin-2-one;
5-((4-benzhydrylpiperazin-1-yl)methyl)-3-(2-morpholinoethyl)oxazolidin-2-one;
5-(4-Benzhydryl-piperazin-1-ylmethyl)-3-propyl-oxazolidin-2-one;
5-(4-benzhydryl-piperazin-1-ylmethyl)-3-benzyl-oxazolidin-2-one;
5-((4-benzhydrylpiperazin-1-yl)methyl)-3-(4-fluorobenzyl)oxazolidin-2-one;
5-((4-benzhydrylpiperazin-1-yl)methyl)-3-(4-methylbenzyl)oxazolidin-2-one;
5-((4-benzhydrylpiperazin-1-yl)methyl)-3-(4-methoxybenzyl)oxazolidin-2-one;
5-((4-benzhydrylpiperazin-1-yl)methyl)-3-phenethyloxazolidin-2-one;
5-((4-benzhydrylpiperazin-1-yl)methyl)-3-(4-fluorophenethyl)oxazolidin-2-one;

5-(4-Benzhydryl-piperazin-1-ylmethyl)-3-(2-p-tolyl-ethyl)-oxazolidin-2-one;
5-(4-Benzhydryl-piperazin-1-ylmethyl)-3-[2-(4-methoxy-phenyl)-ethyl]-oxazolidin-2-one;
5-((4-benzhydrylpiperazin-1-yl)methyl)-3-(3-phenylpropyl)oxazolidin-2-one;
5-(4-Benzhydryl-piperazin-1-ylmethyl)-3-cyclopentyl-oxazolidin-2-one;
5-((4-benzhydrylpiperazin-1-yl)methyl)-3-(2-phenoxyethyl)oxazolidin-2-one;
5-((4-benzhydrylpiperazin-1-yl)methyl)-3-(cyclohexylmethyl)oxazolidin-2-one; and
pharmaceutically acceptable salts, solvates, prodrugs and complexes thereof.

Exemplary embodiments include compounds having the Formula (I) or a pharmaceutically acceptable salt form thereof:

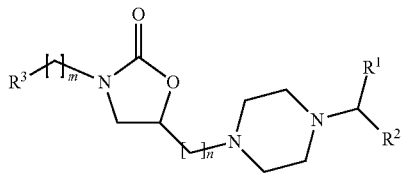

(I)

wherein non-limiting examples of $R^1$, $R^2$, $R^3$, m, and n are defined herein below in Table 1.

TABLE 1

Exemplary compounds of the Formula (I)

| Example | $R^1$ | $R^2$ | $R^3$ | m | n |
|---|---|---|---|---|---|
| 1 | Phenyl | Phenyl | Phenyl | 0 | 1 |
| 2 | Phenyl | Phenyl | 4-Flourophenyl | 0 | 1 |
| 3 | Phenyl | Phenyl | 4-Chlorophenyl | 0 | 1 |
| 4 | Phenyl | Phenyl | 4-Bromophenyl | 0 | 1 |
| 5 | Phenyl | Phenyl | 4-Triflouromethylphenyl | 0 | 1 |
| 6 | Phenyl | Phenyl | 4-Triflouromethoxyphenyl | 0 | 1 |
| 7 | Phenyl | Phenyl | 4-Methylphenyl | 0 | 1 |
| 8 | Phenyl | Phenyl | 4-Methoxyphenyl | 0 | 1 |
| 9 | Phenyl | Phenyl | Cyclohexyl | 0 | 1 |
| 10 | Phenyl | Phenyl | $CH(CH_3)_2$ | 0 | 1 |
| 11 | Phenyl | Phenyl | Cyclobutyl | 0 | 1 |
| 12 | Phenyl | Phenyl | Cyclopentyl | 0 | 1 |
| 13 | Phenyl | Phenyl | tert-butyl | 0 | 1 |
| 14 | Phenyl | Phenyl | Cyclopropyl | 0 | 1 |
| 15 | Phenyl | Phenyl | H | 0 | 1 |
| 16 | Phenyl | Phenyl | Methyl | 0 | 1 |
| 17 | Phenyl | Phenyl | Phenyl | 1 | 1 |
| 18 | Phenyl | Phenyl | 4-Flourophenyl | 1 | 1 |
| 19 | Phenyl | Phenyl | 4-Flourophenyl | 1 | 1 |
| 20 | Phenyl | Phenyl | 4-Chlorophenyl | 1 | 1 |
| 21 | Phenyl | Phenyl | 4-Bromophenyl | 1 | 1 |
| 22 | Phenyl | Phenyl | 4-Triflouromethylphenyl | 1 | 1 |
| 23 | Phenyl | Phenyl | 4-Triflouromethoxyphenyl | 1 | 1 |
| 24 | Phenyl | Phenyl | 4-Methoxyphenyl | 1 | 1 |
| 25 | Phenyl | Phenyl | 4-Methylphenyl | 1 | 1 |
| 26 | Phenyl | Phenyl | Cyclohexyl | 1 | 1 |
| 27 | Phenyl | Phenyl | $CH(CH_3)_2$ | 1 | 1 |
| 28 | Phenyl | Phenyl | Cyclobutyl | 1 | 1 |
| 29 | Phenyl | Phenyl | Cyclopentyl | 1 | 1 |
| 30 | Phenyl | Phenyl | tert-butyl | 1 | 1 |
| 31 | Phenyl | Phenyl | Cyclopropyl | 1 | 1 |
| 32 | Phenyl | Phenyl | H | 1 | 1 |
| 33 | Phenyl | Phenyl | Methyl | 1 | 1 |
| 34 | Phenyl | Phenyl | (vinyl group) | 1 | 1 |
| 35 | Phenyl | Phenyl | Ethyl | 1 | 1 |
| 36 | Phenyl | Phenyl | (tetrahydropyran-4-yl) | 1 | 1 |
| 37 | Phenyl | Phenyl | Phenyl | 2 | 1 |
| 38 | Phenyl | Phenyl | 4-Flourophenyl | 2 | 1 |
| 39 | Phenyl | Phenyl | 4-Chlorophenyl | 2 | 1 |
| 40 | Phenyl | Phenyl | 4-Bromophenyl | 2 | 1 |
| 41 | Phenyl | Phenyl | 4-Triflouromethylphenyl | 2 | 1 |
| 42 | Phenyl | Phenyl | 4-Triflouromethoxyphenyl | 2 | 1 |
| 43 | Phenyl | Phenyl | 4-Methoxyphenyl | 2 | 1 |
| 44 | Phenyl | Phenyl | 4-Methylphenyl | 2 | 1 |
| 45 | Phenyl | Phenyl | Cyclohexyl | 2 | 1 |
| 46 | Phenyl | Phenyl | $CH(CH_3)_2$ | 2 | 1 |
| 47 | Phenyl | Phenyl | Cyclobutyl | 2 | 1 |
| 48 | Phenyl | Phenyl | Cyclopentyl | 2 | 1 |
| 49 | Phenyl | Phenyl | tert-butyl | 2 | 1 |
| 50 | Phenyl | Phenyl | Cyclopropyl | 2 | 1 |
| 51 | Phenyl | Phenyl | (vinyl group) | 2 | 1 |
| 52 | Phenyl | Phenyl | Ethyl | 2 | 1 |
| 53 | Phenyl | Phenyl | (tetrahydropyran-4-yl) | 2 | 1 |
| 54 | Phenyl | Phenyl | (morpholin-4-yl) | 2 | 1 |
| 55 | Phenyl | Phenyl | (piperidin-1-yl) | 2 | 1 |
| 56 | Phenyl | Phenyl | (pyrrolidin-1-yl) | 2 | 1 |
| 57 | Phenyl | Phenyl | Phenyl | 3 | 1 |
| 58 | Phenyl | Phenyl | 4-Flourophenyl | 3 | 1 |
| 59 | Phenyl | Phenyl | 4-Chlorophenyl | 3 | 1 |
| 60 | Phenyl | Phenyl | 4-Bromophenyl | 3 | 1 |
| 61 | Phenyl | Phenyl | 4-Triflouromethylphenyl | 3 | 1 |
| 62 | Phenyl | Phenyl | 4-Triflouromethoxyphenyl | 3 | 1 |
| 63 | Phenyl | Phenyl | 4-Methoxyphenyl | 3 | 1 |
| 64 | Phenyl | Phenyl | 4-Methylphenyl | 3 | 1 |
| 65 | Phenyl | Phenyl | Cyclohexyl | 3 | 1 |
| 66 | Phenyl | Phenyl | $CH(CH_3)_2$ | 3 | 1 |
| 67 | Phenyl | Phenyl | Cyclobutyl | 3 | 1 |
| 68 | Phenyl | Phenyl | Cyclopentyl | 3 | 1 |
| 69 | Phenyl | Phenyl | tert-butyl | 3 | 1 |
| 70 | Phenyl | Phenyl | Cyclopropyl | 3 | 1 |

TABLE 1-continued

Exemplary compounds of the Formula (I)

| Example | R¹ | R² | R³ | m | n |
|---|---|---|---|---|---|
| 71 | Phenyl | Phenyl | 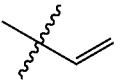 [SMILES: *C=C] | 3 | 1 |
| 72 | Phenyl | Phenyl | Ethyl | 3 | 1 |
| 73 | Phenyl | Phenyl | 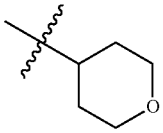 [SMILES: *C1CCOCC1] | 3 | 1 |
| 74 | Phenyl | Phenyl | 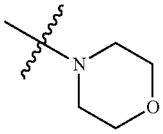 [SMILES: *N1CCOCC1] | 3 | 1 |
| 75 | Phenyl | Phenyl | 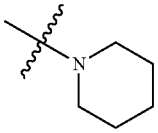 [SMILES: *N1CCCCC1] | 3 | 1 |
| 76 | Phenyl | Phenyl | 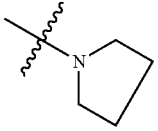 [SMILES: *N1CCCC1] | 3 | 1 |
| 77 | Phenyl | Phenyl | Phenyl | 1 | 2 |
| 78 | Phenyl | Phenyl | 4-Flourophenyl | 1 | 2 |
| 79 | Phenyl | Phenyl | 4-Flourophenyl | 1 | 2 |
| 80 | Phenyl | Phenyl | 4-Chlorophenyl | 1 | 2 |
| 81 | Phenyl | Phenyl | 4-Bromophenyl | 1 | 2 |
| 82 | Phenyl | Phenyl | 4-Triflouromethylphenyl | 1 | 2 |
| 83 | Phenyl | Phenyl | 4-Triflouromethoxyphenyl | 1 | 2 |
| 84 | Phenyl | Phenyl | 4-Methoxyphenyl | 1 | 2 |
| 85 | Phenyl | Phenyl | 4-Methylphenyl | 1 | 2 |
| 86 | Phenyl | Phenyl | Cyclohexyl | 1 | 2 |
| 87 | Phenyl | Phenyl | CH(CH₃)₂ | 1 | 2 |
| 88 | Phenyl | Phenyl | Cyclobutyl | 1 | 2 |
| 89 | Phenyl | Phenyl | Cyclopentyl | 1 | 2 |
| 90 | Phenyl | Phenyl | tert-butyl | 1 | 2 |
| 91 | Phenyl | Phenyl | Cyclopropyl | 1 | 2 |
| 92 | Phenyl | Phenyl | H | 1 | 2 |
| 93 | Phenyl | Phenyl | Methyl | 1 | 2 |
| 94 | Phenyl | Phenyl | 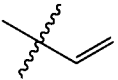 | 1 | 2 |
| 95 | Phenyl | Phenyl | Ethyl | 1 | 2 |
| 96 | Phenyl | Phenyl | 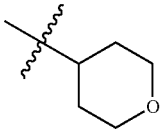 [SMILES: *C1CCOCC1] | 1 | 2 |
| 97 | Phenyl | Phenyl | Phenyl | 2 | 2 |
| 98 | Phenyl | Phenyl | 4-Flourophenyl | 2 | 2 |
| 99 | Phenyl | Phenyl | 4-Chlorophenyl | 2 | 2 |
| 100 | Phenyl | Phenyl | 4-Bromophenyl | 2 | 2 |
| 101 | Phenyl | Phenyl | 4-Triflouromethylphenyl | 2 | 2 |
| 102 | Phenyl | Phenyl | 4-Triflouromethoxyphenyl | 2 | 2 |
| 103 | Phenyl | Phenyl | 4-Methoxyphenyl | 2 | 2 |
| 104 | Phenyl | Phenyl | 4-Methylphenyl | 2 | 2 |
| 105 | Phenyl | Phenyl | Cyclohexyl | 2 | 2 |
| 106 | Phenyl | Phenyl | CH(CH₃)₂ | 2 | 2 |
| 107 | Phenyl | Phenyl | Cyclobutyl | 2 | 2 |
| 108 | Phenyl | Phenyl | Cyclopentyl | 2 | 2 |
| 109 | Phenyl | Phenyl | tert-butyl | 2 | 2 |
| 110 | Phenyl | Phenyl | Cyclopropyl | 2 | 2 |
| 111 | Phenyl | Phenyl | 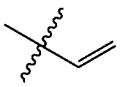 | 2 | 2 |
| 112 | Phenyl | Phenyl | Ethyl | 2 | 2 |
| 113 | Phenyl | Phenyl | 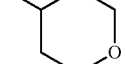 | 2 | 2 |
| 114 | Phenyl | Phenyl | 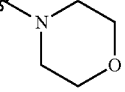 | 2 | 2 |
| 115 | Phenyl | Phenyl | 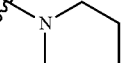 | 2 | 2 |
| 116 | Phenyl | Phenyl | 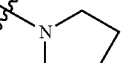 | 2 | 2 |
| 117 | Phenyl | Phenyl | Phenyl | 2 | 3 |
| 118 | Phenyl | Phenyl | 4-Flourophenyl | 2 | 3 |
| 119 | Phenyl | Phenyl | 4-Chlorophenyl | 2 | 3 |
| 119 | Phenyl | Phenyl | 4-Bromophenyl | 2 | 3 |
| 120 | Phenyl | Phenyl | 4-Triflouromethylphenyl | 2 | 3 |
| 121 | Phenyl | Phenyl | 4-Triflouromethoxyphenyl | 2 | 3 |
| 122 | Phenyl | Phenyl | 4-Methoxyphenyl | 2 | 3 |
| 123 | Phenyl | Phenyl | 4-Methylphenyl | 2 | 3 |
| 124 | Phenyl | Phenyl | Cyclohexyl | 2 | 3 |
| 125 | Phenyl | Phenyl | CH(CH₃)₂ | 2 | 3 |
| 126 | Phenyl | Phenyl | Cyclobutyl | 2 | 3 |
| 127 | Phenyl | Phenyl | Cyclopentyl | 2 | 3 |
| 128 | Phenyl | Phenyl | tert-butyl | 2 | 3 |
| 129 | Phenyl | Phenyl | Cyclopropyl | 2 | 3 |
| 130 | Phenyl | Phenyl | 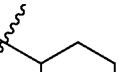 | 2 | 3 |
| 131 | Phenyl | Phenyl | Ethyl | 2 | 3 |
| 132 | Phenyl | Phenyl |  | 2 | 3 |

TABLE 1-continued

Exemplary compounds of the Formula (I)

| Example | R¹ | R² | R³ | m | n |
|---|---|---|---|---|---|
| 133 | Phenyl | Phenyl | morpholinyl | 2 | 3 |
| 134 | Phenyl | Phenyl | piperidinyl | 2 | 3 |
| 135 | Phenyl | Phenyl | pyrrolidinyl | 2 | 3 |
| 136 | Phenyl | Phenyl | Phenyl | 3 | 2 |
| 137 | Phenyl | Phenyl | 4-Flourophenyl | 3 | 2 |
| 138 | Phenyl | Phenyl | 4-Chlorophenyl | 3 | 2 |
| 139 | Phenyl | Phenyl | 4-Bromophenyl | 3 | 2 |
| 140 | Phenyl | Phenyl | 4-Triflouromethylphenyl | 3 | 2 |
| 141 | Phenyl | Phenyl | 4-Triflouromethoxyphenyl | 3 | 2 |
| 142 | Phenyl | Phenyl | 4-Methoxyphenyl | 3 | 2 |
| 143 | Phenyl | Phenyl | 4-Methylphenyl | 3 | 2 |
| 144 | Phenyl | Phenyl | Cyclohexyl | 3 | 2 |
| 145 | Phenyl | Phenyl | CH(CH₃)₂ | 3 | 2 |
| 146 | Phenyl | Phenyl | Cyclobutyl | 3 | 2 |
| 147 | Phenyl | Phenyl | Cyclopentyl | 3 | 2 |
| 148 | Phenyl | Phenyl | tert-butyl | 3 | 2 |
| 149 | Phenyl | Phenyl | Cyclopropyl | 3 | 2 |
| 150 | Phenyl | Phenyl | vinyl | 3 | 2 |
| 151 | Phenyl | Phenyl | Ethyl | 3 | 2 |
| 152 | Phenyl | Phenyl | tetrahydropyranyl | 3 | 2 |
| 153 | Phenyl | Phenyl | morpholinyl | 3 | 2 |
| 154 | Phenyl | Phenyl | piperidinyl | 3 | 2 |
| 155 | Phenyl | Phenyl | pyrrolidinyl | 3 | 2 |
| 156 | Phenyl | Phenyl | Phenyl | 3 | 3 |
| 157 | Phenyl | Phenyl | 4-Flourophenyl | 3 | 3 |
| 158 | Phenyl | Phenyl | 4-Chlorophenyl | 3 | 3 |
| 159 | Phenyl | Phenyl | 4-Bromophenyl | 3 | 3 |
| 160 | Phenyl | Phenyl | 4-Triflouromethylphenyl | 3 | 3 |
| 161 | Phenyl | Phenyl | 4-Triflouromethoxyphenyl | 3 | 3 |
| 162 | Phenyl | Phenyl | 4-Methoxyphenyl | 3 | 3 |
| 163 | Phenyl | Phenyl | 4-Methylphenyl | 3 | 3 |
| 164 | Phenyl | Phenyl | Cyclohexyl | 3 | 3 |
| 165 | Phenyl | Phenyl | CH(CH₃)₂ | 3 | 3 |
| 166 | Phenyl | Phenyl | Cyclobutyl | 3 | 3 |
| 167 | Phenyl | Phenyl | Cyclopentyl | 3 | 3 |
| 168 | Phenyl | Phenyl | tert-butyl | 3 | 3 |
| 169 | Phenyl | Phenyl | Cyclopropyl | 3 | 3 |
| 170 | Phenyl | Phenyl | vinyl | 3 | 3 |
| 171 | Phenyl | Phenyl | Ethyl | 3 | 3 |
| 172 | Phenyl | Phenyl | tetrahydropyranyl | 3 | 3 |
| 173 | Phenyl | Phenyl | morpholinyl | 3 | 3 |
| 174 | Phenyl | Phenyl | piperidinyl | 3 | 3 |
| 175 | Phenyl | Phenyl | pyrrolidinyl | 3 | 3 |

Exemplary embodiments of compounds of Formula (I) include compounds having the Formula (II) or a pharmaceutically acceptable salt form thereof:

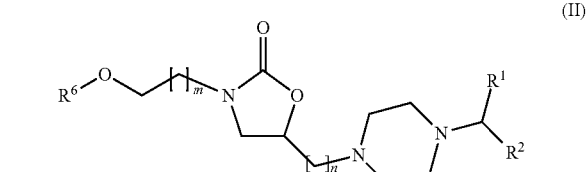

(II)

wherein non-limiting examples of $R^1$, $R^2$, $R^6$, m, and n are defined herein below in Table 2.

TABLE 2

Exemplary compounds of the Formula (II).

| Example | R¹ | R² | R⁶ | m | n |
|---|---|---|---|---|---|
| 176 | Phenyl | Phenyl | Phenyl | 1 | 1 |
| 177 | Phenyl | Phenyl | Methyl | 1 | 1 |
| 178 | Phenyl | Phenyl | Ethyl | 1 | 1 |
| 179 | Phenyl | Phenyl | n-Propyl | 1 | 1 |
| 180 | Phenyl | Phenyl | Isopropyl | 1 | 1 |
| 181 | Phenyl | Phenyl | tert-Butyl | 1 | 1 |
| 182 | Phenyl | Phenyl | Phenyl | 1 | 2 |
| 183 | Phenyl | Phenyl | Methyl | 1 | 2 |
| 184 | Phenyl | Phenyl | Ethyl | 1 | 2 |
| 185 | Phenyl | Phenyl | n-Propyl | 1 | 2 |
| 186 | Phenyl | Phenyl | Isopropyl | 1 | 2 |
| 187 | Phenyl | Phenyl | tert-Butyl | 1 | 2 |
| 188 | Phenyl | Phenyl | Phenyl | 1 | 3 |
| 189 | Phenyl | Phenyl | Methyl | 1 | 3 |
| 190 | Phenyl | Phenyl | Ethyl | 1 | 3 |
| 191 | Phenyl | Phenyl | n-Propyl | 1 | 3 |
| 192 | Phenyl | Phenyl | Isopropyl | 1 | 3 |
| 193 | Phenyl | Phenyl | tert-Butyl | 1 | 3 |
| 194 | Phenyl | Phenyl | Phenyl | 2 | 1 |
| 195 | Phenyl | Phenyl | Methyl | 2 | 1 |
| 196 | Phenyl | Phenyl | Ethyl | 2 | 1 |
| 197 | Phenyl | Phenyl | n-Propyl | 2 | 1 |
| 198 | Phenyl | Phenyl | Isopropyl | 2 | 1 |
| 199 | Phenyl | Phenyl | tert-Butyl | 2 | 1 |
| 200 | Phenyl | Phenyl | Phenyl | 2 | 2 |
| 201 | Phenyl | Phenyl | Methyl | 2 | 2 |
| 202 | Phenyl | Phenyl | Ethyl | 2 | 2 |
| 203 | Phenyl | Phenyl | n-Propyl | 2 | 2 |
| 204 | Phenyl | Phenyl | Isopropyl | 2 | 2 |
| 205 | Phenyl | Phenyl | tert-Butyl | 2 | 2 |
| 206 | Phenyl | Phenyl | Phenyl | 2 | 3 |
| 207 | Phenyl | Phenyl | Methyl | 2 | 3 |
| 208 | Phenyl | Phenyl | Ethyl | 2 | 3 |
| 209 | Phenyl | Phenyl | n-Propyl | 2 | 3 |
| 210 | Phenyl | Phenyl | Isopropyl | 2 | 3 |
| 211 | Phenyl | Phenyl | tert-Butyl | 2 | 3 |
| 212 | Phenyl | Phenyl | Phenyl | 3 | 3 |
| 213 | Phenyl | Phenyl | Methyl | 3 | 3 |
| 214 | Phenyl | Phenyl | Ethyl | 3 | 3 |
| 215 | Phenyl | Phenyl | n-Propyl | 3 | 3 |
| 216 | Phenyl | Phenyl | Isopropyl | 3 | 3 |
| 217 | Phenyl | Phenyl | tert-Butyl | 3 | 3 |

Exemplary embodiments of compounds of Formula (I) include compounds having the Formula (III) or pharmaceutically acceptable salt form thereof:

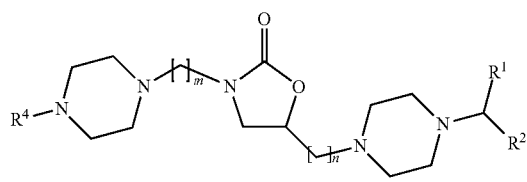

(III)

wherein non-limiting examples of R¹, R², R³, m, and n are defined herein below in Table 3.

TABLE 3

Exemplary compounds of the formula (III)

| Example | R¹ | R² | R⁴ | m | n |
|---|---|---|---|---|---|
| 218 | Phenyl | Phenyl | Hydrogen | 2 | 1 |
| 219 | Phenyl | Phenyl | Methyl | 2 | 1 |
| 220 | Phenyl | Phenyl | Ethyl | 2 | 1 |
| 221 | Phenyl | Phenyl | n-Propyl | 2 | 1 |

TABLE 3-continued

Exemplary compounds of the formula (III)

| Example | R¹ | R² | R⁴ | m | n |
|---|---|---|---|---|---|
| 222 | Phenyl | Phenyl | Isopropyl | 2 | 1 |
| 223 | Phenyl | Phenyl | tert-Butyl | 2 | 1 |
| 224 | Phenyl | Phenyl | Hydrogen | 2 | 2 |
| 225 | Phenyl | Phenyl | Methyl | 2 | 2 |
| 226 | Phenyl | Phenyl | Ethyl | 2 | 2 |
| 227 | Phenyl | Phenyl | n-Propyl | 2 | 2 |
| 228 | Phenyl | Phenyl | Isopropyl | 2 | 2 |
| 229 | Phenyl | Phenyl | tert-Butyl | 2 | 2 |
| 230 | Phenyl | Phenyl | Hydrogen | 2 | 3 |
| 231 | Phenyl | Phenyl | Methyl | 2 | 3 |
| 232 | Phenyl | Phenyl | Ethyl | 2 | 3 |
| 233 | Phenyl | Phenyl | n-Propyl | 2 | 3 |
| 234 | Phenyl | Phenyl | Isopropyl | 2 | 3 |
| 235 | Phenyl | Phenyl | tert-Butyl | 2 | 3 |
| 236 | Phenyl | Phenyl | Hydrogen | 3 | 2 |
| 237 | Phenyl | Phenyl | Methyl | 3 | 2 |
| 238 | Phenyl | Phenyl | Ethyl | 3 | 2 |
| 239 | Phenyl | Phenyl | n-Propyl | 3 | 2 |
| 240 | Phenyl | Phenyl | Isopropyl | 3 | 2 |
| 241 | Phenyl | Phenyl | tert-Butyl | 3 | 2 |
| 242 | Phenyl | Phenyl | Hydrogen | 3 | 3 |
| 243 | Phenyl | Phenyl | Methyl | 3 | 3 |
| 244 | Phenyl | Phenyl | Ethyl | 3 | 3 |
| 245 | Phenyl | Phenyl | n-Propyl | 3 | 3 |
| 246 | Phenyl | Phenyl | Isopropyl | 3 | 3 |
| 247 | Phenyl | Phenyl | tert-Butyl | 3 | 3 |

Exemplary embodiments of compounds of Formula (I) include compounds having the Formula (IV) or a pharmaceutically acceptable salt form thereof:

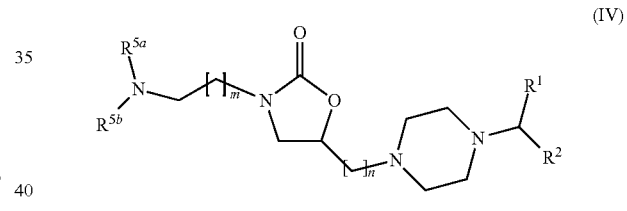

(IV)

wherein non-limiting examples of R¹, R², R⁵ᵃ, R⁵ᵇ, m, and n are defined herein below in Table 4.

TABLE 4

Exemplary compounds of the Formula (IV).

| Example | R¹ | R² | R⁵ᵃ | R⁵ᵇ | m | n |
|---|---|---|---|---|---|---|
| 248 | Phenyl | Phenyl | Hydrogen | Hydrogen | 1 | 1 |
| 249 | Phenyl | Phenyl | Methyl | Hydrogen | 1 | 1 |
| 250 | Phenyl | Phenyl | Ethyl | Hydrogen | 1 | 1 |
| 251 | Phenyl | Phenyl | n-Propyl | Hydrogen | 1 | 1 |
| 252 | Phenyl | Phenyl | Isopropyl | Hydrogen | 1 | 1 |
| 253 | Phenyl | Phenyl | tert-Butyl | Hydrogen | 1 | 1 |
| 254 | Phenyl | Phenyl | Methyl | Methyl | 1 | 1 |
| 255 | Phenyl | Phenyl | Ethyl | Ethyl | 1 | 1 |
| 256 | Phenyl | Phenyl | n-Propyl | n-Propyl | 1 | 1 |
| 257 | Phenyl | Phenyl | Isopropyl | Isopropyl | 1 | 1 |
| 258 | Phenyl | Phenyl | Hydrogen | Hydrogen | 1 | 2 |
| 259 | Phenyl | Phenyl | Methyl | Hydrogen | 1 | 2 |
| 260 | Phenyl | Phenyl | Ethyl | Hydrogen | 1 | 2 |
| 261 | Phenyl | Phenyl | n-Propyl | Hydrogen | 1 | 2 |
| 262 | Phenyl | Phenyl | Isopropyl | Hydrogen | 1 | 2 |
| 263 | Phenyl | Phenyl | tert-Butyl | Hydrogen | 1 | 2 |
| 264 | Phenyl | Phenyl | Methyl | Methyl | 1 | 2 |
| 265 | Phenyl | Phenyl | Ethyl | Ethyl | 1 | 2 |
| 266 | Phenyl | Phenyl | n-Propyl | n-Propyl | 1 | 2 |
| 267 | Phenyl | Phenyl | Isopropyl | Isopropyl | 1 | 2 |
| 268 | Phenyl | Phenyl | Hydrogen | Hydrogen | 1 | 3 |

TABLE 4-continued

Exemplary compounds of the Formula (IV).

| Example | R$^1$ | R$^2$ | R$^{5a}$ | R$^{5b}$ | m | n |
|---|---|---|---|---|---|---|
| 269 | Phenyl | Phenyl | Methyl | Hydrogen | 1 | 3 |
| 270 | Phenyl | Phenyl | Ethyl | Hydrogen | 1 | 3 |
| 271 | Phenyl | Phenyl | n-Propyl | Hydrogen | 1 | 3 |
| 272 | Phenyl | Phenyl | Isopropyl | Hydrogen | 1 | 3 |
| 273 | Phenyl | Phenyl | tert-Butyl | Hydrogen | 1 | 3 |
| 274 | Phenyl | Phenyl | Methyl | Methyl | 1 | 3 |
| 275 | Phenyl | Phenyl | Ethyl | Ethyl | 1 | 3 |
| 276 | Phenyl | Phenyl | n-Propyl | n-Propyl | 1 | 3 |
| 277 | Phenyl | Phenyl | Isopropyl | Isopropyl | 1 | 3 |
| 278 | Phenyl | Phenyl | Hydrogen | Hydrogen | 2 | 2 |
| 279 | Phenyl | Phenyl | Methyl | Hydrogen | 2 | 2 |
| 280 | Phenyl | Phenyl | Ethyl | Hydrogen | 2 | 2 |
| 281 | Phenyl | Phenyl | n-Propyl | Hydrogen | 2 | 2 |
| 282 | Phenyl | Phenyl | Isopropyl | Hydrogen | 2 | 2 |
| 283 | Phenyl | Phenyl | tert-Butyl | Hydrogen | 2 | 2 |
| 284 | Phenyl | Phenyl | Methyl | Methyl | 2 | 2 |
| 285 | Phenyl | Phenyl | Ethyl | Ethyl | 2 | 2 |
| 286 | Phenyl | Phenyl | n-Propyl | n-Propyl | 2 | 2 |
| 287 | Phenyl | Phenyl | Isopropyl | Isopropyl | 2 | 2 |
| 288 | Phenyl | Phenyl | Hydrogen | Hydrogen | 2 | 3 |
| 289 | Phenyl | Phenyl | Methyl | Hydrogen | 2 | 3 |
| 290 | Phenyl | Phenyl | Ethyl | Hydrogen | 2 | 3 |
| 291 | Phenyl | Phenyl | n-Propyl | Hydrogen | 2 | 3 |
| 292 | Phenyl | Phenyl | Isopropyl | Hydrogen | 2 | 3 |
| 293 | Phenyl | Phenyl | tert-Butyl | Hydrogen | 2 | 3 |
| 294 | Phenyl | Phenyl | Methyl | Methyl | 2 | 3 |
| 295 | Phenyl | Phenyl | Ethyl | Ethyl | 2 | 3 |
| 296 | Phenyl | Phenyl | n-Propyl | n-Propyl | 2 | 3 |
| 297 | Phenyl | Phenyl | Isopropyl | Isopropyl | 2 | 3 |

For the purposes of demonstrating the manner in which the compounds of the present invention are named and referred to herein, the compound having the formula:

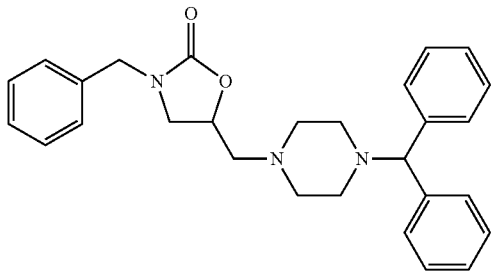 [SMILES: O=C1OC(CN2CCN(C(c3ccccc3)c3ccccc3)CC2)CN1Cc1ccccc1]

has the chemical name 5-(4-Benzhydryl-piperazin-1-ylmethyl)-3-benzyl-oxazolidin-2-one.

For the purposes of the present invention, a compound depicted by the racemic formula, for example:

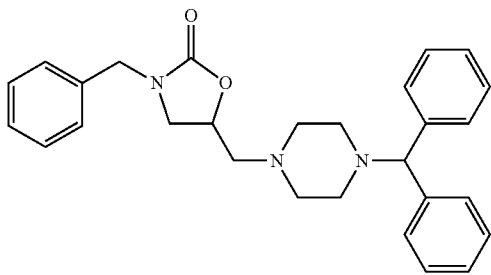 [SMILES: O=C1OC(CN2CCN(C(c3ccccc3)c3ccccc3)CC2)CN1Cc1ccccc1]

will stand equally well for either of the two enantiomers having the formula:

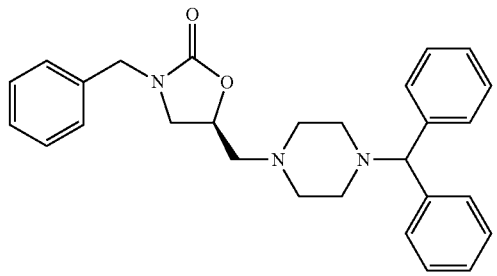 [SMILES: O=C1O[C@@H](CN2CCN(C(c3ccccc3)c3ccccc3)CC2)CN1Cc1ccccc1]

or the formula:

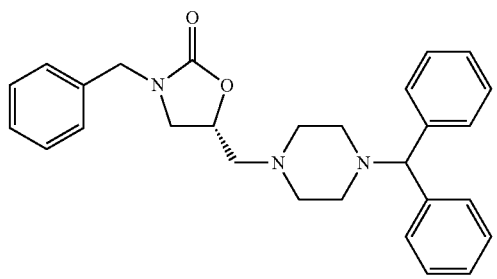 [SMILES: O=C1O[C@H](CN2CCN(C(c3ccccc3)c3ccccc3)CC2)CN1Cc1ccccc1]

or mixtures thereof, or in the case where a second chiral center is present, all diastereomers.

In all of the embodiments provided herein, examples of suitable optional substituents are not intended to limit the scope of the claimed invention. The compounds of the invention may contain any of the substituents, or combinations of substituents, provided herein.

Process

The present invention further relates to a process for preparing the 5-hydroxytryptamine receptor 2b activity modulators of the present invention.

Compounds of the present teachings can be prepared in accordance with the procedures outlined herein, from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions can vary with the particular reactants or solvent used, but such conditions can be determined by one skilled in the art by routine optimization procedures. Those skilled in the art of organic synthesis will recognize that the nature and order of the synthetic steps presented can be varied for the purpose of optimizing the formation of the compounds described herein.

The processes described herein can be monitored according to any suitable method known in the art. For example, product formation can be monitored by spectroscopic means, such as nuclear magnetic resonance spectroscopy (e.g., $^1$H or $^{13}$C), infrared spectroscopy, spectrophotometry (e.g., UV-visible), mass spectrometry, or by chromatography such as high pressure liquid chromatograpy (HPLC), gas chromatography (GC), gel-permeation chromatography (GPC), or thin layer chromatography (TLC).

Preparation of the compounds can involve protection and deprotection of various chemical groups. The need for protection and deprotection and the selection of appropriate protecting groups can be readily determined by one skilled in the art. The chemistry of protecting groups can be found, for example, in Greene et al., *Protective Groups in Organic Synthesis,* 2d. Ed. (Wiley & Sons, 1991), the entire disclosure of which is incorporated by reference herein for all purposes.

The reactions or the processes described herein can be carried out in suitable solvents which can be readily selected by one skilled in the art of organic synthesis. Suitable solvents typically are substantially nonreactive with the reactants, intermediates, and/or products at the temperatures at which the reactions are carried out, i.e., temperatures that can range from the solvent's freezing temperature to the solvent's boiling temperature. A given reaction can be carried out in one solvent or a mixture of more than one solvent. Depending on the particular reaction step, suitable solvents for a particular reaction step can be selected.

The compounds of these teachings can be prepared by methods known in the art of organic chemistry. The reagents used in the preparation of the compounds of these teachings can be either commercially obtained or can be prepared by standard procedures described in the literature. For example, compounds of the present invention can be prepared according to the method illustrated in the following General Synthetic Schemes.

General Synthetic Schemes for Preparation of Compounds

The reagents used in the preparation of the compounds of this invention can be either commercially obtained or can be prepared by standard procedures described in the literature. In accordance with this invention, compounds in the genus may be produced by one of the following reaction schemes.

Compounds of the disclosure may be prepared according to the process outlined in Scheme 1.

Scheme 1

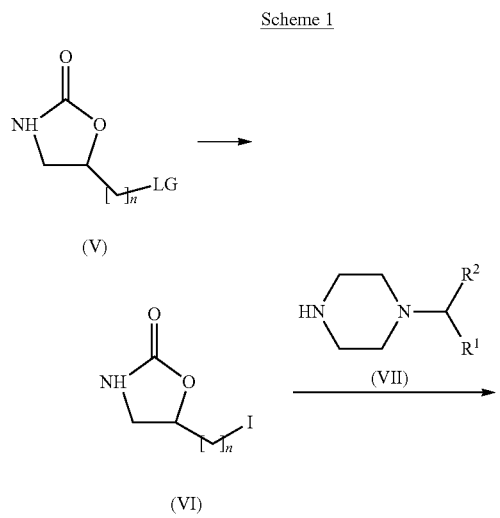

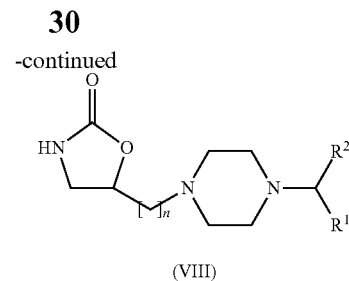

A suitably substituted compound of formula (V), a known compound or compound prepared by known methods, wherein LG is a suitable leaving group such as chlorine, bromine, mesylate and the like, is reacted with an iodide salt such as sodium iodide, potassium iodide, cesium iodide, or tetrabutyl ammonium iodide and the like, in an organic solvent such as acetone, tetrahydrofuran, 1,4-dioxane, methanol, ethanol, butanone, N,N-dimethylformamide, isopropanol, and the like, optionally heated, optionally heated with microwave irradiation, to provide a compound of the formula (VI). A compound of the formula (VI) is then reacted with a compound of the formula (VII), known compound or compound prepared by known methods, in the presence of a base such as triethylamine, diisopropylethyl amine, pyridine, 2,6-lutidine, and the like, in an organic solvent such as tetrahydrofuran, 1,4-dioxane, methanol, ethanol, N,N-dimethylformamide, isopropanol, and the like, optionally heated, optionally heated with microwave irradiation, to provide a compound of the formula (VIII).

Compounds of formula (XIV) may be prepared according to the process outlined in Scheme 2.

Scheme 2

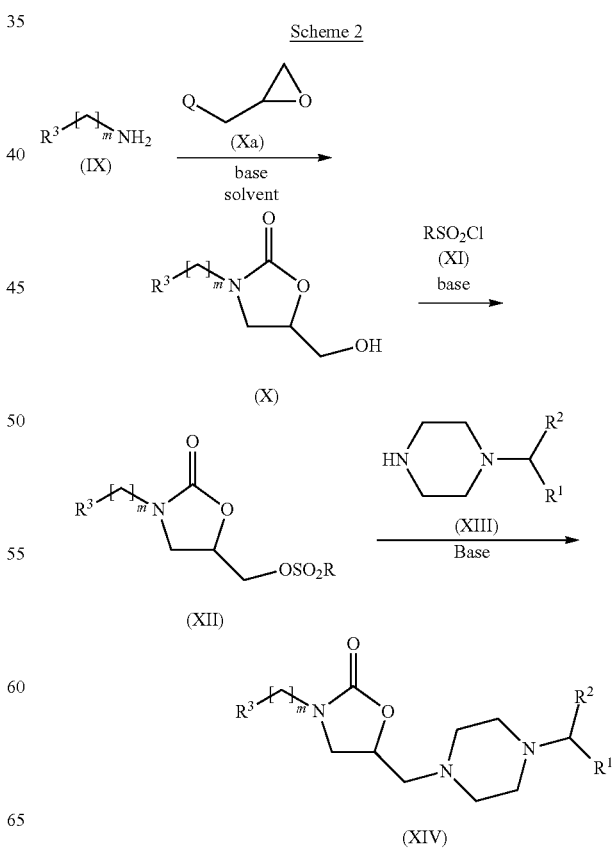

A suitably substituted compound of formula (IX)), a known compound or compound prepared by known methods, is reacted with a compound of the formula (Xa) wherein Q is a leaving group such as bromine, chlorine, mesylate, and the like, in the presence of a base such as potassium carbonate, sodium carbonate, cesium carbonate, lithium carbonate, silver carbonate and the like, in an organic solvent such as methanol, ethanol, isopropanol, N,N-dimethylformamide, tetrahydrofuran, 1,4-dioxane and the like to provide a compound of the formula (X). A compound of the formula (X) is then reacted with a sulfonyl chloride of the formula (XI) such as methanesulfonyl chloride, toluenesulfonyl chloride and the like, in the presence of a base such as triethylamine, diisopropylethyl amine, pyridine, 2,6-lutidine, and the like, in an organic solvent such as methylene chloride, dichloroethane, tetrahydrofuran, 1,4-dioxane N,N-dimethylformamide, and the like to provide a compound of the formula (XII). A compound of the formula (XII) is then reacted with a compound of the formula (XIII), known compound or compound prepared by known methods, in the presence of a base such as triethylamine, diisopropylethyl amine, pyridine, 2,6-lutidine, and the like, in an organic solvent such as tetrahydrofuran, 1,4-dioxane, methanol, ethanol, N,N-dimethylformamide, isopropanol, and the like, optionally heated, optionally heated with microwave irradiation, to provide a compound of the formula (XIV).

Compounds of formula (XXI) may be prepared according to the process outlined in Scheme 3.

such as hydrogen chloride, trifluoroacetic acid, and the like in organic solvent such as 1,4-dioxane, tetrahydrofuran, dichloromethane, and the like, or 2) with hydrogen in the presence of a catalyst such as palladium on activated carbon, platinum oxide, and the like in an organic solvent such as ethyl acetate, methanol, ethanol and the like; or 3) with base such as sodium hydroxide, potassium carbonate and the like in a solvent such as water, methanol, tetrahydrofuran and the like to provide compounds of the formula (XVIII). Alternatively, a compound of the formula (XIX), a known compound or compound prepared by known methods, is reacted with a compound of the formula (XVI), wherein LG at each occurrence is independently a leaving group such as chlorine, imidazole, methoxy, ethoxy, phenoxy or p-nitro-phenol, in the presence of a base such as triethylamine, diisopropylethyl amine, pyridine, and the like, in a solvent such as methylene chloride, dichloroethane, tetrahydrofuran, 1,4-dioxane, N,N-dimethylformamide, and the like to provide a compound of the formula (XVIII).

A compound of the formula (XVIII) is then converted to a compound of the formula (XX), wherein X is a mesylate, tosylate, nosylate, and the like, using methods that are known to one skilled in the art. Thus, a compound of the formula (XVIII) is reacted with a sulfonyl chloride such as methanesulfonyl chloride, toluenesulfonyl chloride p-nitrophenyl sulfonyl chloride, and the like, in the presence of a base such as triethylamine, diisopropylethyl amine, pyridine, 2,6-lutidine, and the like, in an organic solvent such as

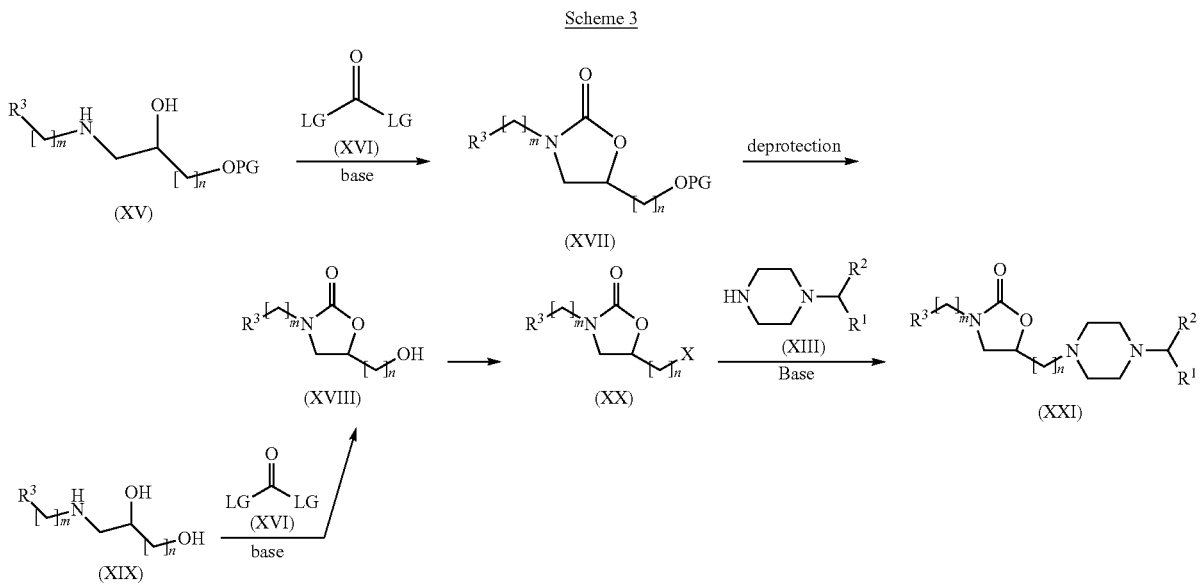

Scheme 3

A suitably substituted compound of formula (XV), a known compound or compound prepared by known methods, wherein PG is a suitable protecting group, is reacted with a compound of the formula (XVI), wherein LG at each occurrence is independently a leaving group such as chlorine, imidazole, methoxy, ethoxy, phenoxy, or p-nitro-phenol, in the presence of a base such as triethylamine, diisopropylethyl amine, pyridine, and the like, in a solvent such as methylene chloride, dichloroethane, tetrahydrofuran, 1,4-dioxane, N,N-dimethylformamide, and the like to provide a compound of the formula (XVII). The protecting group of compounds of the formula (XVII) can be removed by treatment under suitable conditions such as 1) with acid, methylene chloride, dichloroethane, tetrahydrofuran, 1,4-dioxane, N,N-dimethylformamide, and the like to provide a compound of the formula (XX). A compound of the formula (XX) is then reacted with a compound of the formula (XIII), known compound or compound prepared by known methods, in the presence of a base such as triethylamine, diisopropylethyl amine, pyridine, 2,6-lutidine, and the like, in an organic solvent such as tetrahydrofuran, 1,4-dioxane, methanol, ethanol, N,N-dimethylformamide, isopropanol, and the like, optionally heated, optionally heated with microwave irradiation, to provide a compound of the formula (XXI).

Compounds of formula (XXVIII) may be prepared according to the process outlined in Scheme 4.

Scheme 4.

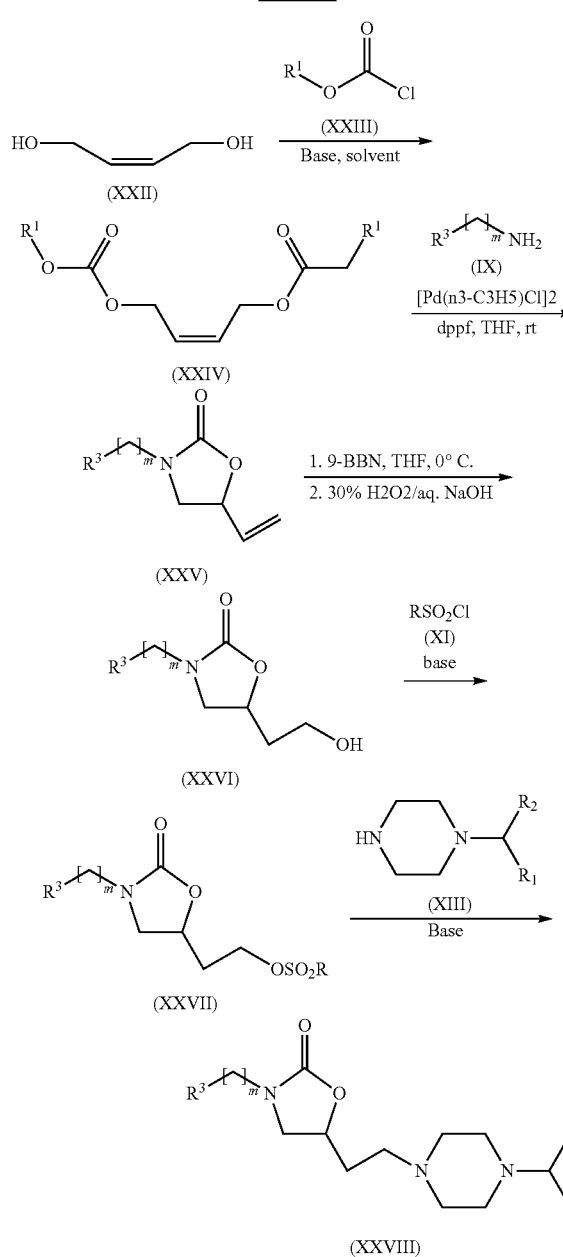

A compound of the formula (XXII), a known compound or compound prepared by known methods, is reacted with a compound of the formula (XXIII), such as methyl chloroformate, ethyl chloroformate, propyl chloroformate and the like, in the presence of a base such as triethylamine, diisopropylethyl amine, pyridine, 2,6-lutidine, and the like, in an organic solvent such as tetrahydrofuran, 1,4-dioxane, methylene chloride, 1,2-dichloroethane, chloroform, and the like to provide a compound of the formula (XXIV). A compound of the formula (XXIV) is then reacted with a compounds of the formula (IX) in the presence of a suitable catalyst such as Pd($\eta^3$-C$_3$H$_5$)Cl]$_2$ tris(dibenzylideneacetone)dipalladium (0), tetrakis(triphenylphosphine)palladium(0), bis(triphenylphosphine)palladium(II) dichloride, palladium(II) acetate, palladium (II) acetylacetonate, palladium on carbon, platinum(II) chloride, platinum(II) acetylacetonate, bis(triphenylphosphine)palladium(II)dichloride, dichlorotris(triphenylphosphine) ruthenium(II), and the like, and in the presences of a suitable ligand such as triphenylphosphine, 1,1'-bis(diphenylphosphino)ferrocene, 1,2-Bis(diphenylphosphino)ethane, 1,4-Bis(diphenylphosphino) butane, 2,2'-bis(diphenylphosphino)-1,1'-binaphthyl, tri(-2-furyl)phosphine, tri(4-trifluoromethylphenyl)phosphine, tri(4-methoxyphenyl)phosphine, tri(3-methoxyphenyl) phosphine and the like in an organic solvent such as tetrahydrofuran, 1,4-dioxane, methylene chloride, 1,2-dichloroethane, chloroform, dimethylformamide, and the like to provide a compound of the formula (XXV). A compound of the formula (XXV) is then converted to a compound of the formula (XXVI) by sequential treatment with 1) a hydroborating reagent such as borane, 9-borabicyclo[3.3.1]nonane, and the like, in an organic solvent such as tetrahydrofuran, 1,4-dioxane, N,N-dimethylformamide and the like, followed by 2) an oxidant such as hydrogen peroxide, meta-chloroperbenzoic acid, and the like in the presence of a base such as sodium hydroxide, lithium hydroxide, potassium hydroxide, and the like in a solvent such as methanol, ethanol, water, tetrahydrofuran, 1,4-dioxane, N,N-dimethylformamide and the like. A compound of the formula (XXVI) is then is then reacted with a sulfonyl chloride of the formula (XI) such as methanesulfonyl chloride, toluenesulfonyl chloride and the like, in the presence of a base such as triethylamine, diisopropylethyl amine, pyridine, 2,6-lutidine, and the like, in an organic solvent such as methylene chloride, dichloroethane, tetrahydrofuran, 1,4-dioxane, N,N-dimethylformamide, and the like to provide a compound of the formula (XXVII). A compound of the formula (XXVII) is then reacted with a compound of the formula (XIII), known compound or compound prepared by known methods, in the presence of a base such as triethylamine, diisopropylethyl amine, pyridine, 2,6-lutidine, and the like, in an organic solvent such as tetrahydrofuran, 1,4-dioxane, methanol, ethanol, N,N-dimethylformamide, isopropanol, and the like, optionally heated, optionally heated with microwave irradiation, to provide a compound of the formula (XXI).

Examples

The practice of the invention is illustrated by the following non-limiting examples. The Examples provided below provide representative methods for preparing exemplary compounds of the present invention. The skilled practitioner will know how to substitute the appropriate reagents, starting materials and purification methods known to those skilled in the art, in order to prepare the compounds of the present invention.

In the examples that follow, $^1$H-NMR spectra were obtained on a Varian Mercury 300-MHz NMR. Purity (%) and mass spectral data were determined with a Waters Alliance 2695 HPLC/MS (Waters Symmetry C18, 4.6×75 mm, 3.5 μm) with a 2996 diode array detector from 210-400 nm.

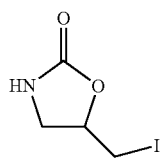

Preparation of 5-Iodomethyl-oxazolidin-2-one: Sodium iodide (13.19 g, 88.52 mmol) in acetone (35 mL) was added to a round bottom flasks containing 5-Chloromethyl-oxazolidin-2-one (0.8 g, 5.90 mmol) and the mixture was refluxed for 48 hours. The reaction was later quenched with water and extracted with ether. The organic layer was washed with water, brine and dried over MgSO₄ to obtain the product as a light yellow solids that was utilized for the next step without purification.

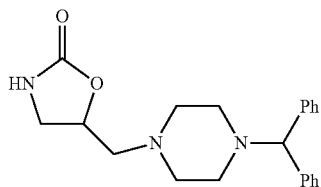 [SMILES: O=C1NCC(CN2CCN(C(c3ccccc3)c3ccccc3)CC2)O1]

Preparation of 5-(4-Benzhydryl-piperazin-1-ylmethyl)-oxazolidin-2-one: 5-Iodomethyl-oxazolidin-2-one (0.729 g, 3.21 mmol) and the diphenylmethylpiperazine (2.43 g, 9.629 mmol) containing triethyl amine (1.299 g, 12.83 mmol) in anhydrous tetrahydrofuran (40 mL) was stirred at reflux under a nitrogen atmosphere for 48 hours. The mixture was filtered (when appropriate), concentrated under reduced pressure and the residue was dissolved in dichloromethane and purified by flash silica gel chromatography using methanol (0-10%) in dichloromethane and reverse phase chromatography using acetonitrile: water (0-100%) to obtain colorless solid (0.203 g, 17.99%). $^1$H-NMR {CDCl₃, 400 MHz, δ (ppm)} 2.32-2.52 (m, 8H), 2.59-2.64 (m, 1H), 3.21 (t, 1H), 3.50 (t, 1H), 4.13 (s, 1H), 4.61-4.68 (m, 1H), 6.08 (s, 1H), 7.06-7.10 (m, 2H), 7.16-7.19 (m, 4H), 7.31-7.33 (m, 4H). LC-MS (ESI) (m/z) 352.2 (M+1)⁺.

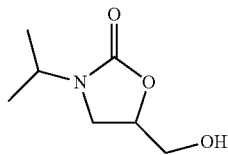

Preparation of 5-Hydroxymethyl-3-isopropyl-oxazolidin-2-one: To a suspension of K₂CO₃ (4 g, 28.94 mmol) in anhydrous methanol (30 mL) containing epibromohydrin (3.4214 g, 57.88 mmol) was added the isopropyl amine (7.92 g, 57.81 mmol) and the reaction was stirred overnight. The reaction mixture was later filtered and the organic solvent was stripped off under reduced pressure to obtain a liquid residue. It was chromatographed on silica gel using methanol (0-2%) in dichloromethane to obtain the colorless solid product (3.54 g, 38.42% yield). $^1$H-NMR {CDCl₃, 400 MHz, δ (ppm)} 1.10-1.12 (m, 6H), 3.32-3.36 (m, 1H), 3.41-3.47 (m, 1H), 3.56-3.60 (m, 1H), 3.78-3.81 (m, 1H), 3.95-4.07 (septet, 1H), 4.49-4.54 (m, 1H).

The following compounds can be prepared by the procedure of 5-hydroxymethyl-3-isopropyl-oxazolidin-2-one. The skilled practitioner will know how to substitute the appropriate reagents, starting materials and purification methods known to those skilled in the art, in order to prepare the compounds provided herein.

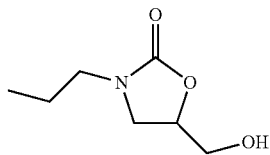

Preparation of 5-(Hydroxymethyl)-3-propyloxazolidin-2-one: The title compound was prepared according to the procedure for 5-hydroxymethyl-3-isopropyl-oxazolidin-2-one, except n-propyl amine was substituted for isopropyl amine. $^1$H-NMR {CDCl₃, 400 MHz, δ (ppm)} 0.93 (t, 3H), 1.54-1.63 (sextet, 2H), 3.01 (s, 1H), 3.20-3.24 (m, 2H), 3.45-3.49 (m, 1H), 3.57 (t, 1H), 3.63-3.67 (m, 1H), 3.86-3.90 (m, 1H), 4.57-4.63 (m, 1H).

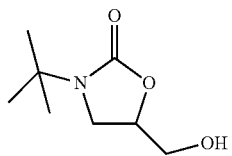

Preparation of 3-tert-butyl-5-hydroxymethyl-oxazolidin-2-one: The title compound was prepared according to the procedure for 5-hydroxymethyl-3-isopropyl-oxazolidin-2-one, except 3-tert-butyl amine was substituted for isopropyl amine: $^1$H-NMR {CDCl₃, 400 MHz, δ (ppm)} 1.39 (s, 9H), 2.46 (t, 1H), 3.48-3.53 (m, 1H), 3.60-3.66 (m, 2H), 3.82-3.87 (m, 2H), 4.45-4.49 (m, 1H).

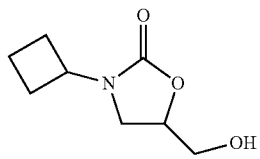 [SMILES: O=C1OC(CO)CN1C1CCC1]

Preparation of 3-cyclobutyl-5-hydroxymethyl-oxazolidin-2-one: The title compound was prepared according to the procedure for 5-hydroxymethyl-3-isopropyl-oxazolidin-2-one, except cyclobutyl amine was substituted for isopropyl amine. $^1$H-NMR {CDCl₃, 400 MHz, δ (ppm)} 1.64-1.72 (m, 2H), 2.12-2.19 (m, 4H), 2.79 (t, 1H), 3.50-3.54 (dd, 8.4 Hz, 2H), 3.61-3.69 (m, 2H), 3.84-3.89 (m, 1H), 4.32-4.40 (pentet, 1H), 4.56-4.62 (m, 1H).

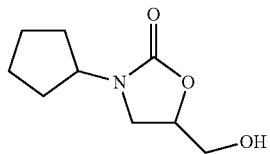 [SMILES: O=C1OC(CO)CN1C1CCCC1]

Preparation of 3-cyclopentyl-5-hydroxymethyl-oxazolidin-2-one: The title compound was prepared according to the procedure for 5-hydroxymethyl-3-isopropyl-oxazolidin-2-one, except cyclopentyl amine was substituted for isopropyl amine. $^1$H-NMR {CDCl₃, 400 MHz, δ (ppm)} 0.92 (d, 6H), 1.84-1.95 (septet, 1H), 3.05 (d, 2H), 3.14 (t, 1H), 3.47-3.49 (m, 1H), 3.57 (t, 1H), 3.61-3.67 (m, 1H), 3.85-3.90 (m, 1H), 4.57-4.62 (m, 1H).

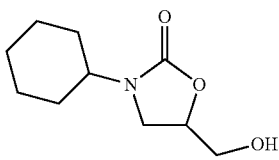 [SMILES: O=C1OC(CO)CN1C1CCCCC1]

Preparation of 3-cyclohexyl-5-hydroxymethyl-oxazolidin-2-one: The title compound was prepared according to the procedure for 5-hydroxymethyl-3-isopropyl-oxazolidin-2-one, except cyclohexyl amine was substituted for isopropyl amine. $^1$H-NMR {CDCl$_3$, 400 MHz, δ (ppm)} 0.89-1.01 (m, 1H), 1.11-1.30 (m, 4H), 1.44-1.68 (m, 5H), 3.20-3.24 (m, 1H), 3.32-3.43 (m, 3H), 3.50-3.54 (m, 1H), 4.33-4.39 (m, 1H).

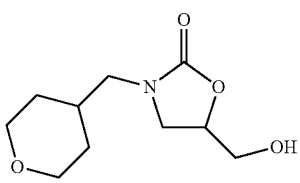 [SMILES: O=C1OC(CO)CN1CC1CCOCC1]

Preparation of 5-Hydroxymethyl-3-(tetrahydro-pyran-4-ylmethyl)-oxazolidin-2-one The title compound was prepared according to the procedure for 5-hydroxymethyl-3-isopropyl-oxazolidin-2-one, except (tetrahydro-2H-pyran-4-yl)methanamine was substituted for isopropyl amine. $^1$H-NMR {CDCl$_3$, 400 MHz, δ (ppm)} 1.29-1.39 (m, 2H), 1.58-1.62 (m, 2H), 1.81-1.92 (m, 1H), 3.08-3.16 (m, 2H), 3.23 (t, 1H), 3.34-3.40 (m, 2H), 3.50-3.65 (m, 3H), 3.86-3.91 (m, 1H), 3.95-3.99 (m, 2H), 4.56-4.62 (m, 1H).

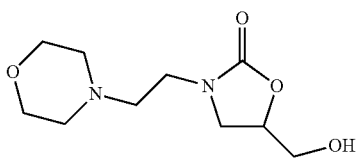 [SMILES: O=C1OC(CO)CN1CCN1CCOCC1]

Preparation of 5-Hydroxymethyl-3-(2-morpholin-4-yl-ethyl)-oxazolidin-2-one: The title compound was prepared according to the procedure for 5-hydroxymethyl-3-isopropyl-oxazolidin-2-one, except 2-morpholinoethylamine was substituted for isopropyl amine. $^1$H-NMR {CDCl$_3$, 400 MHz, δ (ppm)} 2.44-2.64 (m, 7H), 3.28-3.34 (m, 1H), 3.50-3.57 (m, 2H), 3.66-3.74 (m, 6H), 3.88-3.92 (m, 1H), 4.59-4.65 (m, 1H).

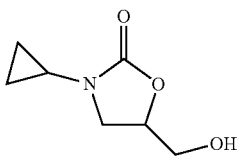 [SMILES: O=C1OC(CO)CN1C1CC1]

Preparation of 3-cyclopropyl-5-hydroxymethyl-oxazolidin-2-one: The title compound was prepared according to the procedure for 5-hydroxymethyl-3-isopropyl-oxazolidin-2-one, except cyclopropyl amine was substituted for isopropyl amine. $^1$H-NMR {CDCl$_3$, 400 MHz, δ (ppm)} 0.69-0.84 (m, 4H), 2.51-2.57 (m, 1H), 2.71 (t, 1H), 3.44-3.48 (dd, 8.6 Hz, 1H), 3.55 (t, 1H), 3.61-3.66 (m, 1H), 3.83-3.88 (m, 1H), 4.51-4.55 (m, 1H).

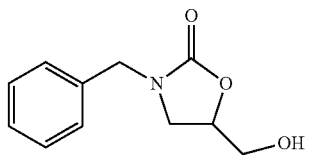 [SMILES: O=C1OC(CO)CN1Cc1ccccc1]

Preparation of 3-Benzyl-5-hydroxymethyl-oxazolidin-2-one: The title compound was prepared according to the procedure for 5-hydroxymethyl-3-isopropyl-oxazolidin-2-one, except benzyl amine was substituted for isopropyl amine. $^1$H-NMR {CDCl$_3$, 400 MHz, δ (ppm)} 2.17 (t, 1H), 3.23-3.27 (m, 1H), 3.34-3.39 (m, 1H), 3.52-3.57 (m, 1H), 3.74-3.79 (m, 1H), 4.29-4.42 (m, 2H), 4.47-4.53 (m, 1H), 7.19-7.30 (m, 5H). LC-MS (ESI) (m/z) 208.1 (M+1)$^+$.

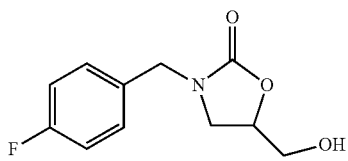 [SMILES: O=C1OC(CO)CN1Cc1ccc(F)cc1]

Preparation of 3-(4-fluorobenzyl)-5-(hydroxymethyl)oxazolidin-2-one: The title compound was prepared according to the procedure for 5-hydroxymethyl-3-isopropyl-oxazolidin-2-one, except 4-fluorobenzyl amine was substituted for isopropyl amine. $^1$H-NMR {CDCl$_3$, 400 MHz, δ (ppm)}. 2.38 (s, 1H), 3.33-3.37 (m, 1H), 3.43-3.47 (m, 1H), 3.61-3.64 (m, 1H), 3.86-3.89 (m, 1H), 4.37-4.47 (m, 2H), 4.58-4.63 (m, 1H), 7.03-7.09 (m, 2H), 7.25-7.30 (m, 2H). LC-MS (ESI) (m/z) 226.1 (M+1)$^+$.

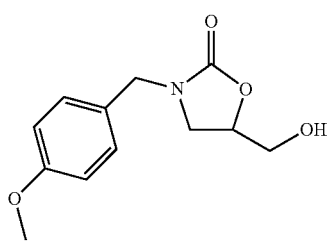 [SMILES: COc1ccc(CN2CC(CO)OC2=O)cc1]

Preparation of 5-(hydroxymethyl)-3-(4-methoxybenzyl)oxazolidin-2-one: The title compound was prepared according to the procedure for 5-hydroxymethyl-3-isopropyl-oxazolidin-2-one, except 4-methoxybenzyl amine was substituted for isopropyl amine. $^1$H-NMR {CDCl$_3$, 400 MHz, δ (ppm)} 2.81 (s, 1H), 3.33-3.34 (m, 1H), 3.43 (t, 1H), 3.60-3.63 (m, 1H), 3.81-3.86 (m, 4H), 4.30-4.44 (m, 2H), 4.54-4.60 (m, 1H), 6.86-6.90 (m, 2H), 7.20-7.25 (m, 2H). LC-MS (ESI) (m/z) 238.1 (M+1)$^+$.

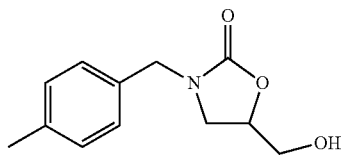 [SMILES: Cc1ccc(CN2CC(CO)OC2=O)cc1]

Preparation of 5-(hydroxymethyl)-3-(4-methylbenzyl)oxazolidin-2-one: The title compound was prepared according to the procedure for 5-hydroxymethyl-3-isopropyl-oxazolidin-2-one, except 4-methylbenzyl amine was substituted for isopropyl amine. $^1$H-NMR {CDCl$_3$, 400 MHz, δ (ppm)} 2.36 (s, 3H), 3.30-3.34 (m, 1H), 3.42-3.46 (m, 1H), 3.60-3.65 (m, 1H), 3.83-3.87 (m, 1H), 4.33-4.50 (m, 2H), 4.55-4.61 (m, 1H), 7.20 (m, 4H). LC-MS (ESI) (m/z) 222.1 (M+1)$^+$.

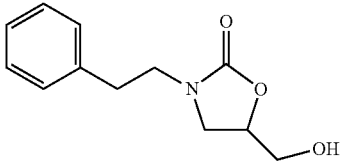 [SMILES: O=C1OC(CO)CN1CCc1ccccc1]

Preparation of 5-(hydroxymethyl)-3-phenethyloxazolidin-2-one: The title compound was prepared according to the procedure for 5-hydroxymethyl-3-isopropyl-oxazolidin-2-one, except 2-phenethylamine was substituted for isopropyl amine. $^1$H-NMR {CDCl$_3$, 400 MHz, δ (ppm)} 2.84 (t, 2H), 3.31-3.35 (m, 1H), 3.39-3.58 (m, 4H), 3.69-3.73 (m, 1H), 4.07 (s, 1H), 4.45-4.51 (m, 1H), 7.19-7.21 (m, 3H), 7.26-7.30 (m, 2H). LC-MS (ESI) (m/z) 222.1 (M+1)$^+$.

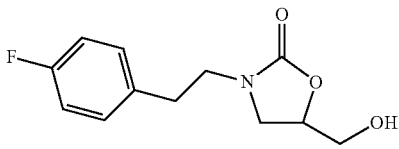 [SMILES: O=C1OC(CO)CN1CCc1ccc(F)cc1]

Preparation of 3-(4-fluorophenethyl)-5-(hydroxymethyl)oxazolidin-2-one: The title compound was prepared according to the procedure for 5-hydroxymethyl-3-isopropyl-oxazolidin-2-one, except 2-(4-fluoro-phenyl)-ethylamine was substituted for isopropyl amine. $^1$H-NMR {CDCl$_3$, 400 MHz, δ (ppm)} 2.80 (s, 1H), 2.86 (t, 2H), 3.36-3.54 (m, 4H), 3.55-3.60 (m, 1H), 3.80-3.83 (m, 1H), 4.51-4.57 (m, 1H), 6.97-7.03 (m, 2H), 7.17-7.22 (m, 2H). LC-MS (ESI) (m/z) 240.1 (M+1)$^+$.

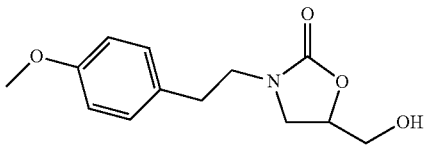 [SMILES: COc1ccc(CCN2CC(CO)OC2=O)cc1]

Preparation of 5-(hydroxymethyl)-3-(4-methoxyphenethyl)oxazolidin-2-one: The title compound was prepared according to the procedure for 5-hydroxymethyl-3-isopropyl-oxazolidin-2-one, except 2-(4-methoxy-phenyl)ethylamine was substituted for isopropyl amine. $^1$H-NMR {CDCl$_3$, 400 MHz, δ (ppm)} 2.82 (t, 3H), 3.33-3.37 (m, 1H), 3.41-3.53 (m, 3H), 3.56-3.61 (m, 1H), 3.77-3.78 (m, 1H), 3.81 (s, 3H), 4.50-4.55 (m, 1H), 6.82-6.87 (m, 2H), 7.13-7.16 (m, 2H). LC-MS (ESI) (m/z) 252.1 (M+1)$^+$.

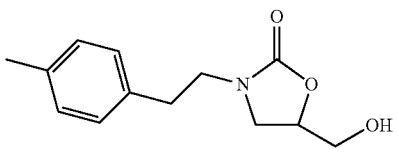 [SMILES: Cc1ccc(CCN2CC(CO)OC2=O)cc1]

Preparation of 5-(hydroxymethyl)-3-(4-methylphenethyl)oxazolidin-2-one: The title compound was prepared according to the procedure for 5-hydroxymethyl-3-isopropyl-oxazolidin-2-one, except 2-(p-tolyl)ethylamine was substituted for isopropyl amine. $^1$H-NMR {CDCl$_3$, 400 MHz, δ (ppm)} 2.34 (s, 3H), 2.51 (s, 1H), 2.85 (t, 2H), 3.33-3.36 (m, 1H), 3.44-3.61 (m, 4H), 3.78-3.82 (m, 1H), 4.50-4.56 (m, 1H), 7.13 (m, 4H). LC-MS (ESI) (m/z) 236.1 (M+1)$^+$.

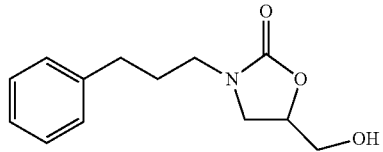 [SMILES: O=C1OC(CO)CN1CCCc1ccccc1]

Preparation of 5-(hydroxymethyl)-3-(3-phenylpropyl)oxazolidin-2-one: The title compound was prepared according to the procedure for 5-hydroxymethyl-3-isopropyl-oxazolidin-2-one, except 3-phenyl-1-propylamine was substituted for isopropyl amine. $^1$H-NMR {CDCl$_3$, 400 MHz, δ (ppm)} 1.86-1.93 (m, 2H), 2.61-2.70 (m, 3H), 3.30-3.34 (m, 2H), 3.44-3.47 (m, 2H), 3.54-3.56 (m, 1H), 3.60-3.66 (m, 1H), 3.85-3.90 (m, 1H), 4.49-4.64 (m, 1H), 7.19-7.23 (m, 3H), 7.28-7.32 (m, 2H). LC-MS (ESI) (m/z) 236.1 (M+1)$^+$.

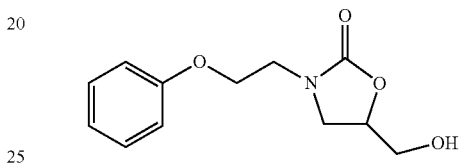

Preparation of 5-(hydroxymethyl)-3-(2-phenoxyethyl)oxazolidin-2-one: The title compound was prepared according to the procedure for 5-hydroxymethyl-3-isopropyl-oxazolidin-2-one, except 2-phenoxyethylamine was substituted for isopropyl amine. $^1$H-NMR {CDCl$_3$, 400 MHz, δ (ppm)} 2.19 (t, 1H), 3.60-3.76 (m, 4H), 3.81-3.90 (m, 2H), 4.17 (t, 2H), 4.60-4.65 (m, 1H), 6.89-6.92 (m, 2H), 6.97-7.02 (m, 1H), 7.30-7.33. LC-MS (ESI) (m/z) 238.1 (M+1)$^+$.

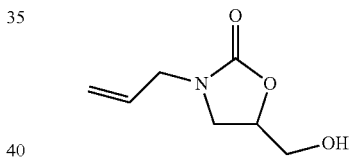

Preparation of 3-Allyl-5-hydroxymethyl-oxazolidin-2-one: The title compound was prepared according to Scheme 2. To a suspension of AgCO$_3$ (3.32 g, 12.03 mmol) in anhydrous methanol (30 mL) containing epibromohydrin (3.18599 g, 23.25 mmol) was added the allyl amine (1.3698 g, 23.98 mmol) and the reaction was stirred overnight in dark. The reaction mixture was later filtered and the organic solvent was stripped off under reduced pressure to obtain a liquid residue. It was chromatographed on silica gel using methanol (0-2%) in dichloromethane to obtain the light yellow solid (0.7711 g, 20.44% yield). $^1$H-NMR {CDCl$_3$, 400 MHz, δ (ppm)} 2.94 (s, 1H), 3.42-3.46 (m, 1H), 3.54 (t, 1H), 3.62-3.66 (m, 1H), 3.85-3.91 (m, 3H), 4.59-4.62 (m, 1H), 5.23-5.30 (m, 2H), 5.72-5.82 (m, 1H).

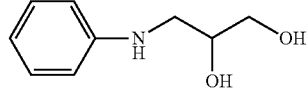 [SMILES: OCC(O)CNc1ccccc1]

Preparation of 3-Phenylamino-propane-1,2-diol: To aniline (14.3038 g, 153.58 mmol) was added glycidol (2.2286 g, 30.08 mmol) and the mixture was heated at 90° C. for 2 hours. After two hours, the reaction mixture was cooled and the product was purified over silica using methylene chloride: MeOH (0-10%) to obtain the product as colorless liquid (3.9634 g, 8% yield). $^1$H-NMR {CDCl$_3$, 400 MHz, δ (ppm)} 2.95-3.00 (m, 1H), 3.07-3.11 (m, 1H), 3.43-3.48 (m, 1H), 3.56-3.82 (m, 5H), 6.51-6.53 (m, 2H), 6.64-6.67 (m, 1H), 7.06-7.10 (m, 2H).

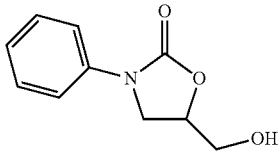 [SMILES: O=C1OC(CO)CN1c1ccccc1]

Preparation of 5-Hydroxymethyl-3-phenyl-oxazolidin-2-one: A mixture of 3-Phenylamino-propane-1,2-diol (3.9634 g, 23.72 mmol), diethylcarbonate (3.0822 g, 26.09 mmol) and anhydrous sodium methoxide (0.1294 g, 2.39 mmol) was stirred under reflux for 4 hours. After cooling at room temperature the reaction mixture was evaporated under reduced pressure to afford a liquid residue. The residue was dissolved in dichloromethane (10 mL) and purified on silica using methylene chloride: MeOH (0-10%) to obtain a creamish white solid (2.6556 g, 57.99% yield). $^1$H-NMR {MeOD$_4$, 400 MHz, δ (ppm)}. 1.60 (s, 1H), 2.41 (t, 1H), 3.65-3.71 (m, 1H), 3.92-3.97 (m, 2H), 4.64-4.70 (m, 1H), 7.05-7.09 (m, 1H), 7.27-7.34 (m, 2H), 7.45-7.48 (m, 2H). LC-MS (ESI) (m/z) 194.1 (M+1)$^+$.

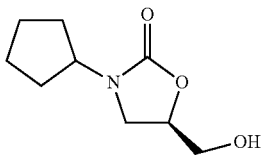 [SMILES: O=C1O[C@@H](CO)CN1C1CCCC1]

Preparation of (R)-3-Cyclopentyl-5-hydroxymethyl-oxazolidin-2-one: To a suspension of K$_2$CO$_3$ (12.33 g, 89.21 mmol) in anhydrous methanol (60 mL) containing R-(−)-epichlorohydrin (4.95 g, 53.50 mmol) and triethylamine (9.0272 g, 89.21 mmol) was added the cyclopentyl amine (3.8 g, 44.62 mmol) and the reaction was refluxed overnight. The reaction mixture was later filtered and the organic solvent was stripped off under reduced pressure to obtain a liquid residue. It was chromatographed on silica gel using methanol (0-2%) in dichloromethane to obtain the product as light yellow liquid. LC-MS (ESI) (m/z) 186.1 (M+1).

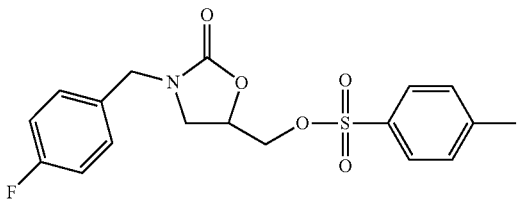 [SMILES: Cc1ccc(S(=O)(=O)OCC2CN(Cc3ccc(F)cc3)C(=O)O2)cc1]

Preparation of (3-(4-fluorobenzyl)-2-oxooxazolidin-5-yl) methyl 4-methylbenzenesulfonate: p-Toluene sulfonyl chloride (2.4 g, 12.61 mmol) in methylene chloride (10 mL) was added dropwise to a chilled solution of 4-flurobenzyl-oxazoldin-2-one (2.4133 g, 10.71 mmol) and triethylamine (1.5972 g, 15.78 mmol) in methylene chloride (20 mL). The reaction was stirred in ice at 0° C. for 1 hour followed by overnight stirring at room temperature. It was later quenched with ice water and the organic layer was washed successfully with 10% HCl, saturated aqueous sodium bicarbonate and brine. The organic layer was dried over MgSO$_4$ and concentrated under reduced pressure to obtain a solid/oil which was purified on silica gel redisep column using hexane: ethyl acetate (0-100%) to obtain colorless liquid (1.9902 g, 48.95% yield). $^1$H-NMR {CDCl$_3$, 400 MHz, δ (ppm)}2.48 (s, 3H), 3.28-3.30 (m, 1H), 3.50 (t, 1H), 4.11-4.12 (m, 2H), 4.34-4.43 (m, 2H), 4.64-4.70 (m, 1H), 7.03-7.07 (m, 2H), 7.22-7.27 (m, 2H), 7.38-7.39 (m, 2H), 7.76-7.78 (m, 2H). LC-MS (ESI) (m/z) 380.1 (M+1)$^+$.

The following compounds can be prepared by the procedure of (3-(4-fluorobenzyl)-2-oxooxazolidin-5-yl)methyl 4-methylbenzenesulfonate The skilled practitioner will know how to substitute the appropriate reagents, starting materials and purification methods known to those skilled in the art, in order to prepare the compounds provided herein.

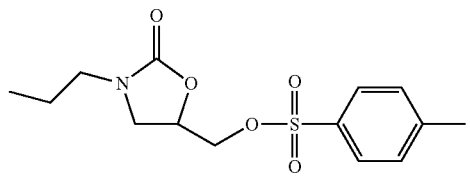 [SMILES: CCCN1CC(COS(=O)(=O)c2ccc(C)cc2)OC1=O]

Preparation of (2-oxo-3-propyloxazolidin-5-yl)methyl 4-methylbenzenesulfonate: The title compound was prepared according to the procedure for (3-(4-fluorobenzyl)-2-oxooxazolidin-5-yl)methyl 4-methylbenzenesulfonate, except 5-(hydroxymethyl)-3-propyloxazolidin-2-one was substituted for 3-(4-Fluorobenzyl)-5-(hydroxymethyl)oxazolidin-2-one. $^1$H-NMR {CDCl$_3$, 400 MHz, δ (ppm)} 0.91 (t, 3H), 1.48-1.57 (sextet, 2H), 2.47 (s, 3H), 3.12-3.26 (m, 2H), 3.40-3.44 (m, 1H), 3.63 (t, 1H), 4.18 (t, 2H), 4.65-4.71 (m, 1H), 7.37-7.39 (d, 2H), 7.78-7.80 (d, 2H). LC-MS (ESI) (m/z) 314.1 (M+1)$^+$.

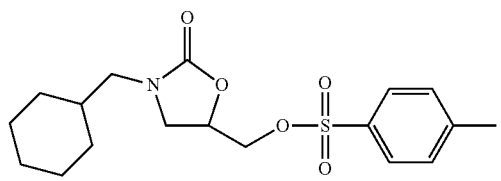 [SMILES: Cc1ccc(S(=O)(=O)OCC2CN(CC3CCCCC3)C(=O)O2)cc1]

Preparation of (3-(cyclohexylmethyl)-2-oxooxazolidin-5-yl)methyl 4-methylbenzenesulfonate: The title compound was prepared according to the procedure for (3-(4-fluorobenzyl)-2-oxooxazolidin-5-yl)methyl 4-methylbenzenesulfonate, except 3-cyclohexyl-5-hydroxymethyl-oxazolidin-2-one was substituted for 3-(4-Fluorobenzyl)-5-(hydroxymethyl)oxazolidin-2-one. $^1$H-NMR {CDCl$_3$, 400 MHz, δ (ppm)} 0.89-0.99 (m, 2H), 1.11-1.28 (m, 3H), 1.47-1.61 (m, 1H), 1.63-1.74 (m, 6H), 2.47 (s, 3H), 3.00-3.11 (m, 2H), 3.42-3.46 (m, 1H), 3.63 (t, 1H), 4.11-4.18 (m, 2H), 4.66-4.71 (m, 1H), 7.35-7.39 (m, 2H), 7.79-7.81 (m, 2H). LC-MS (ESI) (m/z) 368.1 (M+1)$^+$.

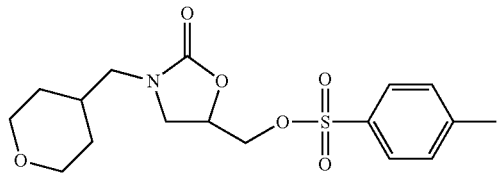 [SMILES: Cc1ccc(S(=O)(=O)OCC2CN(CC3CCOCC3)C(=O)O2)cc1]

Preparation of (2-oxo-3-((tetrahydro-2H-pyran-4-yl) methyl)oxazolidin-5-yl)methyl 4-methylbenzene sulfonate:

The title compound was prepared according to the procedure for (3-(4-fluorobenzyl)-2-oxooxazolidin-5-yl)methyl 4-methylbenzenesulfonate, except 5-Hydroxymethyl-3-(tetrahydro-pyran-4-ylmethyl)-oxazolidin-2-one was substituted for 3-(4-Fluorobenzyl)-5-(hydroxymethyl)oxazolidin-2-one. $^1$H-NMR {CDCl$_3$, 400 MHz, δ (ppm)} 1.23-1.36 (m, 2H), 1.54-1.58 (m, 2H), 1.78-1.89 (m, 1H), 2.45 (s, 3H), 3.01-3.06 (m, 1H), 3.14-3.19 (m, 1H), 3.32-3.38 (m, 2H), 3.46-3.50 (m, 1H), 3.66 (t, 1H), 3.93-3.97 (m, 2H), 4.15 (d, 2H), 4.66-4.74 (m, 1H), 7.37 (d, 2H), 7.77 (d, 2H). LC-MS (ESI) (m/z) 370.1 (M+1)$^+$.

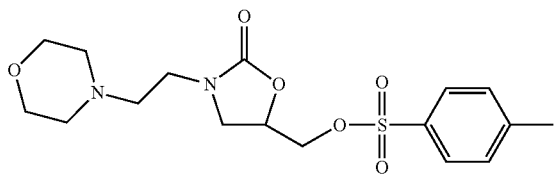 [SMILES: Cc1ccc(S(=O)(=O)OCC2CN(CCN3CCOCC3)C(=O)O2)cc1]

Preparation of (3-(2-morpholinoethyl)-2-oxooxazolidin-5-yl)methyl 4-methylbenzenesulfonate: The title compound was prepared according to the procedure for (3-(4-fluorobenzyl)-2-oxooxazolidin-5-yl)methyl 4-methylbenzenesulfonate, except 5-Hydroxymethyl-3-(2-morpholin-4-yl-ethyl)-oxazolidin-2-one was substituted for 3-(4-Fluorobenzyl)-5-(hydroxymethyl)oxazolidin-2-one.
$^1$H-NMR {CDCl$_3$, 400 MHz, δ (ppm)} 2.47-2.55 (m, 9H), 3.29-3.45 (m, 2H), 3.54-3.58 (m, 1H), 3.67 (t, 4H), 3.74 (t, 1H), 4.14-4.15 (m, 2H), 4.66-4.72 (m, 1H), 7.39 (d, 2H), 7.80 (d, 2H). LC-MS (ESI) (m/z) 385.1 (M+1)$^+$.

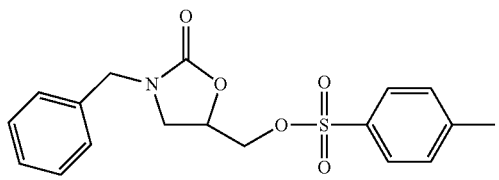 [SMILES: Cc1ccc(S(=O)(=O)OCC2CN(Cc3ccccc3)C(=O)O2)cc1]

Preparation of (3-benzyl-2-oxooxazolidin-5-yl)methyl 4-methylbenzenesulfonate: The title compound was prepared according to the procedure for (3-(4-fluorobenzyl)-2-oxooxazolidin-5-yl)methyl 4-methylbenzenesulfonate, except 3-Benzyl-5-hydroxymethyl-oxazolidin-2-one was substituted for 3-(4-Fluorobenzyl)-5-(hydroxymethyl)oxazolidin-2-one. $^1$H-NMR {CDCl$_3$, 400 MHz, δ (ppm)} 2.45 (s, 3H), 3.23-3.27 (m, 1H), 3.48 (t, 1H), 4.07-4.14 (m, 1H), 4.39 (s, 2H), 4.62-4.68 (m, 1H), 7.24-7.26 (m, 2H), 7.30-7.38 (m, 5H), 7.73-7.76 (m, 2H). LC-MS (ESI) (m/z) 363.1 (M+1)$^+$.

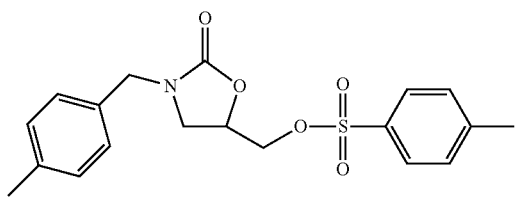

(3-(4-Methylbenzyl)-2-oxooxazolidin-5-yl)methyl 4-methylbenzenesulfonate: The title compound was prepared according to the procedure for (3-(4-fluorobenzyl)-2-oxooxazolidin-5-yl)methyl 4-methylbenzenesulfonate, except 5-(hydroxymethyl)-3-(4-methylbenzyl)oxazolidin-2-one was substituted for 3-(4-Fluorobenzyl)-5-(hydroxymethyl)oxazolidin-2-one. $^1$H-NMR {CDCl$_3$, 400 MHz, δ (ppm)} 2.27 (s, 3H), 2.38 (s, 3H), 3.15-3.19 (m, 1H), 3.38 (t, 1H), 3.96-4.04 (m, 2H), 4.23-4.32 (m, 2H), 4.52-4.58 (m, 1H), 7.02-7.09 (m, 4H), 7.28 (d, 2H), 7.67-7.69 (m, 2H). LC-MS (ESI) (m/z) 376.1 (M+1)$^+$.

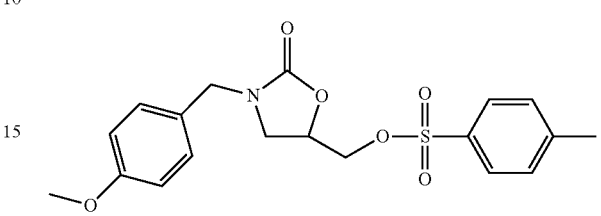

Preparation of (3-(4-methoxybenzyl)-2-oxooxazolidin-5-yl)methyl 4-methylbenzenesulfonate: The title compound was prepared according to the procedure for (3-(4-fluorobenzyl)-2-oxooxazolidin-5-yl)methyl 4-methylbenzenesulfonate, except 5-(hydroxymethyl)-3-(4-methoxybenzyl)oxazolidin-2-one was substituted for 3-(4-Fluorobenzyl)-5-(hydroxymethyl)oxazolidin-2-one. $^1$H-NMR {CDCl$_3$, 400 MHz, δ (ppm)} 2.46 (s, 3H), 3.44 (t, 1H), 3.81 (s, 3H), 4.04-4.13 (m, 2H), 4.33 (s, 1H), 4.60-4.66 (m, 1H), 6.86-6.90 (m, 2H), 7.15-7.19 (m, 2H), 7.35-7.37 (m, 2H), 7.74-7.76 (m, 2H). LC-MS (ESI) (m/z) 392.1 (M+1)$^+$.

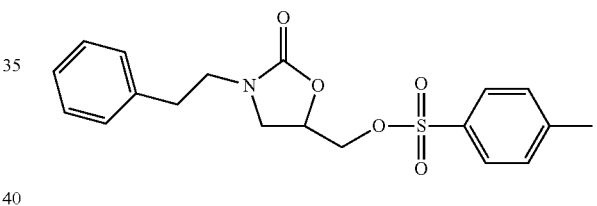

Preparation of (2-oxo-3-phenethyloxazolidin-5-yl)methyl 4-methylbenzenesulfonate: The title compound was prepared according to the procedure for (3-(4-fluorobenzyl)-2-oxooxazolidin-5-yl)methyl 4-methylbenzenesulfonate, except 5-(hydroxymethyl)-3-phenethyloxazolidin-2-one was substituted for 3-(4-Fluorobenzyl)-5-(hydroxymethyl)oxazolidin-2-one. $^1$H-NMR {CDCl$_3$, 400 MHz, δ (ppm)} 2.46 (s, 3H), 2.83 (t, 1H), 3.25-3.29 (m, 1H), 3.45-3.52 (m, 3H), 4.01-4.09 (m, 2H), 4.56-4.61 (m, 1H), 7.20-7.26 (m, 3H), 7.30-7.33 (m, 2H), 7.38 (d, 2H), 7.77-7.80 (m, 2H). LC-MS (ESI) (m/z) 376.1 (M+1)$^+$.

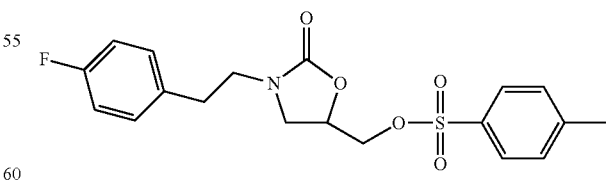

Preparation of (3-(4-fluorophenethyl)-2-oxooxazolidin-5-yl)methyl 4-methylbenzenesulfonate: The title compound was prepared according to the procedure for (3-(4-fluorobenzyl)-2-oxooxazolidin-5-yl)methyl 4-methylbenzenesulfonate, except 3-(4-fluorophenethyl)-5-(hydroxymethyl)oxazolidin-2-one was substituted for 3-(4-Fluorobenzyl)-5-

(hydroxymethyl)oxazolidin-2-one. ¹H-NMR {CDCl₃, 400 MHz, δ (ppm)}2.47 (s, 3H), 2.84 (t, 2H), 3.32-3.36 (m, 1H), 3.39-3.54 (m, 3H), 4.02-4.16 (m, 3H), 6.98-7.03 (m, 2H), 7.15-7.20 (m, 2H) 7.39 (d, 2H), 7.78-7.80 (m, 2H). LC-MS (ESI) (m/z) 394.1 (M+1)⁺.

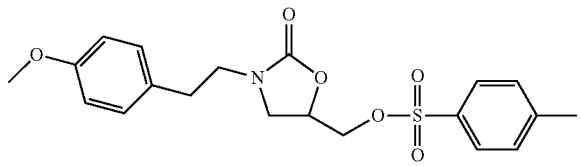

Preparation of (3-(4-methoxyphenethyl)-2-oxooxazolidin-5-yl)methyl 4-methylbenzenesulfonate: The title compound was prepared according to the procedure for (3-(4-fluorobenzyl)-2-oxooxazolidin-5-yl)methyl 4-methylbenzenesulfonate, except 5-(hydroxymethyl)-3-(4-methoxyphenethyl)oxazolidin-2-one was substituted for 3-(4-Fluorobenzyl)-5-(hydroxymethyl)oxazolidin-2-one. ¹H-NMR {CDCl₃, 400 MHz, δ (ppm)} 2.47 (s, 3H), 2.78 (t, 2H), 3.26-3.30 (m, 1H), 3.42-3.52 (m, 3H), 3.81 (s, 3H), 4.01-4.16 (m, 3H), 4.56-4.64 (m, 1H), 6.85 (d, 2H), 7.11 (d, 2H), 7.38 (d, 2H), 7.78 (d, 2H). LC-MS (ESI) (m/z) 406.1 (M+1)⁺.

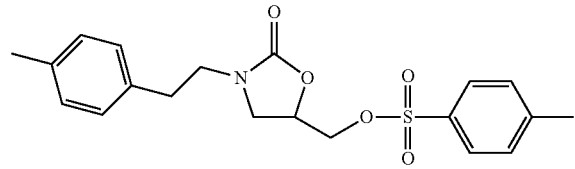

Preparation of (3-(4-methylphenethyl)-2-oxooxazolidin-5-yl)methyl 4-methylbenzenesulfonate: The title compound was prepared according to Scheme 2, and in the manner of the procedure for (3-(4-fluorobenzyl)-2-oxooxazolidin-5-yl)methyl 4-methylbenzenesulfonate, except 5-(hydroxymethyl)-3-(4-methylphenethyl)oxazolidin-2-one was substituted for 3-(4-Fluorobenzyl)-5-(hydroxymethyl)oxazolidin-2-one. Colorless viscous liquid. Yield: 75.91%. ¹H-NMR {CDCl₃, 400 MHz, δ (ppm)} 2.34 (s, 3H), 2.47 (s, 3H), 2.81 (t, 2H), 3.26-3.30 (m, 1H), 3.44-3.53 (m, 3H), 4.01-4.16 (m, 2H), 4.56-4.62 (m, 1H), 7.08-7.13 (m, 4H), 7.37-7.39 (d, 2H), 7.78-7.80 (d, d, 2H). LC-MS (ESI) (m/z) 390.1 (M+1)⁺.

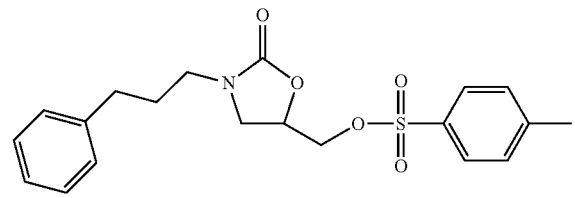 [SMILES: Cc1ccc(S(=O)(=O)OCC2CN(CCCc3ccccc3)C(=O)O2)cc1]

Preparation of (2-oxo-3-(3-phenylpropyl)oxazolidin-5-yl)methyl 4-methylbenzenesulfonate: The title compound was prepared according to the procedure for (3-(4-fluorobenzyl)-2-oxooxazolidin-5-yl)methyl 4-methylbenzenesulfonate, except 5-(hydroxymethyl)-3-(3-phenylpropyl)oxazolidin-2-one was substituted for 3-(4-Fluorobenzyl)-5-(hydroxymethyl)oxazolidin-2-one. ¹H-NMR {CDCl₃, 400 MHz, δ (ppm)} 1.83-1.90 (m, 2H), 2.45 (s, 3H), 2.61-2.66 (m, 2H), 3.25-3.32 (m, 2H), 3.38-3.42 (m, 1H), 3.58 (t, 1H), 4.11-4.13 (m, 2H), 4.59-4.65 (m, 1H), 7.19-7.23 (m, 3H), 7.28-7.32 (m, 2H), 7.34-7.36 (m, 2H), 7.77-7.83 (m, 2H). LC-MS (ESI) (m/z) 390.1 (M+1)⁺.

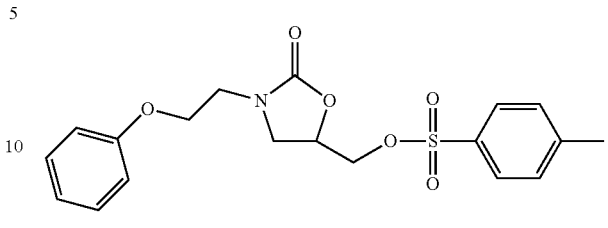

Preparation of (2-oxo-3-(2-phenoxyethyl)oxazolidin-5-yl)methyl 4-methylbenzenesulfonate: The title compound was prepared according to the procedure for (3-(4-fluorobenzyl)-2-oxooxazolidin-5-yl)methyl 4-methylbenzenesulfonate, except 5-(hydroxymethyl)-3-(2-phenoxyethyl)oxazolidin-2-one was substituted for 3-(4-Fluorobenzyl)-5-(hydroxymethyl)oxazolidin-2-one. ¹H-NMR {CDCl₃, 400 MHz, δ (ppm)} 2.45 (s, 3H), 3.59-3.73 (3H), 3.88 (t, 1H), 4.11-4.16 (m, 5H), 4.66-4.72 (m, 1H), 6.87-6.91 (m, 2H), 6.98-7.02 (m, 1H), 7.29-7.35 (m, 4H), 7.75-7.78 (m, 2H). LC-MS (ESI) (m/z) 392.1 (M+1)⁺.

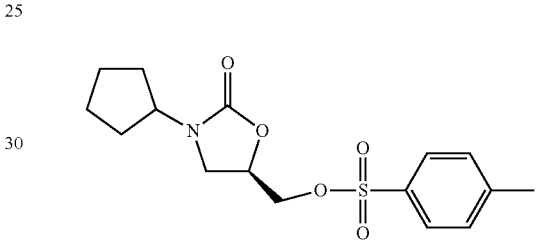

Preparation of (R)-(3-cyclopentyl-2-oxooxazolidin-5-yl)methyl 4-methylbenzenesulfonate: The title compound was prepared according to the procedure for (3-(4-fluorobenzyl)-2-oxooxazolidin-5-yl)methyl 4-methylbenzenesulfonate, except (3-cyclopentyl-5-hydroxymethyl-oxazolidin-2-one) was substituted for 3-(4-Fluorobenzyl)-5-(hydroxymethyl)oxazolidin-2-one. ¹H-NMR {CDCl₃, 400 MHz, δ (ppm)} 1.45-1.57 (m, 2H), 1.58-1.65 (m, 2H), 1.66-1.74 (m, 2H), 1.82-1.91 (m, 2H), 2.47 (s, 3H), 3.37-3.40 (m, 1H), 3.61 (t, 1H), 4.09-4.23 (m, 3H), 4.64-4.70 (m, 1H), 7.38 (d, 2H), 7.83 (d, 2H). LC-MS (ESI) (m/z) 340.1 (M+1)⁺.

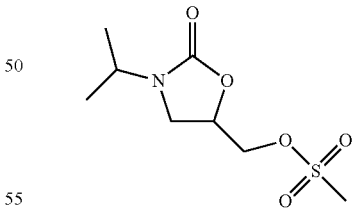

Preparation of (3-isopropyl-2-oxooxazolidin-5-yl)methyl methanesulfonate: Methane sulfonyl chloride (1.653 g, 14.430 mmol) in methylene chloride (20 mL) was added dropwise to a chilled solution of 5-Hydroxymethyl-3-isopropyl-oxazolidin-2-one (1.8387 g, 11.551 mmol) and triethylamine (1.753 g, 17.323 mmol) in methylene chloride (20 mL). The reaction was stirred in ice at 0° C. for 1 hour followed by overnight stirring at room temperature. It was later quenched with ice water and the organic layer was washed successfully with 10% HCl, saturated aqueous sodium bicarbonate and brine. The organic layer was dried over MgSO₄ and concentrated under reduced pressure to obtain a solid/oil which was utilized for next step without purification.

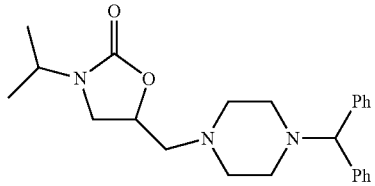 [SMILES: CC(C)N1CC(CN2CCN(C(c3ccccc3)c3ccccc3)CC2)OC1=O]

Preparation of 5-(4-Benzhydryl-piperazin-1-ylmethyl)-3-isopropyl-oxazolidin-2-one: (3-isopropyl-2-oxooxazolidin-5-yl)methyl methanesulfonate (1.801 g, 7.59 mmol) and diphenylmethylpiperazine (9.572 g, 37.92 mmol) in anhydrous tetrahydrofuran (60 mL) were stirred at reflux under nitrogen atmosphere for 24 hours. The mixture was cooled and concentrated under reduced pressure and the residue was dissolved in dichloromethane and purified by redisep silica gel columns using dichloromethane-methanol gradient system (0-10%) or C18 columns using acetonitrile-water (containing 0.1% formic acid; 0-100%) to obtain pale yellow solid (0.7432 g, 24.86%) ¹H-NMR {CDCl₃, 400 MHz, δ (ppm)} 1.13-1.16 (m, 6H), 2.24-2.68 (m, 10H), 3.16-3.20 (t, 1H), 3.48-3.53 (t, 1H), 3.99-4.13 (heptet, 1H), 4.59-4.65 (m, 1H), 7.14-7.18 (m, 2H), 7.23-7.27 (m, 4H), 7.38-7.40 (m, 4H). LC-MS (ESI) (m/z) 394.1 (M+1)⁺.

The following compounds can be prepared by the procedure of 5-(4-Benzhydryl-piperazin-1-ylmethyl)-3-isopropyl-oxazolidin-2-one. The skilled practitioner will know how to substitute the appropriate reagents, starting materials and purification methods known to those skilled in the art, in order to prepare the compounds provided herein.

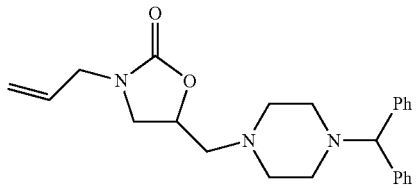 [SMILES: C=CCN1CC(CN2CCN(C(c3ccccc3)c3ccccc3)CC2)OC1=O]

Preparation of 3-allyl-5-(4-benzhydryl-piperazin-1-ylmethyl)-oxazolidin-2-one: The title compound was prepared according to the procedure for 5-(4-Benzhydryl-piperazin-1-ylmethyl)-3-isopropyl-oxazolidin-2-one, except 3-allyl-5-hydroxymethyl-oxazolidin-2-one was substituted for 5-hydroxymethyl-3-isopropyl-oxazolidin-2-one. ¹H-NMR {CDCl₃, 400 MHz, δ (ppm)} 2.55 (bs, 4H), 2.78-2.95 (m, 5H), 3.07-3.11 (dd, 3 Hz, 1H), 3.14-3.19 (dd, 9 Hz, 1H), 3.63 (t, 1H), 3.77-3.90 (m, 2H), 4.26 (s, 1H), 4.80-4.87 (m, 1H), 5.16-5.25 (m, 2H), 5.69-5.79 (m, 1H), 7.16-7.22 (m, 2H), 7.25-7.29 (m, 4H), 7.38-7.40 (m, 4H). LC-MS (ESI) (m/z) 392.1 (M+1)⁺.

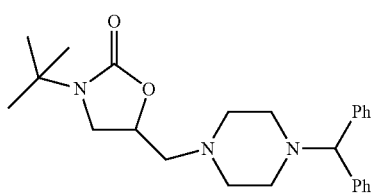 [SMILES: CC(C)(C)N1CC(CN2CCN(C(c3ccccc3)c3ccccc3)CC2)OC1=O]

Preparation of 5-(4-benzhydryl-piperazin-1-ylmethyl)-3-tert-butyl-oxazolidin-2-one: The title compound was prepared according to the procedure for 5-(4-Benzhydryl-piperazin-1-ylmethyl)-3-isopropyl-oxazolidin-2-one, except 3-tert-Butyl-5-hydroxymethyl-oxazolidin-2-one was substituted for 5-hydroxymethyl-3-isopropyl-oxazolidin-2-one. ¹H-NMR {CDCl₃, 400 MHz, δ (ppm)} 1.36 (s, 9H), 2.57 (bs, 4H), 2.78-2.83 (dd, 13.5 Hz, 1H), 2.88-3.08 (m, 4H), 3.11-3.15 (m, 1H), 3.23 (t, 1H), 3.69-3.76 (m, 2H), 4.27 (s, 1H), 4.69-4.75 (m, 1H), 7.16-7.20 (m, 2H), 7.25-7.29 (m, 4H), 7.38-7.40 (m, 4H). LC-MS (ESI) (m/z) 408.1 (M+1)⁺.

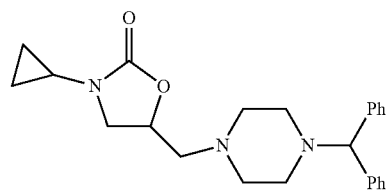 [SMILES: O=C1OC(CN2CCN(C(c3ccccc3)c3ccccc3)CC2)CN1C1CC1]

Preparation of 5-(4-benzhydryl-piperazin-1-ylmethyl)-3-cyclopropyl-oxazolidin-2-one: The title compound was prepared according to the procedure for 5-(4-Benzhydryl-piperazin-1-ylmethyl)-3-isopropyl-oxazolidin-2-one, except 3-cyclopropyl-5-hydroxymethyl-oxazolidin-2-one was substituted for 5-hydroxymethyl-3-isopropyl-oxazolidin-2-one. ¹H-NMR {CDCl₃, 400 MHz, δ (ppm)} 0.63-0.83 (m, 4H), 2.46-2.58 (m, 5H), 2.81-3.01 (m, 5H), 3.16-3.21 (m, 2H), 3.65 (t, 1H), 4.27 (s, 1H), 4.77-4.84 (m, 1H), 7.18-7.20 (m, 2H), 7.25-7.29 (m, 4H), 7.38-7.40 (m, 4H). LC-MS (ESI) (m/z) 392.1 (M+1)⁺.

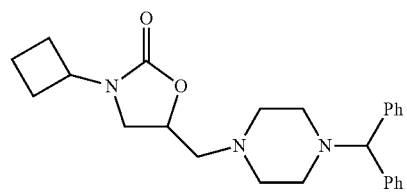 [SMILES: O=C1OC(CN2CCN(C(c3ccccc3)c3ccccc3)CC2)CN1C1CCC1]

Preparation of 5-(4-benzhydryl-piperazin-1-ylmethyl)-3-cyclobutyl-oxazolidin-2-one: The title compound was prepared according to the procedure for 5-(4-Benzhydryl-piperazin-1-ylmethyl)-3-isopropyl-oxazolidin-2-one, except 3-cyclobutyl-5-hydroxymethyl-oxazolidin-2-one was substituted for 5-hydroxymethyl-3-isopropyl-oxazolidin-2-one. ¹H-NMR {CDCl₃, 400 MHz, δ (ppm)} 1.61-1.72 (m, 2H), 2.09-2.15 (m, 4H), 2.40-2.69 (m, 10H), 3.28-3.32 (dd, 8.4 Hz, 1H), 3.61 (t, 1H), 4.21 (s, 1H), 431-4.40 (m, 1H), 4.55-4.62 (m, 1H), 7.14-7.16 (m, 2H), 7.23-7.27 (m, 4H), 7.38-7.40 (m, 4H). LC-MS (ESI) (m/z) 406.1 (M+1)⁺.

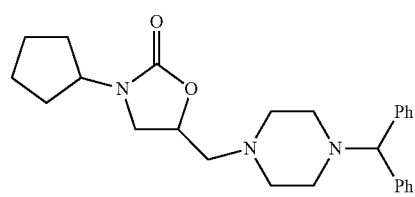 [SMILES: O=C1OC(CN2CCN(C(c3ccccc3)c3ccccc3)CC2)CN1C1CCCC1]

Preparation of 5-(4-benzhydryl-piperazin-1-ylmethyl)-3-cyclopentyl-oxazolidin-2-one: The title compound was prepared according to the procedure for 5-(4-Benzhydryl-piperazin-1-ylmethyl)-3-isopropyl-oxazolidin-2-one, except 3-cyclopentyl-5-hydroxymethyl-oxazolidin-2-one was substituted for 5-hydroxymethyl-3-isopropyl-oxazolidin-2-one.

¹H-NMR {CDCl₃, 400 MHz, δ (ppm)} 0.90 (d, 6H), 1.79-1.93 (m, 1H), 2.39-2.68 (m, 10H), 2.97-3.08 (m, 2H), 3.24-3.28 (m, 1H), 3.54 (t, 1H), 4.20 (s, 1H), 4.56-4.63 (m, 1H), 7.14-7.18 (m, 2H), 7.23-7.27 (m, 4H), 7.38-7.40 (m, 4H). LC-MS (ESI) (m/z) 408.2 (M+1)⁺.

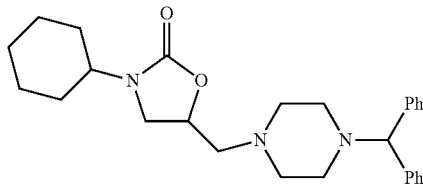 [SMILES: O=C1OC(CN2CCN(C(c3ccccc3)c3ccccc3)CC2)CN1C1CCCCC1]

Preparation of 5-(4-benzhydryl-piperazin-1-ylmethyl)-3-cyclohexyl-oxazolidin-2-one: The title compound was prepared according to the procedure for 5-(4-Benzhydryl-piperazin-1-ylmethyl)-3-isopropyl-oxazolidin-2-one, except 3-cyclohexyl-5-hydroxymethyl-oxazolidin-2-one was substituted for 5-hydroxymethyl-3-isopropyl-oxazolidin-2-one. ¹H NMR: {CDCl₃, 400 MHz, δ (ppm)} 1.01-1.09 (m, 1H), 1.25-1.39 (m, 4H), 1.65 (d, 1H), 1.77 (m, 4H), 2.39-2.66 (m, 10H), 3.21 (t, 1H), 3.50 (t, 1H), 3.62-3.70 (m, 1H), 4.21 (s, 1H), 4.53-4.60 (m, 1H), 7.14-7.17 (m, 2H), 7.23-7.27 (m, 4H), 7.38-7.40 (m, 4H). LC-MS (ESI) (m/z) 434.1 (M+1)⁺.

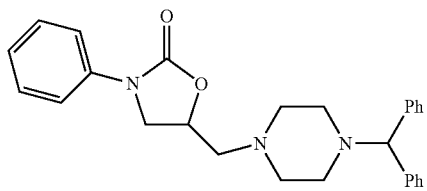 [SMILES: O=C1OC(CN2CCN(C(c3ccccc3)c3ccccc3)CC2)CN1c1ccccc1]

Preparation of 5-((4-benzhydrylpiperazin-1-yl)methyl)-3-phenyloxazolidin-2-one: The title compound was prepared according to the procedure for 5-(4-Benzhydryl-piperazin-1-ylmethyl)-3-isopropyl-oxazolidin-2-one, except 5-hydroxymethyl-3-phenyl-oxazolidin-2-one was substituted for 5-hydroxymethyl-3-isopropyl-oxazolidin-2-one. ¹H NMR: {CDCl₃, 400 MHz, δ (ppm)} 2.46-2.80 (m, 10H), 3.76-3.80 (m, 1H), 4.02 (t, 1H), 4.27 (s, 1H), 4.71-4.77 (m, 1H), 7.14-7.17 (m, 1H), 7.20-7.24 (m, 2H), 7.29-7.33 (m, 4H), 7.37-7.42 (m, 2H), 7.45-7.47 (m, 4H), 7.56-7.58 (m, 2H). LC-MS (ESI) (m/z) 428.2 (M+1)⁺.

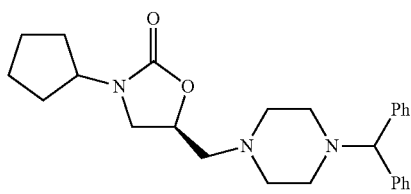 [SMILES: O=C1O[C@@H](CN2CCN(C(c3ccccc3)c3ccccc3)CC2)CN1C1CCCC1]

Preparation of 5-(4-Benzhydryl-piperazin-1-ylmethyl)-3-cyclopentyl-oxazolidin-2-one: The title compound was prepared according to the procedure for 5-(4-Benzhydryl-piperazin-1-ylmethyl)-3-isopropyl-oxazolidin-2-one, except (R)-(3-cyclopentyl-2-oxooxazolidin-5-yl)methyl 4-methylbenzenesulfonate was substituted for (3-Isopropyl-2-oxooxazolidin-5-yl)methyl methanesulfonate. ¹H-NMR {CDCl₃, 400 MHz, δ (ppm)} 1.48-1.73 (6H), 1.83-1.91 (m, 2H), 2.42-2.71 (m, 10H), 3.23-3.27 (m, 1H), 3.54 (t, 1H), 4.19- 4.29 (m, 2H), 4.58-4.64 (m, 1H), 7.17-7.21 (m, 2H), 7.26-7.30 (m, 4H), 7.40-7.42 (m, 4H). LC-MS (ESI) (m/z) 420.3 (M+1)⁺.

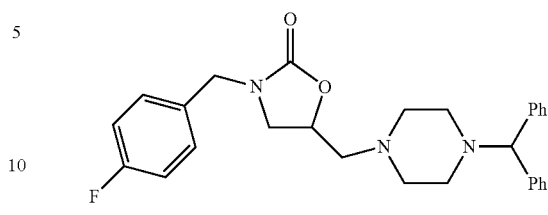

Preparation of 5-((4-benzhydrylpiperazin-1-yl)methyl)-3-(4-fluorobenzyl) oxazolidin-2-one: (3-(4-fluorobenzyl)-2-oxooxazolidin-5-yl)methyl 4-methylbenzene sulfonate (1.1215 g, 2.955 mmol) and diphenylmethylpiperazine and (1.49 g, 5.90 mmol) in anhydrous tetrahydrofuran (5 mL) and triethyl amine (1.1648 g, 11.51 mmol) were stirred under microwave at 120° C. for 1 hour. After 1 hour, the solvent was stripped off, residue was dissolved in dichloromethane and purified by silica gel column using hexane-ethyl acetate (0-100%) to obtain white solid (0.8941 g, 65.83% yield). ¹H NMR: {CDCl3, 400 MHz, δ (ppm)}2.37-2.67 (m, 10H), 3.17-3.19 (m, 1H), 3.43 (t, 1H), 4.21 (s, 1H), 4.39 (s, 2H), 4.56-4.69 (m, 1H), 7.01-7.07 (m, 2H), 7.17-7.21 (m, 2H), 7.25-7.30 (m, 6H), 7.40-7.42 (m, 4H). LC-MS (ESI) (m/z) 460.2 (M+1)⁺.

The following compounds can be prepared by the procedure of 5-((4-benzhydrylpiperazin-1-yl)methyl)-3-(4-fluorobenzyl)oxazolidin-2-one. The skilled practitioner will know how to substitute the appropriate reagents, starting materials and purification methods known to those skilled in the art, in order to prepare the compounds provided herein.

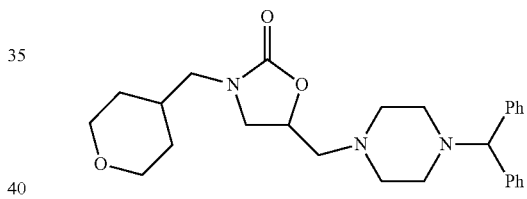

Preparation of 5-(4-Benzhydryl-piperazin-1-ylmethyl)-3-(tetrahydro-pyran-4-ylmethyl)-oxazolidin-2-one: The title compound was prepared according to the procedure for 5-((4-benzhydrylpiperazin-1-yl)methyl)-3-(4-fluorobenzyl) oxazolidin-2-one, except (2-oxo-3-((tetrahydro-2H-pyran-4-yl)methyl)oxazolidin-5-yl)methyl 4-methylbenzene sulfonate was substituted for (3-(4-Fluorobenzyl)-2-oxooxazolidin-5-yl)methyl 4-methylbenzenesulfonate. ¹H NMR: {CDCl₃, 400 MHz, δ (ppm)} 1.31-1.41 (m, 2H), 1.58-1.61 (m, 2H), 1.74 (s, 1H), 1.81-1.92 (m, 1H), 2.41-2.70 (m, 10H), 3.08-3.18 (m, 2H), 3.31-3.41 (m, 3H), 3.60 (t, 1H), 3.97-4.01 (m, 2H), 4.22 (s, 1H), 4.60-4.66 (m, 1H), 7.17-7.21 (m, 2H), 7.26-7.30 (m, 4H), 7.40-7.42 (m, 4H). LC-MS (ESI) (m/z) 450.3 (M+1)⁺.

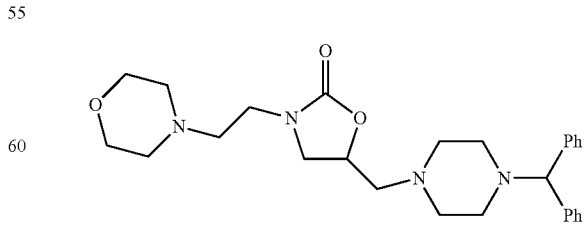

Preparation of 5-((4-benzhydrylpiperazin-1-yl)methyl)-3-(2-morpholinoethyl)oxazolidin-2-one: The title compound was prepared according the procedure for 5-((4-benzhydrylpiperazin-1-yl)methyl)-3-(4-fluorobenzyl)oxazolidin-2-one, except (3-(2-morpholinoethyl)-2-oxooxazolidin-5-yl) methyl 4-methylbenzenesulfonate was substituted for (3-(4-Fluorobenzyl)-2-oxooxazolidin-5-yl)methyl 4-methylbenzenesulfonate. $^1$H NMR: {CDCl$_3$, 400 MHz, δ (ppm)} 2.43-2.72 (m, 16H), 3.34-3.39 (m, 3H), 3.64-3.70 (m, 5H), 4.23 (s, 1H), 4.59-4.66 (m, 1H), 7.17-7.21 (m, 2H), 7.26-7.30 (m, 4H), 7.40-7.42 (m, 4H). LC-MS (ESI) (m/z) 465.3 (M+1)$^+$.

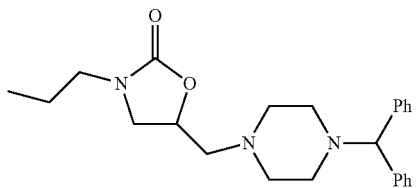 [SMILES: CCCN1CC(CN2CCN(C(c3ccccc3)c3ccccc3)CC2)OC1=O]

Preparation of 5-(4-Benzhydryl-piperazin-1-ylmethyl)-3-propyl-oxazolidin-2-one: The title compound was prepared according to the procedure for 5-((4-benzhydrylpiperazin-1-yl)methyl)-3-(4-fluorobenzyl)oxazolidin-2-one, except 2-oxo-3-propyloxazolidin-5-yl)methyl 4-methylbenzenesulfonate was substituted for (3-(4-Fluorobenzyl)-2-oxooxazolidin-5-yl)methyl 4-methylbenzenesulfonate. $^1$H NMR: {CDCl3, 400 MHz, δ (ppm)} 0.93 (t, 3H), 1.52-1.65 (m, 2H), 2.42-2.72 (m, 10H), 3.15-3.30 (m, 3H), 3.57 (t, 1H), 4.23 (s, 1H), 4.59-4.66 (m, 1H), 7.17-7.21 (m, 2H), 7.26-7.30 (m, 4H), 7.41-7.42 (m, 4H). LC-MS (ESI) (m/z) 394.2 (M+1)$^+$.

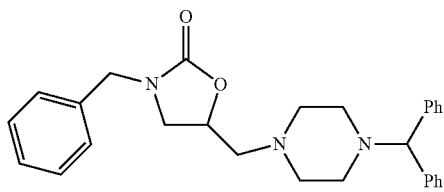 [SMILES: O=C1OC(CN2CCN(C(c3ccccc3)c3ccccc3)CC2)CN1Cc1ccccc1]

Preparation of 5-(4-benzhydryl-piperazin-1-ylmethyl)-3-benzyl-oxazolidin-2-one: The title compound was prepared according to the procedure for 5-((4-benzhydrylpiperazin-1-yl)methyl)-3-(4-fluorobenzyl)oxazolidin-2-one, except 3-benzyl-2-oxooxazolidin-5-yl)methyl 4-methylbenzenesulfonate was substituted for (3-(4-Fluorobenzyl)-2-oxooxazolidin-5-yl)methyl 4-methylbenzenesulfonate. $^1$H-NMR {CDCl$_3$, 400 MHz, δ (ppm)} 2.50 (bs, 4H), 2.71-2.95 (m, 6H), 3.05-3.09 (m, 1H), 3.50 (t, 1H), 3.99-4.13 (heptet, 1H), 4.24 (s, 1H), 4.39 (d, 2H), 4.73-4.80 (m, 1H), 7.15-7.22 (m, 2H), 7.24-7.41 (m, 13H). LC-MS (ESI) (m/z) 442.1 (M+1)$^+$.

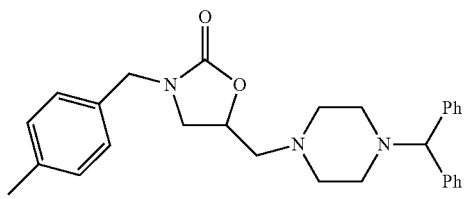 [SMILES: Cc1ccc(CN2CC(CN3CCN(C(c4ccccc4)c4ccccc4)CC3)OC2=O)cc1]

Preparation of 5-((4-benzhydrylpiperazin-1-yl)methyl)-3-(4-methylbenzyl)oxazolidin-2-one: The title compound was prepared according to the procedure for 5-((4-benzhy-drylpiperazin-1-yl)methyl)-3-(4-fluorobenzyl)oxazolidin-2-one, except 3-(4-methylbenzyl)-2-oxooxazolidin-5-yl) methyl 4-methylbenzenesulfonate was substituted for (3-(4-Fluorobenzyl)-2-oxooxazolidin-5-yl)methyl 4-methylbenzenesulfonate. $^1$H NMR: {CDCl$_3$, 400 MHz, δ (ppm)}2.37-2.68 (m, 13H), 3.13-3.17 (m, 1H), 3.43 (t, 1H), 4.21 (s, 1H), 4.34-4.43 (m, 2H), 4.56-4.63 (m, 1H), 7.17-7.21 (m, 6H), 7.26-7.30 (m, 4H), 7.40-7.42 (m, 4H). LC-MS (ESI) (m/z) 456.3 (M+1)$^+$.

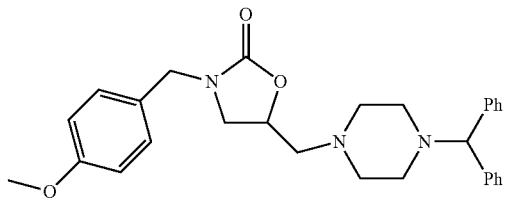 [SMILES: COc1ccc(CN2CC(CN3CCN(C(c4ccccc4)c4ccccc4)CC3)OC2=O)cc1]

Preparation of 5-((4-benzhydrylpiperazin-1-yl)methyl)-3-(4-methoxybenzyl)oxazolidin-2-one: The title compound was prepared according to the procedure for 5-((4-benzhydrylpiperazin-1-yl)methyl)-3-(4-fluorobenzyl)oxazolidin-2-one, except 3-(4-methoxybenzyl)-2-oxooxazolidin-5-yl) methyl 4-methylbenzenesulfonate was substituted for (3-(4-Fluorobenzyl)-2-oxooxazolidin-5-yl)methyl 4-methylbenzenesulfonate. $^1$H NMR: {CDCl$_3$, 400 MHz, δ (ppm)} 2.38-2.67 (m, 10H), 3.12-3.15 (m, 1H), 3.42 (t, 1H), 3.82 (s, 3H), 4.21 (s, 1H), 4.31-4.40 (s, 2H), 4.56-4.62 (m, 1H), 6.87-6.91 (m, 2H), 7.16-7.23 (m, 4H), 7.27-7.29 (m, 4H), 7.40-7.41 (m, 4H). LC-MS (ESI) (m/z) 472.2 (M+1)$^+$.

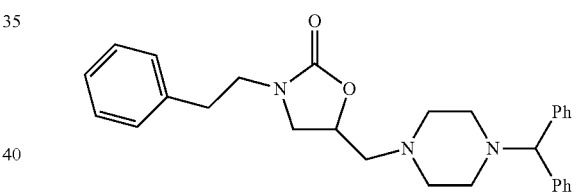

Preparation of 5-((4-benzhydrylpiperazin-1-yl)methyl)-3-phenethyloxazolidin-2-one: The title compound was prepared according to the procedure for 5-((4-benzhydrylpiperazin-1-yl)methyl)-3-(4-fluorobenzyl)oxazolidin-2-one, except 2-oxo-3-phenethyloxazolidin-5-yl)methyl 4-methylbenzenesulfonate was substituted for (3-(4-Fluorobenzyl)-2-oxooxazolidin-5-yl)methyl 4-methylbenzenesulfonate. $^1$H NMR: {CDCl$_3$, 400 MHz, δ (ppm)}2.40-2.63 (m, 10H), 2.87-2.91 (m, 2H), 3.12-3.16 (m, 1H), 3.42 (t, 1H), 3.51 (t, 1H), 4.22 (s, 1H), 4.50-4.57 (m, 1H), 7.17-7.33 (m, 11H), 7.40-7.42 (m, 4H). LC-MS (ESI) (m/z) 456.2 (M+1)$^+$.

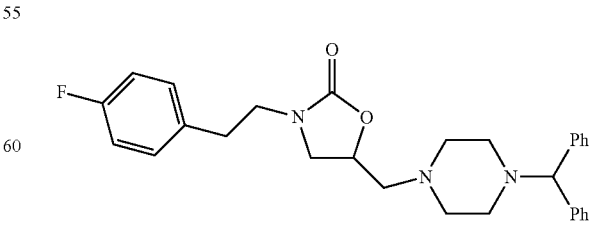

Preparation of 5-((4-benzhydrylpiperazin-1-yl)methyl)-3-(4-fluorophenethyl) oxazolidin-2-one: The title compound was prepared according to the procedure for 5-((4-benzhydrylpiperazin-1-yl)methyl)-3-(4-fluorobenzyl)oxazolidin-2-one, except (3-(4-fluorophenethyl)-2-oxooxazolidin-5-yl)methyl 4-methylbenzenesulfonate was substituted for 3-(4-Fluorobenzyl)-2-oxooxazolidin-5-yl)methyl-4-methylbenzenesulfonate. $^1$H NMR: {CDCl$_3$, 400 MHz, δ (ppm)} 2.30-2.53 (m, 10H), 2.75 (t, 2H), 3.03-3.07 (m, 1H), 3.30-3.41 (m, 3H), 4.12 (s, 1H), 4.40-4.47 (m, 1H), 6.87-6.92 (m, 2H), 7.05-7.10 (m, 4H), 7.16-7.19 (m, 4H), 7.30-7.32 (m, 4H). LC-MS (ESI) (m/z) 474.2 (M+1)$^+$.

drylpiperazin-1-yl)methyl)-3-(4-fluorobenzyl)oxazolidin-2-one, except (2-oxo-3-(3-phenylpropyl)oxazolidin-5-yl) methyl 4-methylbenzenesulfonate was substituted for (3-(4-Fluorobenzyl)-2-oxooxazolidin-5-yl)methyl 4-methylbenzenesulfonate. $^1$H NMR: {CDCl$_3$, 400 MHz, δ (ppm)} 1.75-1.82 (pentet, 2H), 2.31-2.58 (m, 12H), 3.13-3.27 (m, 3H), 3.43 (t, 1H), 4.10 (s, 1H), 4.44-4.50 (m, 1H), 7.07-7.14 (m, 5H), 7.16-7.23 (m, 6H), 7.30-7.32 (m, 4H). LC-MS (ESI) (m/z) 470.3 (M+1)$^+$.

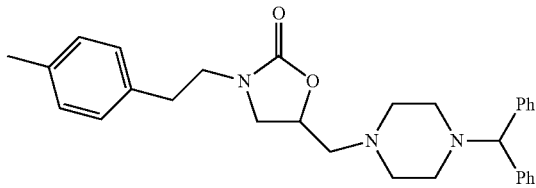 [SMILES: Cc1ccc(CCN2CC(CN3CCN(C(c4ccccc4)c4ccccc4)CC3)OC2=O)cc1]

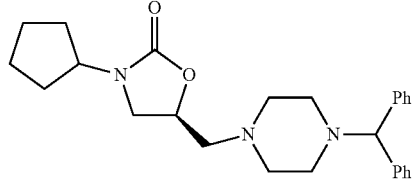

Preparation of 5-(4-Benzhydryl-piperazin-1-ylmethyl)-3-(2-p-tolyl-ethyl)-oxazolidin-2-one: The title compound was prepared according to the procedure for 5-((4-benzhydrylpiperazin-1-yl)methyl)-3-(4-fluorobenzyl)oxazolidin-2-one, except (3-(4-methylphenethyl)-2-oxooxazolidin-5-yl)methyl 4-methylbenzenesulfonate was substituted for (3-(4-Fluorobenzyl)-2-oxooxazolidin-5-yl)methyl 4-methylbenzenesulfonate. $^1$H NMR: {CDCl$_3$, 400 MHz, δ (ppm)} 2.23-2.53 (m, 13H), 2.72-2.77 (m, 2H), 3.02-3.06 (m, 1H), 3.32 (t, 1H), 3.40 (t, 2H), 4.12 (s, 1H), 4.40-4.47 (m, 1H), 7.07-7.11 (m, 2H), 7.16-7.20 (m, 4H), 7.30-7.33 (m, 4H). LC-MS (ESI) (m/z) 470.3 (M+1)$^+$.

Preparation of 5-(4-Benzhydryl-piperazin-1-ylmethyl)-3-cyclopentyl-oxazolidin-2-one: The title compound was prepared according to the procedure for 5-((4-benzhydrylpiperazin-1-yl)methyl)-3-(4-fluorobenzyl)oxazolidin-2-one, except (R)-(3-cyclopentyl-2-oxooxazolidin-5-yl)methyl 4-methylbenzenesulfonate was substituted for (3-(4-Fluorobenzyl)-2-oxooxazolidin-5-yl)methyl 4-methylbenzenesulfonate. $^1$H-NMR {CDCl$_3$, 400 MHz, δ (ppm)} 1.48-1.73 (6H), 1.83-1.91 (m, 2H), 2.42-2.71 (m, 10H), 3.23-3.27 (m, 1H), 3.54 (t, 1H), 4.19-4.29 (m, 2H), 4.58-4.64 (m, 1H), 7.17-7.21 (m, 2H), 7.26-7.30 (m, 4H), 7.40-7.42 (m, 4H). LC-MS (ESI) (m/z) 420.3 (M+1)$^+$.

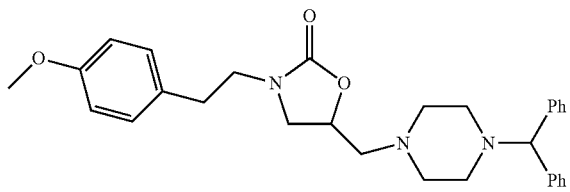 [SMILES: COc1ccc(CCN2CC(CN3CCN(C(c4ccccc4)c4ccccc4)CC3)OC2=O)cc1]

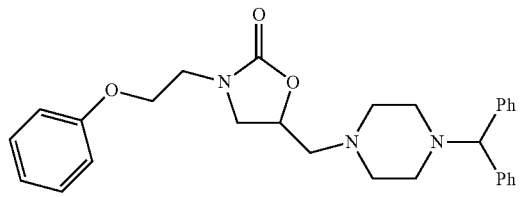

Preparation of 5-(4-Benzhydryl-piperazin-1-ylmethyl)-3-[2-(4-methoxy-phenyl)-ethyl]-oxazolidin-2-one: The title compound was prepared according to the procedure for 5-((4-benzhydrylpiperazin-1-yl)methyl)-3-(4-fluorobenzyl)oxazolidin-2-one, except (3-(4-methoxyphenethyl)-2-oxooxazolidin-5-yl)methyl 4-methylbenzenesulfonate was substituted for (3-(4-Fluorobenzyl)-2-oxooxazolidin-5-yl)methyl 4-methylbenzenesulfonate. $^1$H NMR: {CDCl$_3$, 400 MHz, δ (ppm)} 2.41-2.63 (m, 10H), 2.82 (t, 2H), 3.12-3.16 (m, 1H), 3.40-3.49 (m, 3H), 3.79 (s, 3H), 4.23 (m, 1H), 4.50-4.57 (m, 1H), 6.84-6.87 (m, 2H), 7.13-7.21 (m, 4H), 7.27-7.30 (m, 4H), 7.41-7.43 (m, 4H). LC-MS (ESI) (m/z) 486.3 (M+1)$^+$.

Preparation of 5-((4-benzhydrylpiperazin-1-yl)methyl)-3-(2-phenoxyethyl) oxazolidin-2-one: The title compound was prepared according to the procedure for 5-((4-benzhydrylpiperazin-1-yl)methyl)-3-(4-fluorobenzyl)oxazolidin-2-one, except (2-oxo-3-(2-phenoxyethyl)oxazolidin-5-yl) methyl 4-methylbenzenesulfonate was substituted for (3-(4-Fluorobenzyl)-2-oxooxazolidin-5-yl)methyl 4-methylbenzenesulfonate. $^1$H NMR: {CDCl$_3$, 400 MHz, δ (ppm)} 2.40-2.70 (m, 10H), 3.49-3.53 (m, 1H), 3.58-3.73 (m, 2H), 3.81 (t, 1H), 4.14-4.16 (m, 2H), 4.20 (s, 1H), 4.60-4.67 (m, 1H), 6.89-6.91 (m, 2H), 6.98-7.02 (m, 1H), 7.17-7.21 (m, 2H), 7.26-7.34 (m, 6H), 7.40-7.43 (m, 4H). LC-MS (ESI) (m/z) 472.2 (M+1)$^+$.

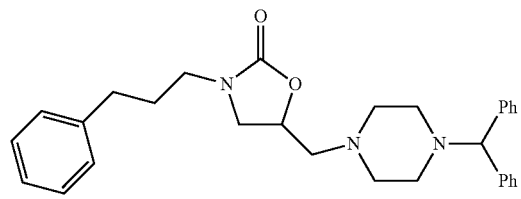 [SMILES: O=C1OC(CN2CCN(C(c3ccccc3)c3ccccc3)CC2)CN1CCCc1ccccc1]

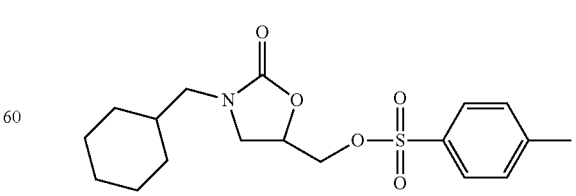

Preparation of 5-((4-benzhydrylpiperazin-1-yl)methyl)-3-(3-phenylpropyl) oxazolidin-2-one: The title compound was prepared according to the procedure for 5-((4-benzhy- Preparation of (3-(cyclohexylmethyl)-2-oxooxazolidin-5-yl)methyl 4-methylbenzenesulfonate: To a suspension of K$_2$CO$_3$ (2.5 g, 18.08 mmol) in anhydrous methanol (30 mL)

containing epibromohydrin (4.965 g, 36.24 mmol) was added the cyclohexyl methylamine (4.089 g, 36.12 mmol) and the reaction was stirred overnight. The reaction mixture was then filtered and the organic solvent was stripped off under reduced pressure to obtain a liquid residue which was used without purification.

p-Toluene sulfonyl chloride (13.5 g, 7.096 mmol) in methylene chloride (50 mL) was added dropwise to a chilled solution of crude alcohol (7.5756 g, 35.52 mmol) and triethylamine (7.1874 g, 71.028 mmol) in methylene chloride (60 mL). The reaction was stirred in ice at 0° C. for 1 hour followed by overnight stirring at room temperature. It was later quenched with ice water and the organic layer was washed successfully with 10% HCl, saturated aqueous sodium bicarbonate and brine. The organic layer was dried over MgSO$_4$ and concentrated under reduced pressure to obtain a solid/oil which was purified on silica gel redisep column using hexane: ethyl acetate (0-100%) to obtain pale yellow solid (2.9782 g, 22.81% yield). $^1$H-NMR {CDCl$_3$, 400 MHz, δ (ppm)} 0.89-0.99 (m, 2H), 1.11-1.28 (m, 3H), 1.47-1.61 (m, 1H), 1.63-1.74 (m, 6H), 2.47 (s, 3H), 3.00-3.11 (m, 2H), 3.42-3.46 (m, 1H), 3.63 (t, 1H), 4.11-4.18 (m, 2H), 4.66-4.71 (m, 1H), 7.35-7.39 (m, 2H), 7.79-7.81 (m, 2H). LC-MS (ESI) (m/z) 368.1 (M+1)$^+$.

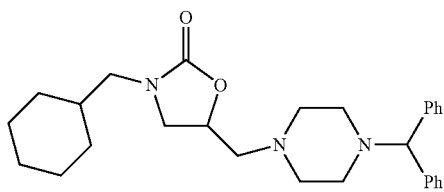

Preparation of 5-((4-benzhydrylpiperazin-1-yl)methyl)-3-(cyclohexylmethyl) oxazolidin-2-one: The Toluene-4-sulfonic acid 3-cyclohexylmethyl-2-oxo-oxazolidin-5-ylmethyl ester (1 g, 2.72 mmol) and diphenylmethylpiperazine and (1.37 g, 5.42 mmol) in anhydrous tetrahydrofuran (5 mL) and triethyl amine (1.099 g, 10.86 mmol) were stirred under microwave at 120° C. for 1 hour. After 1 hour, the solvent was stripped off, residue was dissolved in dichloromethane and purified by silica gel column using hexane-ethyl acetate (0-100%) to obtain creamish solid (0.8095 g, 66.45% yield). $^1$H NMR: {CDCl$_3$, 400 MHz, δ (ppm)} 0.92-1.01 (m, 2H), 1.12-1.29 (m, 3H), 1.52-1.76 (m, 7H), 2.42-2.70 (m, 10H), 3.02-3.11 (m, 2H), 3.28-3.32 (m, 1H), 3.57 (t, 1H), 4.22 (s, 1H), 4.58-4.70 (m, 1H), 7.17-7.21 (m, 2H), 7.26-7.30 (m, 4H), 7.40-7.42 (m, 4H). LC-MS (ESI) (m/z) 448.3 (M+1)$^+$.

Formulations

The present invention also relates to compositions or formulations which comprise the 5-hydroxytryptamine receptor 2b activity modulators according to the present invention. In general, the compositions of the present invention comprise an effective amount of one or more disubstituted oxazolidin-2-ones or pharmaceutically acceptable salt, solvate, prodrug or complex thereof according to the present invention which are effective for providing modulation of 5-hydroxytryptamine receptor 2b activity; and one or more excipients. The disubstituted oxazolidin-2-ones or pharmaceutically acceptable salt, solvate, prodrug or complex thereof in such formulations may comprise from 0.1 to 99.99 weight percent.

For the purposes of the present invention the term "excipient" and "carrier" are used interchangeably throughout the description of the present invention and said terms are defined herein as, "ingredients which are used in the practice of formulating a safe and effective pharmaceutical composition."

The formulator will understand that excipients are used primarily to serve in delivering a safe, stable, and functional pharmaceutical, serving not only as part of the overall vehicle for delivery but also as a means for achieving effective absorption by the recipient of the active ingredient. An excipient may fill a role as simple and direct as being an inert filler, or an excipient as used herein may be part of a pH stabilizing system or coating to insure delivery of the ingredients safely to the stomach. The formulator can also take advantage of the fact the compounds of the present invention have improved cellular potency, pharmacokinetic properties, as well as improved oral bioavailability.

The present teachings also provide pharmaceutical compositions that include at least one compound described herein and one or more pharmaceutically acceptable carriers, excipients, or diluents. Examples of such carriers are well known to those skilled in the art and can be prepared in accordance with acceptable pharmaceutical procedures, such as, for example, those described in *Remington's Pharmaceutical Sciences*, 17th edition, ed. Alfonoso R. Gennaro, Mack Publishing Company, Easton, Pa. (1985), the entire disclosure of which is incorporated by reference herein for all purposes. As used herein, "pharmaceutically acceptable" refers to a substance that is acceptable for use in pharmaceutical applications from a toxicological perspective and does not adversely interact with the active ingredient. Accordingly, pharmaceutically acceptable carriers are those that are compatible with the other ingredients in the formulation and are biologically acceptable. Supplementary active ingredients can also be incorporated into the pharmaceutical compositions.

Compounds of the present teachings can be administered orally or parenterally, neat or in combination with conventional pharmaceutical carriers. Applicable solid carriers can include one or more substances which can also act as flavoring agents, lubricants, solubilizers, suspending agents, fillers, glidants, compression aids, binders or tablet-disintegrating agents, or encapsulating materials. The compounds can be formulated in conventional manner, for example, in a manner similar to that used for known 5-hydroxytryptamine receptor 2b activity modulators. Oral formulations containing a compound disclosed herein can comprise any conventionally used oral form, including tablets, capsules, buccal forms, troches, lozenges and oral liquids, suspensions or solutions. In powders, the carrier can be a finely divided solid, which is an admixture with a finely divided compound. In tablets, a compound disclosed herein can be mixed with a carrier having the necessary compression properties in suitable proportions and compacted in the shape and size desired. The powders and tablets can contain up to 99% of the compound.

Capsules can contain mixtures of one or more compound(s) disclosed herein with inert filler(s) and/or diluent(s) such as pharmaceutically acceptable starches (e.g., corn, potato or tapioca starch), sugars, artificial sweetening agents, powdered celluloses (e.g., crystalline and microcrystalline celluloses), flours, gelatins, gums, and the like.

Useful tablet formulations can be made by conventional compression, wet granulation or dry granulation methods and utilize pharmaceutically acceptable diluents, binding agents, lubricants, disintegrants, surface modifying agents (including surfactants), suspending or stabilizing agents, including, but not limited to, magnesium stearate, stearic acid, sodium lauryl sulfate, talc, sugars, lactose, dextrin, starch, gelatin, cellulose, methyl cellulose, microcrystalline cellulose, sodium carboxymethyl cellulose, carboxymethylcellulose calcium, polyvinylpyrrolidine, alginic acid, acacia gum, xanthan gum, sodium citrate, complex silicates, calcium carbonate, glycine, sucrose, sorbitol, dicalcium phosphate, calcium sulfate, lactose, kaolin, mannitol, sodium chloride, low melting waxes, and ion exchange resins. Surface modifying agents include nonionic and anionic surface modifying agents. Representative examples of surface modifying agents include, but are not limited to, poloxamer 188, benzalkonium chloride, calcium stearate, cetostearl alcohol, cetomacrogol emulsifying wax, sorbitan esters, colloidal silicon dioxide, phosphates, sodium dodecylsulfate, magnesium aluminum silicate, and triethanolamine. Oral formulations herein can utilize standard delay or time-release formulations to alter the absorption of the compound(s). The oral formulation can also consist of administering a compound disclosed herein in water or fruit juice, containing appropriate solubilizers or emulsifiers as needed.

Liquid carriers can be used in preparing solutions, suspensions, emulsions, syrups, elixirs, and for inhaled delivery. A compound of the present teachings can be dissolved or suspended in a pharmaceutically acceptable liquid carrier such as water, an organic solvent, or a mixture of both, or a pharmaceutically acceptable oils or fats. The liquid carrier can contain other suitable pharmaceutical additives such as solubilizers, emulsifiers, buffers, preservatives, sweeteners, flavoring agents, suspending agents, thickening agents, colors, viscosity regulators, stabilizers, and osmo-regulators. Examples of liquid carriers for oral and parenteral administration include, but are not limited to, water (particularly containing additives as described herein, e.g., cellulose derivatives such as a sodium carboxymethyl cellulose solution), alcohols (including monohydric alcohols and polyhydric alcohols, e.g., glycols) and their derivatives, and oils (e.g., fractionated coconut oil and arachis oil). For parenteral administration, the carrier can be an oily ester such as ethyl oleate and isopropyl myristate. Sterile liquid carriers are used in sterile liquid form compositions for parenteral administration. The liquid carrier for pressurized compositions can be halogenated hydrocarbon or other pharmaceutically acceptable propellants.

Liquid pharmaceutical compositions, which are sterile solutions or suspensions, can be utilized by, for example, intramuscular, intraperitoneal or subcutaneous injection. Sterile solutions can also be administered intravenously. Compositions for oral administration can be in either liquid or solid form.

Preferably the pharmaceutical composition is in unit dosage form, for example, as tablets, capsules, powders, solutions, suspensions, emulsions, granules, or suppositories. In such form, the pharmaceutical composition can be sub-divided in unit dose(s) containing appropriate quantities of the compound. The unit dosage forms can be packaged compositions, for example, packeted powders, vials, ampoules, prefilled syringes or sachets containing liquids. Alternatively, the unit dosage form can be a capsule or tablet itself, or it can be the appropriate number of any such compositions in package form. Such unit dosage form can contain from about 1 mg/kg of compound to about 500 mg/kg of compound, and can be given in a single dose or in two or more doses. Such doses can be administered in any manner useful in directing the compound(s) to the recipient's bloodstream, including orally, via implants, parenterally (including intravenous, intraperitoneal and subcutaneous injections), rectally, vaginally, and transdermally.

When administered for the treatment or inhibition of a particular disease state or disorder, it is understood that an effective dosage can vary depending upon the particular compound utilized, the mode of administration, and severity of the condition being treated, as well as the various physical factors related to the individual being treated. In therapeutic applications, a compound of the present teachings can be provided to a patient already suffering from a disease in an amount sufficient to cure or at least partially ameliorate the symptoms of the disease and its complications. The dosage to be used in the treatment of a specific individual typically must be subjectively determined by the attending physician. The variables involved include the specific condition and its state as well as the size, age and response pattern of the patient.

In some cases it may be desirable to administer a compound directly to the airways of the patient, using devices such as, but not limited to, metered dose inhalers, breath-operated inhalers, multidose dry-powder inhalers, pumps, squeeze-actuated nebulized spray dispensers, aerosol dispensers, and aerosol nebulizers. For administration by intranasal or intrabronchial inhalation, the compounds of the present teachings can be formulated into a liquid composition, a solid composition, or an aerosol composition. The liquid composition can include, by way of illustration, one or more compounds of the present teachings dissolved, partially dissolved, or suspended in one or more pharmaceutically acceptable solvents and can be administered by, for example, a pump or a squeeze-actuated nebulized spray dispenser. The solvents can be, for example, isotonic saline or bacteriostatic water. The solid composition can be, by way of illustration, a powder preparation including one or more compounds of the present teachings intermixed with lactose or other inert powders that are acceptable for intrabronchial use, and can be administered by, for example, an aerosol dispenser or a device that breaks or punctures a capsule encasing the solid composition and delivers the solid composition for inhalation. The aerosol composition can include, by way of illustration, one or more compounds of the present teachings, propellants, surfactants, and co-solvents, and can be administered by, for example, a metered device. The propellants can be a chlorofluorocarbon (CFC), a hydrofluoroalkane (HFA), or other propellants that are physiologically and environmentally acceptable.

Compounds described herein can be administered parenterally or intraperitoneally. Solutions or suspensions of these compounds or a pharmaceutically acceptable salts, hydrates, or esters thereof can be prepared in water suitably mixed with a surfactant such as hydroxyl-propylcellulose. Dispersions can also be prepared in glycerol, liquid polyethylene glycols, and mixtures thereof in oils. Under ordinary conditions of storage and use, these preparations typically contain a preservative to inhibit the growth of microorganisms.

The pharmaceutical forms suitable for injection can include sterile aqueous solutions or dispersions and sterile powders for the extemporaneous preparation of sterile injectable solutions or dispersions. In some embodiments, the form can sterile and its viscosity permits it to flow through a syringe. The form preferably is stable under the conditions of manufacture and storage and can be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), suitable mixtures thereof, and vegetable oils.

Compounds described herein can be administered transdermally, i.e., administered across the surface of the body and the inner linings of bodily passages including epithelial and mucosal tissues. Such administration can be carried out using the compounds of the present teachings including pharmaceutically acceptable salts, hydrates, or esters thereof, in lotions, creams, foams, patches, suspensions, solutions, and suppositories (rectal and vaginal).

Transdermal administration can be accomplished through the use of a transdermal patch containing a compound, such as a compound disclosed herein, and a carrier that can be inert to the compound, can be non-toxic to the skin, and can allow delivery of the compound for systemic absorption into the blood stream via the skin. The carrier can take any number of forms such as creams and ointments, pastes, gels, and occlusive devices. The creams and ointments can be viscous liquid or semisolid emulsions of either the oil-in-water or water-in-oil type. Pastes comprised of absorptive powders dispersed in petroleum or hydrophilic petroleum containing the compound can also be suitable. A variety of occlusive devices can be used to release the compound into the blood stream, such as a semi-permeable membrane covering a reservoir containing the compound with or without a carrier, or a matrix containing the compound. Other occlusive devices are known in the literature.

Compounds described herein can be administered rectally or vaginally in the form of a conventional suppository. Suppository formulations can be made from traditional materials, including cocoa butter, with or without the addition of waxes to alter the suppository's melting point, and glycerin. Water-soluble suppository bases, such as polyethylene glycols of various molecular weights, can also be used.

Lipid formulations or nanocapsules can be used to introduce compounds of the present teachings into host cells either in vitro or in vivo. Lipid formulations and nanocapsules can be prepared by methods known in the art.

To increase the effectiveness of compounds of the present teachings, it can be desirable to combine a compound with other agents effective in the treatment of the target disease. For example, other active compounds (i.e., other active ingredients or agents) effective in treating the target disease can be administered with compounds of the present teachings. The other agents can be administered at the same time or at different times than the compounds disclosed herein.

Compounds of the present teachings can be useful for the treatment or inhibition of a pathological condition or disorder in a mammal, for example, a human subject. The present teachings accordingly provide methods of treating or inhibiting a pathological condition or disorder by providing to a mammal a compound of the present teachings including its pharmaceutically acceptable salt) or a pharmaceutical composition that includes one or more compounds of the present teachings in combination or association with pharmaceutically acceptable carriers. Compounds of the present teachings can be administered alone or in combination with other therapeutically effective compounds or therapies for the treatment or inhibition of the pathological condition or disorder.

Non-limiting examples of compositions according to the present invention include from about 0.001 mg to about 1000 mg of one or more disubstituted oxazolidin-2-ones according to the present invention and one or more excipients; from about 0.01 mg to about 100 mg of one or more disubstituted oxazolidin-2-ones according to the present invention and one or more excipients; and from about 0.1 mg to about 10 mg of one or more disubstituted oxazolidin-2-ones according to the present invention; and one or more excipients.

Procedures

The following procedures can be utilized in evaluating and selecting compounds as 5-hydroxytryptamine receptor 2b activity modulators.

Radiolabel Binding Studies for Serotonin $5HT_{2b}$ Receptors, Method 1

A solution of the compound of the disclosure to be tested is prepared as a 1-mg/ml stock in Assay Buffer (50 mM Tris-HCl, 10 mM $MgCl_2$, 1 mM EDTA, pH 7.4) or DMSO according to its solubility. A 1-mg/ml stock of the reference compound 5-hydroxytryptamine (5-HT) is also prepared as a positive control. Eleven dilutions (5× assay concentration) of the compound of the disclosure and 5-HT are prepared in the Assay Buffer by serial dilution to yield final corresponding assay concentrations ranging from 10 μM to 10 μM.

A stock concentration of 5 nM [$^3$H]LSD (lysergic acid diethyl amide) is prepared in Assay Buffer. Aliquots (50 μl) of radioligand are dispensed into the wells of a 96-well plate containing 100 μl of Assay Buffer. Duplicate 50-μl aliquots of the compound of the disclosure test and 5-HT positive control reference compound serial dilutions are added.

Membrane fractions of cells expressing recombinant $5HT_{2B}$ receptors (50 μL) are dispensed into each well. The membranes are prepared from stably transfected c ell lines expressing $5HT_{2B}$ receptors cultured on 10-cm plates by harvesting PBS-rinsed monolayers, resuspending and lysing the monolayers in chilled, hypotonic 50 mM Tris-HCl, pH 7.4, centrifuging at 20,000×g, decanting the supernatant and storing at −80° C. The membrane preparations are resuspended in 3 ml of chilled Assay Buffer and homogenized by several passages through a 26 gauge needle before use in the assay.

The 250-μl reactions are incubated at room temperature for 1.5 hours, then harvested by rapid filtration onto 0.3% polyethyleneimine-treated, 96-well filter mats using a 96-well Filtermate harvester. Four rapid 500-μl washes are performed with chilled Assay Buffer to reduce non-specific binding. The filter mats are dried, then scintillant is added to the filters and the radioactivity retained on the filters is counted in a scintillation counter.

Raw data (dpm) representing total radioligand binding (i.e., specific+non-specific binding) are plotted as a function of the logarithm of the molar concentration of the competitor (i.e., test or reference compound). Non-linear regression of the normalized (i.e., percent radioligand binding compared to that observed in the absence of test or reference compound) raw data is performed in 4.0 (GraphPad Software, Inc.) using the built-in three parameter logistic model describing ligand competition binding to radioligand-labeled sites:

$$y = \text{bottom} + [(\text{top}-\text{bottom})/(1+10^{x-\log IC_{50}})]$$

where "bottom" is the residual radioligand binding measured in the presence of 10 μM reference compound (i.e., non-specific binding) and "top" is the total radioligand binding observed in the absence of competitor. The log $IC_{50}$ (i.e., the log of the ligand concentration that reduces radioligand binding by 50%) is thus estimated from the data and used to obtain the Ki by applying the Cheng-Prusoff approximation:

$$Ki=IC_{50}/(1+[ligand]/KD)$$

where "[ligand]" is the assay radioligand concentration and "KD" is the affinity constant of the radioligand for the target receptor.

Compounds of the disclosure are also screened at a single concentration of 10 µM using the same method described for the Radiolabel Binding Studies for Serotonin $5HT_{2B}$ receptors, method 1 to determine the percent inhibition of [$^3$H] LSD binding.

Radiolabel Binding Studies for Serotonin $5HT_{2h}$ Receptors, Method 2

The following alternative procedure is utilized in evaluating a compound's ability to modulate $5HT_{2B}$ receptor reactivity.

A solution of the compound of the disclosure to be tested is prepared as a 1-mg/ml stock in Assay Buffer or DMSO according to its solubility. A 1-mg/ml stock of the reference compound 5-hydroxytryptamine (5-HT) is also prepared as a positive control. Eleven dilutions (5× assay concentration) of the compound of the disclosure and 5-HT are prepared in the Assay Buffer by serial dilution to yield final corresponding assay concentrations ranging from 10 µM to 10 µM.

A stock concentration of 5 nM [$^3$H]-5-Hydroxytryptamine ([$^3$H]-5HT) is prepared in the Assay Buffer. Aliquots (50 µl) of radioligand are dispensed into the wells of a 96-well plate containing 100 µl of Assay Buffer. Duplicate 50-µl aliquots of the compound of the disclosure test and 5-HT positive control reference compound serial dilutions are added.

Membrane fractions of cells expressing recombinant $5HT_{2B}$ receptors (50 µL) are dispensed into each well. The membranes are prepared from stably transfected c ell lines expressing $5HT_{2B}$ receptors cultured on 10-cm plates by harvesting PBS-rinsed monolayers, resuspending and lysing the monolayers in chilled, hypotonic 50 mM Tris-HCl, pH 7.4, centrifuging at 20,000×g, decanting the supernatant and storing at −80° C. The membrane preparations are resuspended in 3 ml of chilled Assay Buffer and homogenized by several passages through a 26 gauge needle before using in the assay.

The 250-µl reactions are incubated at room temperature for 1.5 hours, then harvested by rapid filtration onto 0.3% polyethyleneimine-treated, 96-well filter mats using a 96-well Filtermate harvester. Four rapid 500-µl washes are performed with chilled Assay Buffer to reduce non-specific binding. The filter mats are dried, then scintillant is added to the filters and the radioactivity retained on the filters is counted in a Microbeta scintillation counter.

Raw data (dpm) representing total radioligand binding (i.e., specific+non-specific binding) are plotted as a function of the logarithm of the molar concentration of the competitor (i.e., test or reference compound). Non-linear regression of the normalized (i.e., percent radioligand binding compared to that observed in the absence of test or reference compound) raw data is performed in 4.0 (GraphPad Software, Inc.) using the built-in three parameter logistic model describing ligand competition binding to radioligand-labeled sites:

$$y=bottom+[(top-bottom)/(1+10x-\log IC_{50})]$$

where "bottom" is the residual radioligand binding measured in the presence of 10 µM reference compound (i.e., non-specific binding) and "top" is the total radioligand binding observed in the absence of competitor. The log $IC_{50}$ (i.e., the log of the ligand concentration that reduces radioligand binding by 50%) is thus estimated from the data and used to obtain the Ki by applying the Cheng-Prusoff approximation:

$$Ki=IC_{50}/(1+[ligand]/KD)$$

where "[ligand]" is the assay radioligand concentration and "KD" is the affinity constant of the radioligand for the target receptor.

Compounds of the disclosure are also screened at a single concentration of 10 µM using the same method described for the Radiolabel Binding Studies for Serotonin $5HT_{2B}$ receptors, method 2 to determine the percent inhibition of [$^3$H]-5HT binding.

TABLE 5

Radiolabel Binding Studies for Serotonin $5HT_{2B}$ receptors results for exemplary compounds of the disclosure using method 1

| Entry | Structure | $5\text{-HT}_{2B}$ % inhib @10 uM | $5\text{-HT}_{2B}$ $IC_{50}$ nM |
|---|---|---|---|
| 1 | 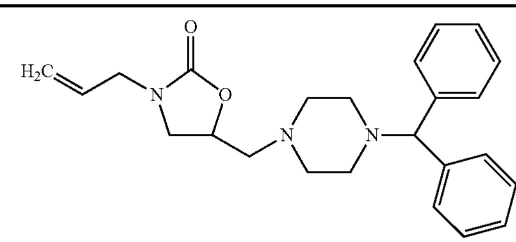 | 91.1 | 126 |
| 2 | 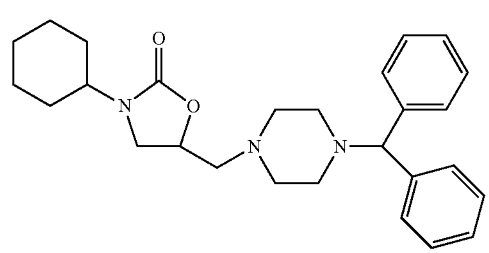 [SMILES: O=C1OC(CN2CCN(C(c3ccccc3)c3ccccc3)CC2)CN1C1CCCCC1] | 91.4 | |

TABLE 5-continued

Radiolabel Binding Studies for Serotonin 5HT$_{2B}$ receptors results for exemplary compounds of the disclosure using method 1

| Entry | Structure | 5-HT$_{2B}$ % inhib @10 uM | 5-HT$_{2B}$ IC$_{50}$ nM |
|---|---|---|---|
| 3 | 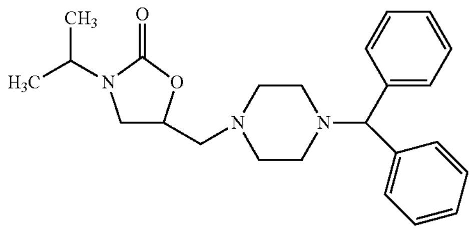 [SMILES: CC(C)N1CC(CN2CCN(C(c3ccccc3)c3ccccc3)CC2)OC1=O] | 84.9 | 274 |
| 4 | 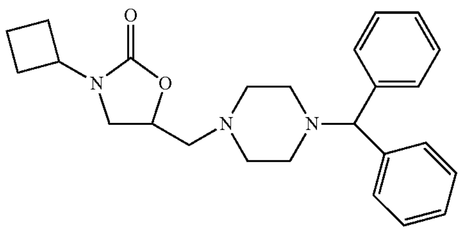 [SMILES: O=C1OC(CN2CCN(C(c3ccccc3)c3ccccc3)CC2)CN1C1CCC1] | 87.3 | 190 |
| 5 | 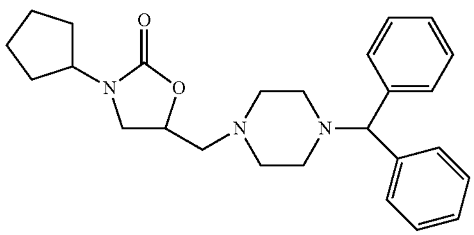 [SMILES: O=C1OC(CN2CCN(C(c3ccccc3)c3ccccc3)CC2)CN1C1CCCC1] | 94.1 | 41 |
| 6 | 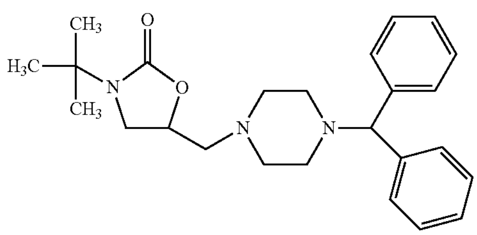 [SMILES: CC(C)(C)N1CC(CN2CCN(C(c3ccccc3)c3ccccc3)CC2)OC1=O] | 59.3 | 1871 |
| 7 | 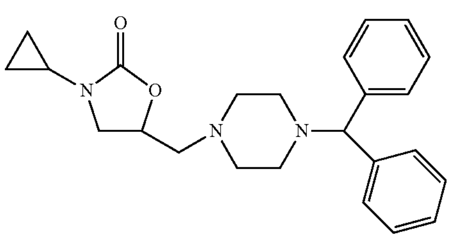 [SMILES: O=C1OC(CN2CCN(C(c3ccccc3)c3ccccc3)CC2)CN1C1CC1] | 87.6 | 298 |

Functional Serotonin 5HT$_{2B}$ Assay, Method 1

The following assay is used to determine 5HT$_{2B}$ receptor agonist or antagonist activity of a test compound.

Cell lines stably expressing human 5HT$_{2B}$ receptors are seeded in glass-bottom 96- or 384-well, poly-L-lysine-coated plates 48 hours prior to the assay (40,000 cells per well or 6,700 cells, respectively) in Dulbecco's Modified Eagle Medium (DMEM) containing 5% dialyzed serum. Twenty hours prior to the assay, the medium is changed to serum-free DMEM. Then, the cells are preincubated in 30 µl (96-well plates) or 20 µl (384-well plates) of calcium dye-containing assay buffer (1× Hanks Balanced Salt Solution, 20 mM HEPES, 2.5 mM probenecid, pH 7.4) at 37° C. for 75 minutes in a humidified incubator. During that time, serial dilutions of methysergide and compounds of the disclosure are made at 2× assay concentration (final assay concentrations ranging from 0.1 nM to 10 µM). Just prior to the assay, the plates are allowed to cool to room temperature for 10 minutes and then are transferred to a FLIPR Tetra fluorescence image plate reader (Molecular Devices). Basal fluorescence (excitation 488 nm, emission 510-570 nm) is measured for 20 seconds, then test compound or reference agonist dilutions (2× assay concentration) are added (30 µl for 96-well plates, 20 µl for 384-well plates, each concentration assayed in triplicate) and fluorescence is measured for 60 seconds. The maximum fluorescence values during the baseline and test compound or reference agonist addition phases (for agonist assays) are exported for analysis.

For agonist tests, raw data (maximum fluorescence, fluorescence units) for each concentration of compounds of the disclosure or methysergide are normalized to the baseline fluorescence (reported as fold increase over basal) and plotted as a function of the logarithm of the molar concentration of the drug (i.e., test or reference compound). Non-linear regression of the normalized data is performed in Prism 4.0 (GraphPad Software, Inc.) using the built-in three parameter logistic model (i.e., sigmoidal concentration-response) describing agonist-stimulated activation of one receptor population:

$$y = \text{bottom} + [(\text{top} - \text{bottom})/(1 + 10^{x - \log EC_{50}})]$$

where "bottom" is the best-fit basal fluorescence and "top" is the best-fit maximal fluorescence stimulated by the test compound or reference agonist. The log $EC_{50}$ (i.e., the log of the drug concentration that increases fluorescence by 50% of the maximum fluorescence observed for the test compound or reference agonist) is thus estimated from the data, and the $EC_{50}$ (agonist potency) is obtained. To obtain an estimate of the relative efficacy of the test compound (Rel. Emax), its best-fit top is compared to and expressed as a ratio of that for the reference agonist (Rel. Emax of the reference agonist is 1.00).

To ascertain whether test compounds are antagonists, a double-addition paradigm is employed. After measuring baseline fluorescence for 20 seconds, 30 µl of compound of the disclosure (20 µM) is added (10 µM final concentration, assayed in triplicate) and fluorescence is measured for an additional 15 min. Then, 30 µl of methysergide (3×; $EC_{90}$) is added (final concentration of agonist is EC30) and fluorescence is measured for 60 seconds. Maximum baseline-normalized fluorescence evoked by methysergide in the presence of a compound of the disclosure is compared to the maximum baseline-normalized fluorescence elicited by methysergide following addition of vehicle instead of test compound and expressed as a ratio. "Hits" (compounds that antagonize reference agonist-stimulated increases in baseline-normalized fluorescence by at least 50%) are then characterized by a modified Schild analysis.

For modified Schild analysis, a family of methysergide concentration-response isotherms is generated in the absence and presence of graded concentrations of a compound of the disclosure (added 15 min prior to reference agonist). Theoretically, compounds that are competitive antagonists cause a dextral shift of agonist concentration-response isotherms without reducing the maximum response to agonist (i.e., surmountable antagonism). However, on occasion, factors such as non-competitive antagonism, hemiequilibria, and/or receptor reserve cause apparent insurmountable antagonism. To account for such deviations, the modified Lew-Angus method is employed to ascertain antagonist potency (Christopoulos et al., *Biochem Pharmacol.*, 1999, 58(5):735-48). Briefly, equieffective concentrations of agonist (concentrations of agonist that elicit a response equal to the EC25% of the agonist control curve) are plotted as a function of the test compound concentration present in the wells in which they were measured. Non-linear regression of the baseline-normalized data is performed in Prism 4.0 using the following equation:

$$pEC25\% = -\log([B] + 10^{-pK}) - \log c$$

where EC25% is the concentration of agonist that elicits a response equal to 25% of the maximum agonist control curve response and "[B]" is the antagonist concentration; "K", "c", and "s" are fit parameters. The parameter "s" is equal to the Schild slope factor. If "s" is not significantly different from unity, pK equals pKB. Otherwise, pA2 is calculated (pA2=pK/s). The parameter "c" is the ratio EC25%/[B].

Functional Serotonin $5HT_{2B}$ Assay, Method 2

The following alternative assay is used to determine $5HT_{2B}$ receptor agonist or antagonist activity of a test compound.

CHOK1 receptors stably expressing human $5HT_{2B}$ receptors are grown in DMEM supplemented with 10% FBS, 100 U/mL penicillin, 100 ug/ml streptomycin, 2 mM glutamine, 0.5 mg/mL G418 at 37° C. and 5% $CO_2$. Cells are plated at 40K/well in Becton-Dickinson 384-well poly-D-lysine coated plates using a Multidrop cell dispenser and grown overnight at 37° C. and 6% $CO_2$. The following day, cells are washed 3×100 µl, Assay buffer (HBSS containing 20 mM HEPES, 2.5 mM Probenecid and 0.1% BSA. Cells are incubated with 2 µM Fluo-4AM in the presence of 0.02% Pluronic acid in assay buffer for 1 hour at 37° C. and 6% $CO_2$. Compounds of the disclosure were serially diluted in 100% DMSO and then diluted in assay buffer to a 3× stock at 2% DMSO. This stock is then applied to the cells for a final DMSO concentration of 0.67%. For potency determination, the cells are preincubated with various concentrations of a compound of the disclosure (assay concentrations ranging from 0.1 nM to 10 µM) for 5 minutes and then stimulated for 3 minutes with an $EC_{70}$ concentration of 5-Carboxamidotryptamine (5-CT). The peak of the calcium response is used to construct concentration response curves. Potency ($EC_{50}$ and/or $IC_{50}$) are calculated with GraphPad/Prism.

All references cited herein are incorporated by reference. The present invention may be embodied in other specific forms without departing from the spirit or essential attributes thereof and, accordingly, reference should be made to the appended claims, rather than to the foregoing specification, as indicating the scope of the invention.

What is claimed is:
1. A compound having formula (I):

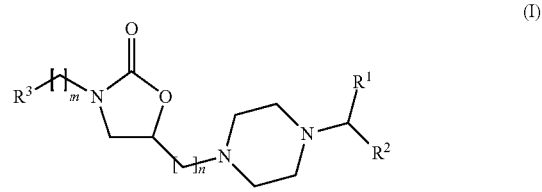

or pharmaceutically acceptable salt thereof, wherein:
$R^1$ is selected from a group consisting of hydrogen, linear $C_1$-$C_6$ alkyl, branched $C_1$-$C_6$ alkyl, and optionally substituted aryl having 0-5 substituents;
$R^2$ is unsubstituted aryl;
$R^3$ is selected from a group consisting of linear $C_1$-$C_6$ alkyl, branched $C_1$-$C_6$ alkyl, $C_3$-$C_7$ cycloalkyl, linear $C_1$-$C_6$ alkenyl, branched $C_1$-$C_6$ alkenyl, optionally substituted aryl having 0-5 substituents; optionally substituted heteroaryl having 0-5 substituents;

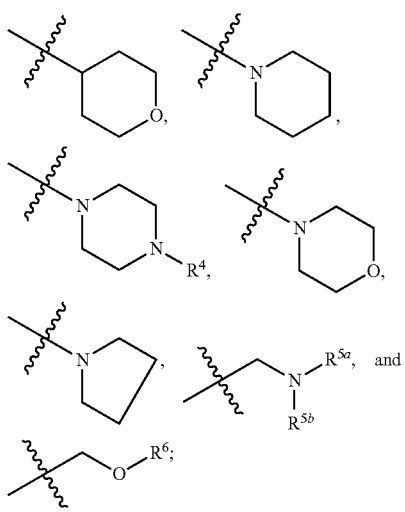

R⁴ is selected from a group consisting of hydrogen, linear $C_1$-$C_6$ alkyl, and branched $C_1$-$C_6$ alkyl;
R⁵ᵃ is selected from a group consisting of hydrogen, linear $C_1$-$C_6$ alkyl, and branched $C_1$-$C_6$ alkyl;
R⁵ᵇ is selected from a group consisting of hydrogen, linear $C_1$-$C_6$ alkyl, and branched $C_1$-$C_6$ alkyl;
R⁶ is selected from a group consisting of hydrogen, linear $C_1$-$C_6$ alkyl, branched $C_1$-$C_6$ alkyl, and optionally substituted aryl having 0-5 substituents;
m is 0, 1, 2 or 3; and
n is 1, 2, or 3.

2. A compound having formula (II):

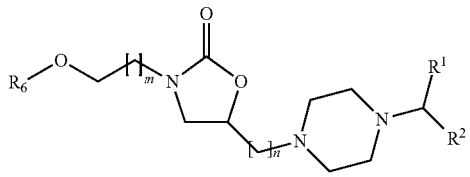

(II)

or pharmaceutically acceptable salt thereof, wherein:
R¹ is selected from a group consisting of hydrogen, linear $C_1$-$C_6$ alkyl, branched $C_1$-$C_6$ alkyl, and optionally substituted aryl having 0-5 substituents;
R² is optionally substituted aryl having 0-5 substituents;
R⁶ is selected from a group consisting of hydrogen, linear $C_1$-$C_6$ alkyl, branched $C_1$-$C_6$ alkyl, and optionally substituted aryl having 0-5 substituents;
m is 0, 1, 2 or 3; and
n is 1, 2, or 3.

3. A compound having formula (III):

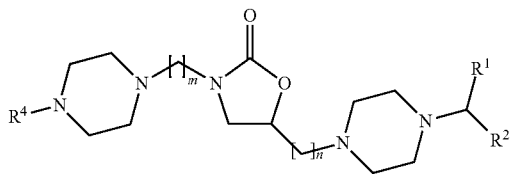

(III)

or pharmaceutically acceptable salt thereof, wherein:
R¹ is selected from a group consisting of hydrogen, linear $C_1$-$C_6$ alkyl, branched $C_1$-$C_6$ alkyl, and optionally substituted aryl having 0-5 substituents;
R² is optionally substituted aryl having 0-5 substituents;
R⁴ is selected from a group consisting of hydrogen, linear $C_1$-$C_6$ alkyl, and branched $C_1$-$C_6$ alkyl;
m is 0, 1, 2 or 3; and
n is 1, 2, or 3.

4. A compound having formula (IV):

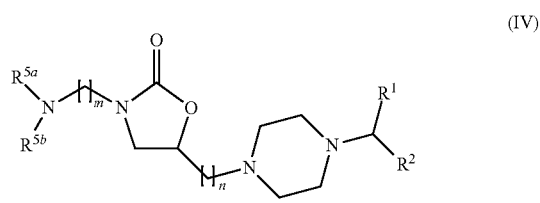

(IV)

or pharmaceutically acceptable salt thereof, wherein:
R¹ is selected from a group consisting of hydrogen, linear $C_1$-$C_6$ alkyl, branched $C_1$-$C_6$ alkyl, and optionally substituted aryl having 0-5 substituents;
R² is optionally substituted aryl having 0-5 substituents;
R⁵ᵃ is selected from a group consisting of hydrogen, linear $C_1$-$C_6$ alkyl, and branched $C_1$-$C_6$ alkyl;
R⁵ᵇ is selected from a group consisting of hydrogen, linear $C_1$-$C_6$ alkyl, and branched $C_1$-$C_6$ alkyl;
m is 0, 1, 2 or 3; and
n is 1, 2, or 3.

5. A compound according to claim 1 that is:
5-(4-benzhydryl-piperazin-1-ylmethyl)-3-isopropyl-oxazolidin-2-one;
3-allyl-5-(4-benzhydryl-piperazin-1-ylmethyl)-oxazolidin-2-one;
5-(4-benzhydryl-piperazin-1-ylmethyl)-3-tert-butyl-oxazolidin-2-one;
5-(4-benzhydryl-piperazin-1-ylmethyl)-3-cyclopropyl-oxazolidin-2-one;
5-(4-benzhydryl-piperazin-1-ylmethyl)-3-cyclobutyl-oxazolidin-2-one;
5-(4-benzhydryl-piperazin-1-ylmethyl)-3-cyclopentyl-oxazolidin-2-one;
5-(4-benzhydryl-piperazin-1-ylmethyl)-3-cyclohexyl-oxazolidin-2-one;
5-((4-benzhydrylpiperazin-1-yl)methyl)-3-phenyloxazolidin-2-one;
5-(4-benzhydryl-piperazin-1-ylmethyl)-3-cyclopentyl-oxazolidin-2-one;
5-((4-benzhydrylpiperazin-1-yl)methyl)-3-(4-fluorobenzyl)oxazolidin-2-one;
5-(4-benzhydryl-piperazin-1-ylmethyl)-3-(tetrahydropyran-4-ylmethyl)-oxazolidin-2-one;
5-((4-benzhydrylpiperazin-1-yl)methyl)-3-(2-morpholinoethyl)oxazolidin-2-one;
5-(4-benzhydryl-piperazin-1-ylmethyl)-3-propyl-oxazolidin-2-one;
5-(4-benzhydryl-piperazin-1-ylmethyl)-3-benzyl-oxazolidin-2-one;
5-((4-benzhydrylpiperazin-1-yl)methyl)-3-(4-fluorobenzyl)oxazolidin-2-one;
5-((4-benzhydrylpiperazin-1-yl)methyl)-3-(4-methylbenzyl)oxazolidin-2-one;
5-((4-benzhydrylpiperazin-1-yl)methyl)-3-(4-methoxybenzyl)oxazolidin-2-one;

5-((4-benzhydrylpiperazin-1-yl)methyl)-3-phenethyloxazolidin-2-one;
5-((4-benzhydrylpiperazin-1-yl)methyl)-3-(4-fluorophenethyl)oxazolidin-2-one;
5-(4-benzhydryl-piperazin-1-ylmethyl)-3-(2-p-tolylethyl)-oxazolidin-2-one;
5-(4-benzhydryl-piperazin-1-ylmethyl)-3-[2-(4-methoxyphenyl)-ethyl]-oxazolidin-2-one;
5-((4-benzhydrylpiperazin-1-yl)methyl)-3-(3-phenylpropyl)oxazolidin-2-one;
5-(4-benzhydryl-piperazin-1-ylmethyl)-3-cyclopentyl-oxazolidin-2-one;
5-((4-benzhydrylpiperazin-1-yl)methyl)-3-(2-phenoxyethyl)oxazolidin-2-one;
5-((4-benzhydrylpiperazin-1-yl)methyl)-3-(cyclohexylmethyl)oxazolidin-2-one;
or a pharmaceutically acceptable salt thereof.

6. A composition comprising an effective amount of at least one compound according to claim 1, or a pharmaceutically acceptable salt thereof.

7. A composition according to claim 6, further comprising at least one excipient.

8. A composition according to claim 7, wherein the at least one compound is at least one member selected from the group consisting of:
5-(4-Benzhydryl-piperazin-1-ylmethyl)-3-isopropyl-oxazolidin-2-one;
3-allyl-5-(4-benzhydryl-piperazin-1-ylmethyl)-oxazolidin-2-one;
5-(4-benzhydryl-piperazin-1-ylmethyl)-3-tert-butyl-oxazolidin-2-one;
5-(4-benzhydryl-piperazin-1-ylmethyl)-3-cyclopropyl-oxazolidin-2-one;
5-(4-benzhydryl-piperazin-1-ylmethyl)-3-cyclobutyl-oxazolidin-2-one;
5-(4-benzhydryl-piperazin-1-ylmethyl)-3-cyclopentyl-oxazolidin-2-one;
5-(4-benzhydryl-piperazin-1-ylmethyl)-3-cyclohexyl-oxazolidin-2-one;
5-((4-benzhydrylpiperazin-1-yl)methyl)-3-phenyloxazolidin-2-one;
5-(4-Benzhydryl-piperazin-1-ylmethyl)-3-cyclopentyl-oxazolidin-2-one;
5-((4-benzhydrylpiperazin-1-yl)methyl)-3-(4-fluorobenzyl)oxazolidin-2-one;
5-(4-Benzhydryl-piperazin-1-ylmethyl)-3-(tetrahydropyran-4-ylmethyl)-oxazolidin-2-one;
5-((4-benzhydrylpiperazin-1-yl)methyl)-3-(2-morpholinoethyl)oxazolidin-2-one;
5-(4-Benzhydryl-piperazin-1-ylmethyl)-3-propyl-oxazolidin-2-one;
5-(4-benzhydryl-piperazin-1-ylmethyl)-3-benzyl-oxazolidin-2-one;
5-((4-benzhydrylpiperazin-1-yl)methyl)-3-(4-fluorobenzyl)oxazolidin-2-one;
5-((4-benzhydrylpiperazin-1-yl)methyl)-3-(4-methylbenzyl)oxazolidin-2-one;
5-((4-benzhydrylpiperazin-1-yl)methyl)-3-(4-methoxybenzyl)oxazolidin-2-one;
5-((4-benzhydrylpiperazin-1-yl)methyl)-3-phenethyloxazolidin-2-one;
5-((4-benzhydrylpiperazin-1-yl)methyl)-3-(4-fluorophenethyl)oxazolidin-2-one;
5-(4-Benzhydryl-piperazin-1-ylmethyl)-3-(2-p-tolylethyl)-oxazolidin-2-one;
5-(4-Benzhydryl-piperazin-1-ylmethyl)-3-[2-(4-methoxy-phenyl)-ethyl]-oxazolidin-2-one;
5-((4-benzhydrylpiperazin-1-yl)methyl)-3-(3-phenylpropyl)oxazolidin-2-one;
5-(4-Benzhydryl-piperazin-1-ylmethyl)-3-cyclopentyl-oxazolidin-2-one;
5-((4-benzhydrylpiperazin-1-yl)methyl)-3-(2-phenoxyethyl)oxazolidin-2-one;
5-((4-benzhydrylpiperazin-1-yl)methyl)-3-(cyclohexylmethyl)oxazolidin-2-one;
or a pharmaceutically acceptable form thereof.

9. A method of treating a disease selected from the group consisting of irritable bowel syndrome, dyspepsia, constipation, diarrhea, Crohn's disease, ulcerative colitis, gastroesophageal reflux disease, tachygastria, migraine, neurogenic pain, nociceptive pain, anxiety, depression, benign prostatic hyperplasia, panic disorder, obsessive compulsive disorder, hypertension, anorexia nervosa, priapism, asthma, obstructive airway dysfunction, chronic obstructive pulmonary disease incontinence, and pulmonary hypertension, said method comprising administering to an individual in need of such treatment an effective amount of at least one compound according to the claim 1, or a pharmaceutically acceptable salt thereof, to treat the disease.

10. The method of claim 9, wherein the at least one compound is at least one member selected from the group consisting of:
5-(4-benzhydryl-piperazin-1-ylmethyl)-3-isopropyl-oxazolidin-2-one;
3-allyl-5-(4-benzhydryl-piperazin-1-ylmethyl)-oxazolidin-2-one;
5-(4-benzhydryl-piperazin-1-ylmethyl)-3-tert-butyl-oxazolidin-2-one;
5-(4-benzhydryl-piperazin-1-ylmethyl)-3-cyclopropyl-oxazolidin-2-one;
5-(4-benzhydryl-piperazin-1-ylmethyl)-3-cyclobutyl-oxazolidin-2-one;
5-(4-benzhydryl-piperazin-1-ylmethyl)-3-cyclopentyl-oxazolidin-2-one;
5-(4-benzhydryl-piperazin-1-ylmethyl)-3-cyclohexyl-oxazolidin-2-one;
5-((4-benzhydrylpiperazin-1-yl)methyl)-3-phenyloxazolidin-2-one;
5-(4-benzhydryl-piperazin-1-ylmethyl)-3-cyclopentyl-oxazolidin-2-one;
5-((4-benzhydrylpiperazin-1-yl)methyl)-3-(4-fluorobenzyl)oxazolidin-2-one;
5-(4-benzhydryl-piperazin-1-ylmethyl)-3-(tetrahydropyran-4-ylmethyl)-oxazolidin-2-one;
5-((4-benzhydrylpiperazin-1-yl)methyl)-3-(2-morpholinoethyl)oxazolidin-2-one;
5-(4-benzhydryl-piperazin-1-ylmethyl)-3-propyl-oxazolidin-2-one;
5-(4-benzhydryl-piperazin-1-ylmethyl)-3-benzyl-oxazolidin-2-one;
5-((4-benzhydrylpiperazin-1-yl)methyl)-3-(4-fluorobenzyl)oxazolidin-2-one;
5-((4-benzhydrylpiperazin-1-yl)methyl)-3-(4-methylbenzyl)oxazolidin-2-one;
5-((4-benzhydrylpiperazin-1-yl)methyl)-3-(4-methoxybenzyl)oxazolidin-2-one;
5-((4-benzhydrylpiperazin-1-yl)methyl)-3-phenethyloxazolidin-2-one;
5-((4-benzhydrylpiperazin-1-yl)methyl)-3-(4-fluorophenethyl)oxazolidin-2-one;
5-(4-benzhydryl-piperazin-1-ylmethyl)-3-(2-p-tolylethyl)-oxazolidin-2-one;
5-(4-benzhydryl-piperazin-1-ylmethyl)-3-[2-(4-methoxy-phenyl)-ethyl]-oxazolidin-2-one;

5-((4-benzhydrylpiperazin-1-yl)methyl)-3-(3-phenylpropyl)oxazolidin-2-one;
5-(4-benzhydryl-piperazin-1-ylmethyl)-3-cyclopentyl-oxazolidin-2-one;
5-((4-benzhydrylpiperazin-1-yl)methyl)-3-(2-phenoxyethyl)oxazolidin-2-one;
5-((4-benzhydrylpiperazin-1-yl)methyl)-3-(cyclohexylmethyl)oxazolidin-2-one;
or a pharmaceutically acceptable salt thereof.

11. The method of claim 9, wherein the at least one compound is administered in a composition further comprising at least one excipient.

12. The method of claim 11, wherein the at least one compound is at least one member selected from the group consisting of:
5-(4-benzhydryl-piperazin-1-ylmethyl)-3-isopropyl-oxazolidin-2-one;
3-allyl-5-(4-benzhydryl-piperazin-1-ylmethyl)-oxazolidin-2-one;
5-(4-benzhydryl-piperazin-1-ylmethyl)-3-tert-butyl-oxazolidin-2-one;
5-(4-benzhydryl-piperazin-1-ylmethyl)-3-cyclopropyl-oxazolidin-2-one;
5-(4-benzhydryl-piperazin-1-ylmethyl)-3-cyclobutyl-oxazolidin-2-one;
5-(4-benzhydryl-piperazin-1-ylmethyl)-3-cyclopentyl-oxazolidin-2-one;
5-(4-benzhydryl-piperazin-1-ylmethyl)-3-cyclohexyl-oxazolidin-2-one;
5-((4-benzhydrylpiperazin-1-yl)methyl)-3-phenyloxazolidin-2-one;
5-(4-benzhydryl-piperazin-1-ylmethyl)-3-cyclopentyl-oxazolidin-2-one;
5-((4-benzhydrylpiperazin-1-yl)methyl)-3-(4-fluorobenzyl)oxazolidin-2-one;
5-(4-benzhydryl-piperazin-1-ylmethyl)-3-(tetrahydropyran-4-ylmethyl)-oxazolidin-2-one;
5-((4-benzhydrylpiperazin-1-yl)methyl)-3-(2-morpholinoethyl)oxazolidin-2-one;
5-(4-benzhydryl-piperazin-1-ylmethyl)-3-propyl-oxazolidin-2-one;
5-(4-benzhydryl-piperazin-1-ylmethyl)-3-benzyl-oxazolidin-2-one;
5-((4-benzhydrylpiperazin-1-yl)methyl)-3-(4-fluorobenzyl)oxazolidin-2-one;
5-((4-benzhydrylpiperazin-1-yl)methyl)-3-(4-methylbenzyl)oxazolidin-2-one;
5-((4-benzhydrylpiperazin-1-yl)methyl)-3-(4-methoxybenzyl)oxazolidin-2-one;
5-((4-benzhydrylpiperazin-1-yl)methyl)-3-phenethyloxazolidin-2-one;
5-((4-benzhydrylpiperazin-1-yl)methyl)-3-(4-fluorophenethyl)oxazolidin-2-one;
5-(4-benzhydryl-piperazin-1-ylmethyl)-3-(2-p-tolylethyl)-oxazolidin-2-one;
5-(4-benzhydryl-piperazin-1-ylmethyl)-3-[2-(4-methoxyphenyl)-ethyl]-oxazolidin-2-one;
5-((4-benzhydrylpiperazin-1-yl)methyl)-3-(3-phenylpropyl)oxazolidin-2-one;
5-(4-benzhydryl-piperazin-1-ylmethyl)-3-cyclopentyl-oxazolidin-2-one;
5-((4-benzhydrylpiperazin-1-yl)methyl)-3-(2-phenoxyethyl)oxazolidin-2-one;
5-((4-benzhydrylpiperazin-1-yl)methyl)-3-(cyclohexylmethyl)oxazolidin-2-one;
or a pharmaceutically acceptable salt thereof.

13. A method of inhibiting 5-hydroxytryptamine receptor 2b activity in an individual in need of such treatment comprising administering to the individual an effective amount of at least one compound according to the claim 1, or a pharmaceutically acceptable salt thereof.

14. The method according to claim 13 wherein the at least one compound is at least one member selected from the group consisting of:
5-(4-benzhydryl-piperazin-1-ylmethyl)-3-isopropyl-oxazolidin-2-one;
3-allyl-5-(4-benzhydryl-piperazin-1-ylmethyl)-oxazolidin-2-one;
5-(4-benzhydryl-piperazin-1-ylmethyl)-3-tert-butyl-oxazolidin-2-one;
5-(4-benzhydryl-piperazin-1-ylmethyl)-3-cyclopropyl-oxazolidin-2-one;
5-(4-benzhydryl-piperazin-1-ylmethyl)-3-cyclobutyl-oxazolidin-2-one;
5-(4-benzhydryl-piperazin-1-ylmethyl)-3-cyclopentyl-oxazolidin-2-one;
5-(4-benzhydryl-piperazin-1-ylmethyl)-3-cyclohexyl-oxazolidin-2-one;
5-((4-benzhydrylpiperazin-1-yl)methyl)-3-phenyloxazolidin-2-one;
5-(4-benzhydryl-piperazin-1-ylmethyl)-3-cyclopentyl-oxazolidin-2-one;
5-((4-benzhydrylpiperazin-1-yl)methyl)-3-(4-fluorobenzyl)oxazolidin-2-one;
5-(4-benzhydryl-piperazin-1-ylmethyl)-3-(tetrahydropyran-4-ylmethyl)-oxazolidin-2-one;
5-((4-benzhydrylpiperazin-1-yl)methyl)-3-(2-morpholinoethyl)oxazolidin-2-one;
5-(4-benzhydryl-piperazin-1-ylmethyl)-3-propyl-oxazolidin-2-one;
5-(4-benzhydryl-piperazin-1-ylmethyl)-3-benzyl-oxazolidin-2-one;
5-((4-benzhydrylpiperazin-1-yl)methyl)-3-(4-fluorobenzyl)oxazolidin-2-one;
5-((4-benzhydrylpiperazin-1-yl)methyl)-3-(4-methylbenzyl)oxazolidin-2-one;
5-((4-benzhydrylpiperazin-1-yl)methyl)-3-(4-methoxybenzyl)oxazolidin-2-one;
5-((4-benzhydrylpiperazin-1-yl)methyl)-3-phenethyloxazolidin-2-one;
5-((4-benzhydrylpiperazin-1-yl)methyl)-3-(4-fluorophenethyl)oxazolidin-2-one;
5-(4-benzhydryl-piperazin-1-ylmethyl)-3-(2-p-tolylethyl)-oxazolidin-2-one;
5-(4-benzhydryl-piperazin-1-ylmethyl)-3-[2-(4-methoxyphenyl)-ethyl]-oxazolidin-2-one;
5-((4-benzhydrylpiperazin-1-yl)methyl)-3-(3-phenylpropyl)oxazolidin-2-one;
5-(4-benzhydryl-piperazin-1-ylmethyl)-3-cyclopentyl-oxazolidin-2-one;
5-((4-benzhydrylpiperazin-1-yl)methyl)-3-(2-phenoxyethyl)oxazolidin-2-one;
5-((4-benzhydrylpiperazin-1-yl)methyl)-3-(cyclohexylmethyl)oxazolidin-2-one;
or a pharmaceutically acceptable salt thereof.

* * * * *